(12) United States Patent
Dinesh Kumar et al.

(10) Patent No.: US 7,229,829 B2
(45) Date of Patent: Jun. 12, 2007

(54) TOBACCO RATTLE VIRUS VECTORS AND RELATED COMPOSITIONS AND METHODS

(75) Inventors: Savithramma P. Dinesh Kumar, New Haven, CT (US); Yule Liu, New Haven, CT (US); Michael Schiff, New Haven, CT (US)

(73) Assignee: Yale University, New Haven, CT (US)

( * ) Notice: Subject to any disclaimer, the term of this patent is extended or adjusted under 35 U.S.C. 154(b) by 488 days.

(21) Appl. No.: 10/388,848

(22) Filed: Mar. 14, 2003

(65) Prior Publication Data

US 2003/0182684 A1 Sep. 25, 2003

Related U.S. Application Data

(60) Provisional application No. 60/364,901, filed on Mar. 14, 2002.

(51) Int. Cl.
 A01H 5/00 (2006.01)
 C12N 15/82 (2006.01)
 C12N 5/10 (2006.01)
(52) U.S. Cl. .................. 435/468; 800/278; 800/285
(58) Field of Classification Search .................. None
See application file for complete search history.

(56) References Cited

U.S. PATENT DOCUMENTS

| 5,922,602 A | 7/1999 | Kumagai et al. |
| 6,369,296 B1 | 4/2002 | Ratcliff et al. |
| 6,376,752 B1 | 4/2002 | Kumagai et al. |
| 6,479,291 B2 | 11/2002 | Kumagai et al. |

OTHER PUBLICATIONS

Goldbach et al., Meth. Plant Biochem., 1997, vol. 10b, pp. 103-120.*
Angell et al. Consistent gene silencing in transgenic plants expressing a replicating potato virus X RNA. EMBO Journal. 16(12): 3675-84 (1997).
Baulcombe, D.C. Fast forward genetics based on virus-induced gene silencing. Current Opinion in Plant Virology. 2: 109-13 (1999).
Burton, R.A. et al. Virus-Induced Silencing of a Plant Cellulose Synthase Gene. Plant Cell 12: 691-705 (2000).
Dinesh-Kumar, S.P. et al. Alternatively spliced N resistance gene transcripts: Their possible role in tobacco mosaic virus resistance. PNAS 97(4): 1908-13 (2000).
Dinesh-Kumar, S.P. et al. Structure-function analysis of the tobacco mosaic virus resistance gene N, PNAS 97(26): 14789-94 (2000).
Frisch, D.A. et al. Complete sequence of the binary vector Bin 19. Plant Mol. Bio. 27: 405-9 (1995).
Hooft van Huijsduijnen, R.A.M. et al. cDNA cloning of six mRNAs induced by TMV infection of tobacco and a characterization of their translation products. EMJO Journal 5(9): 2057-61 (1986).
Horsch, R.B. et al. A Simple and General Method for Transferring Genes in Plants. Science 227: 1229-31 (1985).
Kumagai, M.H. et al. Cytoplasmic inhibition of carotenoid biosynthesis with virus-derived RNA. PNAS. 92: 1679-83 (1995).

Liu, Y. et al. Tobacco Rar1, EDS1 and NPR1/NIM1 like genes are required for N-mediated reistance to tobacco mosaic virus. Plant J. 30(4): 415-29 (2002).
Liu, Y. et al. Virus-induced gene silencing in tomato. Plant J. 31(6): 777-86 (2002).
MacFarlane, Stuart A. Molecular biology of the tobraviruses. J. Gen. Virology. 80: 2799-807 (1999).
Martienssen, Robert A. Functional genomics: Probing plant gene function and expression with transposons. PNAS. 95: 2021-26 (1998).
Meissner, R. et al. A high throughput system for transposon lagging and promoter trapping in tomato. Plant J. 22(3): 265-74 (2000).
Nishikura, Kazuko. A Short Primer on RNAi: RNA-Directed RNA Polymerase Acts as a Key Catalyst. Cell 107: 415-18 (2001).
Ratcliff, F. et al. Tobacco rattle virus as a vector for analysis of gene function by silencing. Plant J. 25(2): 237-45 (2001).
Shi, B.J. et al. Plasmid vector for cloning infectious cDNAs from plant RNA viruses: high infectivity of cDNA clones of tomato asperny cucumovirus. J. Gen. Virology 78: 1181-85 (1997).
Shivprasad, S. et al. Heterologous Sequences Greatly Affect Foreign Gene Expression in Tobacco Mosaic Virus-based Vectors. Virology 255: 312-23 (1999).
Turpen, T.H. et al. Transfection of whole plants from wounds inoculated with Agrobacterium tumefaciens containing cDNA of tobacco mosaic virus. J. of Virological Methods 42: 227-40 (1993).
Waterhouse, P.M. et al. Virus resistance and gene silencing in plants can be induced by simultaneous expression of sense and antisense RNA. PNAS 95: 13959-64 (1998).
Waterhouse, P.M. et al. Gene silencing as an adaptive defence against viruses. Nature 411: 834-42 (2001).
Hamilton, W.D.O. et al. The Complete Nucleotide Sequence of Tobacco Rattle Virus RNA-1. J. Gen. Virol. 68: 2563-75 (1987).
Hernandez, C. et al. Sequence of RNA 2 of a Nematode-Transmissable Isolate of Tobacco Rattle Virus. J. Gen. Virol. 76: 2847-51 (1995).
MacFarlane, S.A. et al. Efficient Expression of Foreign Proteins in Roots from Tobravirus Vectors. Virology. 267: 29-35 (2000).
Dangle, J., "Long view from a high plateau," *Nature*, vol. 40, pp. 543-544 (1999).
Hammond-Kosack, K.E., et al., "The Tomato Cf-9 Disease Resistance Gene Functions in Tobacco and Potato to Confer Responsiveness to the Fungal Avirulence Gene Product Avr9," *The Plant Cell*, vol. 10, pp. 1251-1266 (1998).
Holmes, F.O., "Inheritance of Ability to Localize Tobacco-Mosaic Virus," *Phytopathology*, vol. 24, pp. 984-1002 (1934).

(Continued)

*Primary Examiner*—Ashwin Mehta
(74) *Attorney, Agent, or Firm*—Wolf, Greenfield & Sacks, P.C.

(57) ABSTRACT

The application provides, in part, vectors based on novel tobacco rattle virus replicons, as well as methods for using such vectors and transgenic plants.

9 Claims, 33 Drawing Sheets

OTHER PUBLICATIONS

Kinkema, M., et al., "Nuclear Localization of NPR1 Is Required for Activation of *PR* Gene Expression," *The Plant Cell*, vol. 12, pp. 2339-2350 (2000).

Payne, G., et al., "Isolation of genomic clone for pathogenesis-related protein 1a from *Nicotiana tabacum* cv. Xanthi-nc," *Plant Molecular Biology*, vol. 11, pp. 89-94 (1988).

Sijen, T., et al., "On the Role of RNA Amplification in dsRNA-Triggered Gene Silencing," *Cell*, vol. 107, pp. 465-476 (2001).

Smith, H.H., "The Nicotiana genus as a genetic resource," *USDA, Technical Bulletin*, No. 1586, pp. 1-16(1979).

Tai, T.H., et al., "Expression of the Bs2 pepper gene confers resistance to bacterial spot disease in tomato," *PNAS*, vol. 97, No. 24, pp. 14153-14158 (1999).

Thilmony, R.L., et al., "Expression of the Tomato Pto Gene in Tobacco Enhances Resistance to *Pseudomonas syringae* pv tabaci Expressing avrPto," *The Plant Cell*, vol. 7, pp. 1529-1538 (1995).

Ward, E.R., et al., "Coordinate Gene Activity in Response to Agents That Induce Systemic Acquired Resistance," *The Plant Cell*, vol. 3, pp. 1085-1094 (1991).

Whitham, S., et al., "The N gene of tobacco confers resistance to tobacco mosaic virus in transgenic tomato," *PNAS*, vol. 93, pp. 8776-8781 (1996).

Whitham, S., et al., "The Product of the Tobacco Mosaic Virus Resistance Gene N: Similarity to Toll and the Interleukin-1 Receptor," *Cell*, vol. 78, pp. 1101-1115 (1994).

Zhang, Y., et al., "Interaction of NPR1 with basic leucine zipper protein transcription factors that bind sequences required for salicylic acid induction of the *PR-1* gene," *Proc. Natl. Acad. Sci.*, vol. 96, pp. 6523-6528 (1999).

Zhou, J.M, et al., "NPR1 Differentially Interacts with Members of the TGA/OBF Family of Transcription Factors that Bind an Element of the *PR-1* Gene Required for Induction by Salicylic Acid," *MPMI*, vol. 13, No. 2 (2000).

* cited by examiner

```
tEDS1    1   MVRIEEGREVKDELKKACNLAMEAHSLSSGKPYIYKKKSGSHDVFFAFGGTWSVDGWYS
AtEDS1   1   M-AFEALTGINGDLITRSWSASKQAYLTER-----YHKEEAGAVWIFAFQPSFSEKDFTD tEDS1    61  ---STQFGETKIKNALFPSLKSVGTDIVEMVNEAFSRRFEDIIN-KSSIONFVEKAVSDG
AtEDS1   55  PDNKSSFGLIKLNRVQFFCIRKIGKGDVATVNEAILKNLEAVIEFRTSFCASVEMAVRSR tEDS1    117 KQIVFAGHSSGGPLAILAALWCLEHWRKR--PFGNLAYFYCNLAISSCWGQ---NMALLRR
AtEDS1   115 KQIVFIGHSSGGATRILATVGYLEKYFIRNPN-VYLFSRKVTYGAPLVGDSTFSHALGRF tEDS1    173 NAARYFDFVTKYDIVPRIMLAPLSSIQEMACNIFDFLNIKSRFYQHEVGYRGYDAGKNF
AtEDS1   174 FQSRFVNFVTREDIVPRITLARKASVEETLPHVLAQEDE--RN----SSWQESEQRITEF tEDS1    233 EMTWHRSASSVESVMARYIKGCTNLLLFTVSNIVQLSPYRPFGTYIFCIGNGKLVVSFNP
AtEDS1   229 YTSVMRDTSTVANQAVGRITGSARAILETLSSFLDLSPYRPAGTEVFSG-EKRLVAGNGS tEDS1    293 DAVLQLLFYCADMGSETEVEEVVTRSINEFLLYRKEVQESLENQDVVHINNLTDIPLSSN
AtEDS1   288 DAILQLLFYTCQASDEQEWSLIPFRSIRDHHSY-DELVQSMCQKLFNHLDGENSHESS-- tEDS1    353 AIALASDEVVTMNLALIDIGESTRARLCLRAAGEVEKQRRKNEERIDGNKKS--IFEGIR
AtEDS1   345 -------------LIDLGVSTRGRQYVQAAMLELEKKRVEDQKKIIQVIFQERFFKKIA tEDS1    411 KIQ-EYQTKCDIRFVGYYDAFKIQNTDDDRNANVRRIELAGINDEIIEMLKRYELPDRPE
AtEDS1   390 WIEDRVKPKGQAEKNGYYDFKVGHEENDPKANVRRAGLAGVPDIVLGLLRKCQLPDEFS tEDS1    470 GRKEWIQLGTQERRQVEPLDIANYYRFSKHEDTGPYMIRARFKRYNFIQRWLERDKR---
AtEDS1   450 GDIDDIKLATRYRFIVEPLDIANYIRFIKHEDTGPYMKRCRPTRYIVACRGYEDHILKPN tEDS1    527 ----------------WQTCERSD--------SCFWAEVEELRIWRSIHEVQNRDIS
AtEDS1   510 GMIAEDVFWNKVNGLNLGIQLEEIQETLKNSGSECGSCFWAEVEELKGRPYEEMEVRVKT tEDS1    559 LRKTARVESOSGLAG-DDVFFPESTFIKWAKCLPTQHRLAS----NISRKINS-
AtEDS1   570 EGKLREEITAGEVDEKEIFLEGSTFRKWSITLPKNHKSHSPLRDYIMDEITDT
```

Figure 7

```
tNPR1    1  MENCRTAFSDSNDISGSSSICCIGGGMDEHGSPET---SPAEITISDKRLSEALCSIFCAS
AtNPR1   1  MDTTIDGFADSFSISSFSFLATDNTDSSIVGLAAEQVLTGPDVSALQLLSNSFESVFDSP tNPR1   53  LPEHDYFADAKLVVSGPCREIPVHRCILSARSPFFKNLFCCKK-EFNSS-----KVELKE
AtNPR1  61  D---DFYSDAKLVIS-DCREVSFHRCVLSARSSFFKSALALAKKEFDSNNTAAVKIELKE tNPR1  112  VMKFEVGFEAVMEVLAYIYSGKVRPSPKDVCVGMDNDCSEVACRPAVAFLVEVLYTEFT
AtNPR1 117  DAKEYEVGFESAVTVLAYVYSSRVRPPENGISEGADEMCCEVACRPAVDFMLEVLYLASI tNPR1  172  SCISELVDKFQRHLLDIEDKTAADDVMMVISVANICGYAQERLISSCIEIIVKSNVDEIT
AtNPR1 177  SKIHELITLYQRHLLDVVDKVVIEDTLVILKLANICGRAQKRLLDFCKEIIVKSNVDMVS tNPR1  232  LDKALEHDIVKQITCSRASEGIQGPESNGFPDKHVKRIHRALCSDDVELLQMLLREGHTT
AtNPR1 237  LEKSLPPEIVKEIIDRRKELGIEVPKVK----KHVSNYHKALCSDDIELVKLLLKEDHTN tNPR1  292  LDDAYALHYAVAYCDAKTTAELLDLALADINKQNSRGYTVLHVAAMRKEPKIVVSLLTYC
AtNPR1 293  LDDACALHFAVAYCNVKTATDLLKLDLADVHHCNSRGYTVLHVAAMRKEPQLILSLLEKG tNPR1  352  AKHSDLTSDGRKAIKIANRLTRLVFPSKSPEEGRSASNDRLCIEILEQAEKRDPILGCAS
AtNPR1 353  ASASEADLEGRTAIMIAKQADMAGECNNIPPQCEHSLKCRLCVEILEQPDKREQIPRDVP tNPR1  412  VSTAMAGDDLRFKLIYLENRVGLAKILFPM-SAKVAMDIAQIDGTSEFPPASIG-KKMANA
AtNPR1 413  PSFAVAADELKITLLDLENRVALAQRLFPIEADAAMEIAELKGICEFIVTSLEPDRLTGT tNPR1  471  CRTIVDNEAPPKIEEHLNRLKALSRTVELGKRFFPRCSEVLNKINDADDLSEIAYMCN
AtNPR1 473  FRTSPGDKIEPFRIIEEHQSRLKALSKTVELGKRFFPRCSAVLDQINNCEDLAQLACGED tNPR1  531  DTAEEROLAKQRYMELQEIETKAFTED-KEEYDKINNISSSCSSTSKGVDFN-KLPFRK-
AtNPR1 533  DTAEKRLQAKQRYMETQEITKFAFSEDXIELGNSSLTDSTSSISKSTGGKRSNRKLSHRR
```

Figure 8

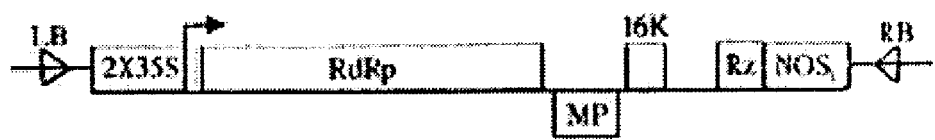
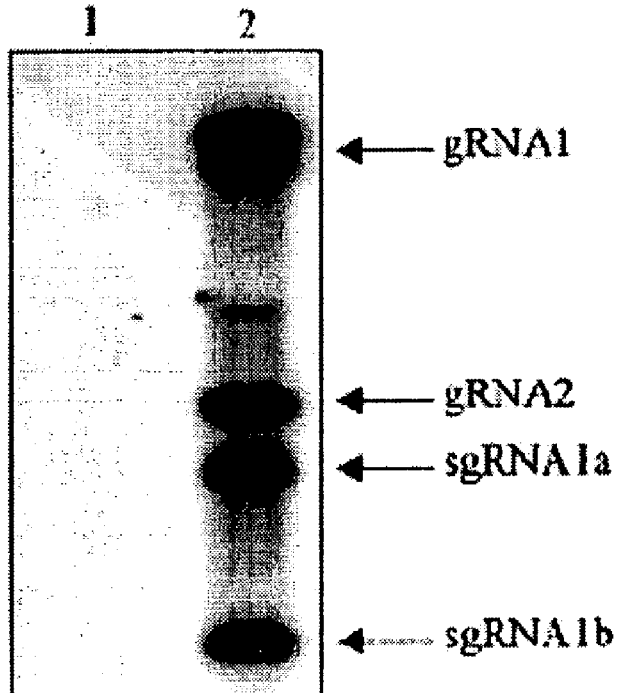
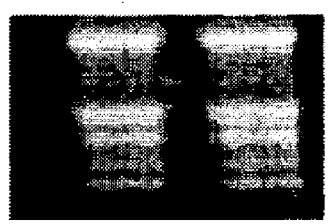
Figure 10

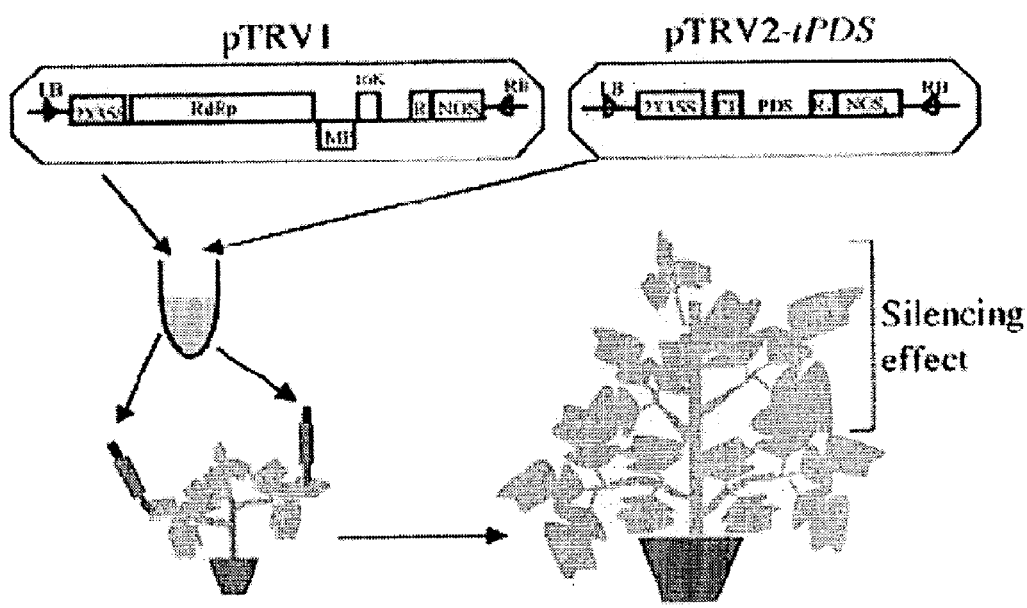
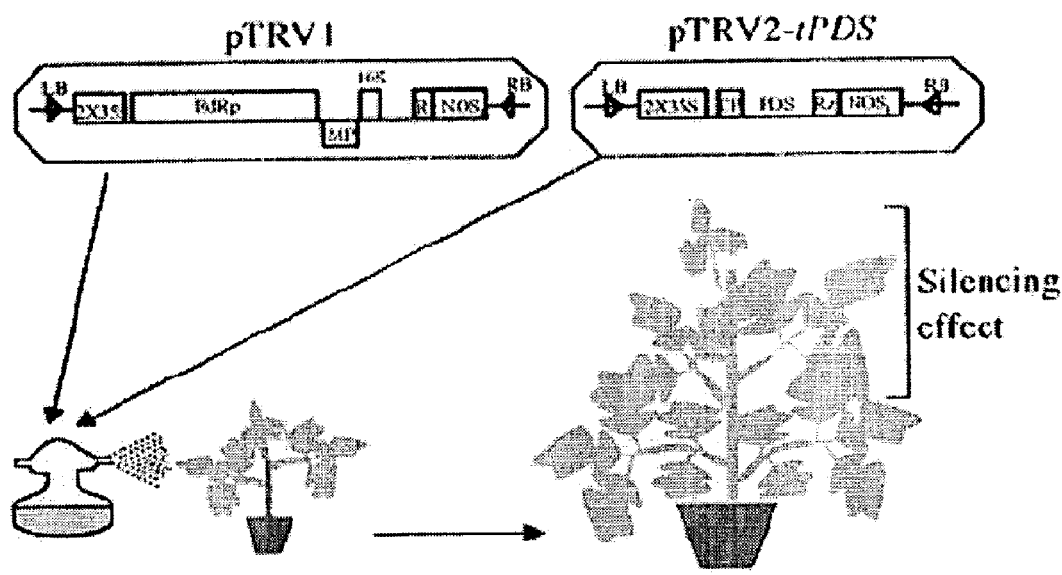
Figure 11 a pTRV2-attP1-attP2
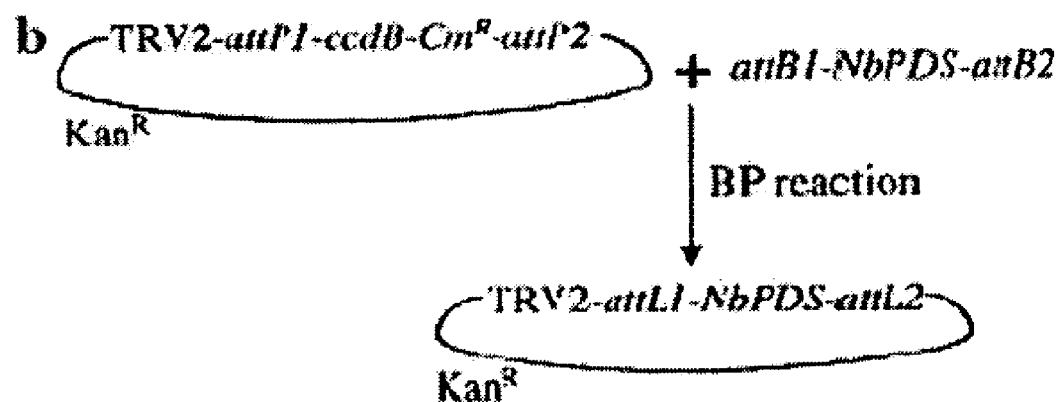
Figure 15 a  pTRV2-attR1-attR2
b 
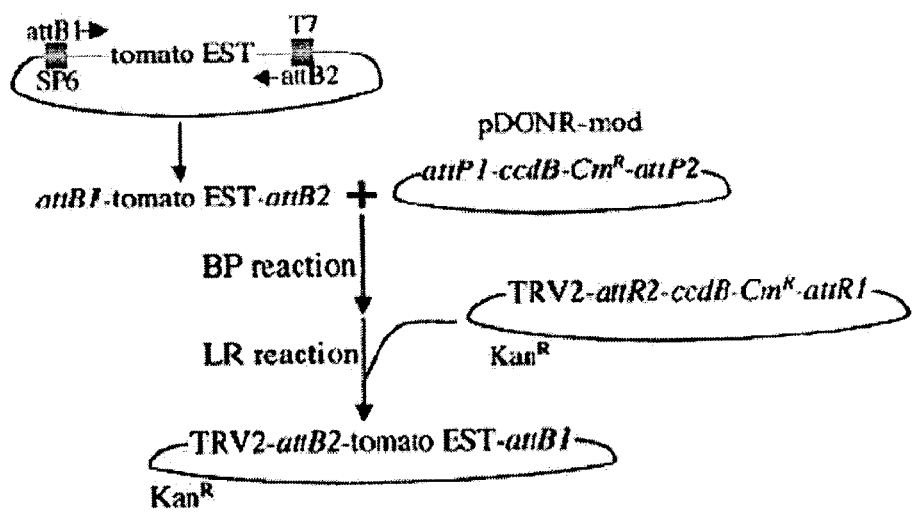
c 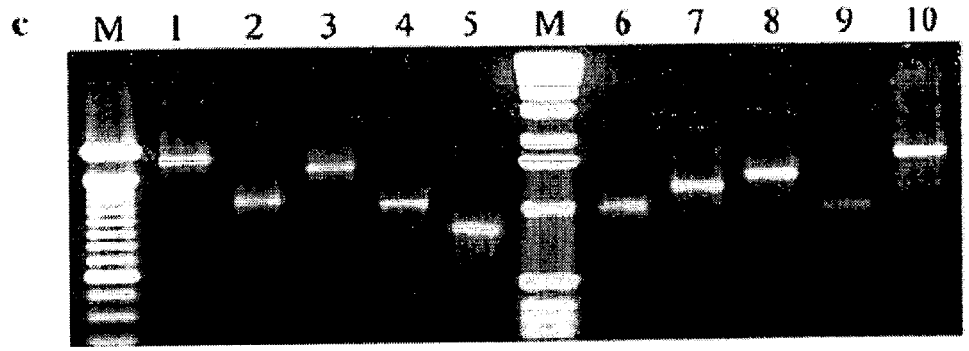
d 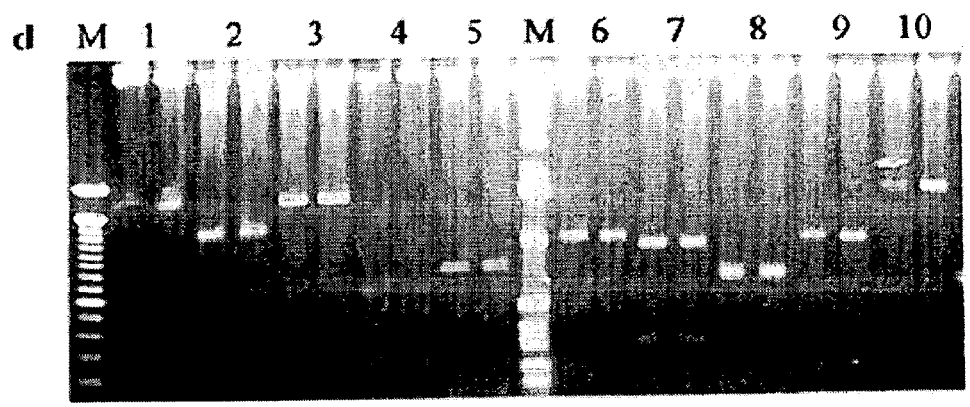
Figure 16

```
        Y-POL  MANGNFKLSQLLNVDEMSAEQRSHFFDLMLTKPDCEIGQMMQRVVVDKVDDMIRERKTKD
        D-POL  MANGNFKLSQLLNVDEMSAEQRSHFFDLMLTKPDCEIGQMMQRVVVDKVDDMIRERKTKD
               ************************************************************

5     Y-POL  PVIVHEVLSQKEQNKLMEIYPEFNIVFKDDKNMVHGFAAAERKLQALLLLDRVPALQEVD
        D-POL  PVIVHEVLSQKEQNKLMEIYPEFNIVFKDDKNMVHGFAAAERKLQALLLLDRVPALQEVD
               ************************************************************

Y-POL  DIGGQWSFWVTRGEKRIHSCCPNLDIRDDQREISRQIFLTAIGDQARSGKRQMSENELWM
 10     D-POL  DIGGQWSFWVTRGEKRIHSCCPNLDIRDDQREISRQIFLTAIGDQARSGKRQMSENELWM
               ************************************************************

Y-POL  YDQFRENIAAPNAVRCNNTYQGCTCRGFSDGKKKGAQYAIALHSLYDFKLKDLMATMVEK
        D-POL  YDQFRENIAAPNAVRCNNTYQGCTCRGFSDGKKKGAQYAIALHSLYDFKLKDLMATMVEK
 15            ************************************************************

Y-POL  KTKVVHAAMLFAPESMLVDEGPLPSVDGYYMKKNGKIYFGFEKDPSFSYIHDWEEYKKYL
        D-POL  KTKVVHAAMLFAPESMLVDEGPLPSVDGYYMKKNGKIYFGFEKDPSFSYIHDWEEYKKYL
               ************************************************************
 20
        Y-POL  LGKPVSYQGNVFYFEPWQVRGDTMLFSIYRIAGVPRRSLSSQEYYRRIYISRWEN_MVVVP
        D-POL  LGKPVSYQGNVFYFEPWQVRGDTMLFSIYRIAGVPRRSLSSQEYYRRIYISRWES_MVVVP
               *********************************************************  *****

25     Y-POL  IFDLVESTRELVKKDLFVEKQFMDKCLDYIARLSDQQLTISNVKSYLSSNNWVLFINGAA
        D-POL  IFDLVESTRELVKKDLFVEKQFMDKCLDYIARLSDQQLTISNVKSYLSSNNWVLFINGAA
               ************************************************************

Y-POL  VKNKQSVDSRDLQLLAQTLLVKEQVARPVMRELREAILTETKPITSLTDVLGLISRKLWK
 30     D-POL  VKNKQSVDSRDLQLLAQTLLVKEQVARPVMRELREAILTETKPITSLTDVLGLISRKLWK
               ************************************************************

Y-POL  QFANKIAVGGFVGMVGTLIGFYPKKVLTWAKDTPNGPELCYENSHKTKVIVFLSVVYAIG
        D-POL  QFANKIAVGGFVGMVGTLIGFYPKKVLTWAKDTPNGPELCYENSHKTKVIVFLSVVYAIG
 35            ************************************************************

Y-POL  GITLMRRDIRDGLVKKLCDMFDIKRGAHVLDVENPCRYYEINDFFSSLYSASESGETVLP
        D-POL  GITLMRRDIRDGLVKKLCDMFDIKRGAHVLDVENPCRYYEINDFFSSLYSASESGETVLP
               ************************************************************
 40
        Y-POL  DLSEVKAKSDKLLQQKKEIADEFLSAKFSNYSGSSVRTSPPSVVGSSRSGLGLLLEDSNV
        D-POL  DLSEVKAKSDKLLQQKKEIADEFLSAKFSNYSGSSVRTSPPSVVGSSRSGLGLLLEDSNV
               ************************************************************

45     Y-POL  LTQARVGVSRKVDDEEIMEQFLSGLIDTEAEIDEVVP_AFSAECERGETSGTKVLCKPLTP
        D-POL  LTQARVGVSRKVDDEEIMEQFLSGLIDTEAEIDEVVS_AFSAECERGETSGTKVLCKPLTP
               ************************************  ***********************

Y-POL  PGFENVLPAVKPLVSKGKTVKRVDYFQVMGGERLPKRPVVSGDDSVDARREFLYYLDAER
 50     D-POL  PGFENVLPAVKPLVSKGKTVKRVDYFQVMGGERLPKRPVVSGDDSVDARREFLYYLDAER
               ************************************************************
```

Figure 18A

```
     Y-POL  VAQNDEIMSLYRDYSRGVIRTGGQNYPHGLGVWDVEMKNWCIRPVVTEHAYVFQPDKRMD
     D-POL  VAQNDEIMSLYRDYSRGVIRTGGQNYPHGLGVWDVEMKNWCIRPVVTEHAYVFQPDKRMD
            ************************************************************
 5
     Y-POL  DWSGYLEVAVWERGMLVNDFAVERMSDYVIVCDQTYLCNNRLILDNLSALDLGPVNCSFE
     D-POL  DWSGYLEVAVWERGMLVNDFAVERMSDYVIVCDQTYLCNNRLILDNLSALDLGPVNCSFE
            ************************************************************
10   Y-POL  LVDGVPGCGKSTMIVNSANPCVDVVLSTGRAATDDLIERFASKGFPCKLKRRVKTVDSFL
     D-POL  LVDGVPGCGKSTMIVNSANPCVDVVLSTGRAATDDLIERFASKGFPCKLKRRVKTVDSFL
            ************************************************************

Y-POL  MHCVDGSLTGDVLHFDEALMAHAGMVYFCAQIAGAKRCICQGDQNQISFKPRVSQVDLRF
15   D-POL  MHCVDGSLTGDVLHFDEALMAHAGMVYFCAQIAGAKRCICQGDQNQISFKPRVSQVDLRF
            ************************************************************

Y-POL  SSLVGKFDIVTEKRETYRSPADVAAVLNKYYTGDVRTHNATANSMTVRKIVSKEQVSLKP
     D-POL  SSLVGKFDIVTEKRETYRSPADVAAVLNKYYTGDVRTHNATANSMTVRKIVSKEQVSLKP
            ************************************************************
20
     Y-POL  GAQYITFLQSEKKELVNLLALRKVAAKVSTVHESQGETFKDVVLVRTKPTDDSIARGREY
     D-POL  GAQYITFLQSEKKELVNLLALRKVAAKVSTVHESQGETFKDVVLVRTKPTDDSIARGREY
            ************************************************************
25
     Y-POL  LIVALSRHTQSLVYETVKEDDVSKEIRESAALTKAALARFFVTETVLZRFRSRFDVFRHH
     D-POL  LIVALSRHTQSLVYETVKEDDVSKEIRESAALTKAALARFFVTETVLZRFRSRFDVFRHH
            ************************************************************

30   Y-POL  EGPCAVPDSGTITDLEMWYDALFPGNSLRDSSLDGYLVATTDCNLRLDNVTIKSGNWKDK
     D-POL  EGPCAVPDSGTITDLEMWYDALFPGNSLRDSSLDGYLVATTDCNLRLDNVTIKSGNWKDK
            ************************************************************

Y-POL  FAEKETFLKPVIRTAMPDKRKTTQLESLLALQKRNQAAPDLQENVHATVLIEETMKKLKS
35   D-POL  FAEKETFLKPVIRTAMPDKRKTTQLESLLALQKRNQAAPDLQENVHATVLIEETMKKLKS
            ************************************************************

Y-POL  VVYDVGKIRADPIVNRAQMERWWRNQSTAVQAKVVADVRELHEIDYSSYMYMIKSDVKPK
     D-POL  VVYDVGKIRADPIVNRAQMERWWRNQSTAVQAKVVADVRELHEIDYSSYMYMIKSDVKPK
40          ************************************************************

Y-POL  TDLTPQFEYSALQTVVYHEKLINSLFGPIFKEINERKLDAMQPHFVFNTRMTSSDLNDRV
     D-POL  TDLTPQFEYSALQTVVYHEKLINSLFGPIFKEINERKLDAMQPHFVFNTRMTSSDLNDRV
            ************************************************************
45
     Y-POL  KFLNTEAAYDFVEIDMSKFDKSANRFHLQLQLEIYRLFGLDEWAAFLWEVSHTQTTVRDI
     D-POL  KFLNTEAAYDFVEIDMSKFDKSANRFHLQLQLEIYRLFGLDEWAAFLWEVSHTQTTVRDI
            ************************************************************

50   Y-POL  QNGMMAHIWYQQKSGDADTYNANSDRTLCALLSELPLEKAVMVTYGGDDSLIAFPRGTQF
     D-POL  QNGMMAHIWYQQKSGDADTYNANSDRTLCALLSELPLEKAVMVTYGGDDSLIAFPRGTQF
            ************************************************************
```

Figure 18B

```
Y-POL  VDPCPKLATKWNFECKIFKYDVPMFCGKFLLKTSSCYEFVPDPVKVLTKLGKKSIKDVQH
D-POL  VDPCPKLATKWNFECKIFKYDVPMFCGKFLLKTSSCYEFVPDPVKVLTKLGKKSIKDVQH
       ************************************************************

Y-POL  LAEIYISLNDSNRALGNYMVVSKLSESVSDRYLYKGDSVHALCALWKHIKSFTALCTLFR
D-POL  LAEIYISLNDSNRALGNYMVVSKLSESVSDRYLYKGDSVHALCALWKHIKSFTALCTLFR
       ************************************************************

Y-POL  DENDKELNPAKVDWKKAQRAVSNFYDW
D-POL  DENDKELNPAKVDWKKAQRAVSNFYDW
       ***************************
```

Figure 18C

```
Y-MP  MEDKSLVTLKKKTFEVSKFSNLGAIELFVDGRRKRPKYFHRRRETVLNHVGGKKSEHKLD
D-MP  MEDKSLVTLKKKTFEVSKFSNLGAIELFVDGRRKRPKYFHRRRETVLNHVGGKKSEHKLD
      ************************************************************

Y-MP  VFDQRDYKMIKSYAFLKI VGVQLVVTSHLPADTPGFIQIDLLDSRLTEKRKRGKTIQRFK
D-MP  VFDQRDYKMIKSYAFLKV VGVQLVVTSHLPADTPGFIQIDLLDSRLTEKRKRGKTIQRFK
      ***************** . *****************************************

Y-MP  ARACDNCSVAQYKVEYSISTQENVLDVWKVGCISEGVPVCDGTYPFSIEVSLIWVATDST
D-MP  ARACDNCSVAQYKVEYSISTQENVLDVWKVGCISEGVPVCDGTYPFSIEVSLIWVATDST
      ************************************************************

Y-MP  RRLNVEELNSSDYIEGDFTDQEVFGEFMSLKQVEMKTIEAKYDGPYRPATTRPKSLLSSE
D-MP  RRLNVEELNSSDYIEGDFTDQEVFGEFMSLKQVEMKTIEAKYDGPYRPATTRPKSLLSSE
      ************************************************************

Y-MP  DVKRASNKKNSS
D-MP  DVKRASNKKNSS
      ************
```

Figure 19

```
Y-RNA1  ATAAAACATTTCAATCCTTTGAACGCGGTAGAACGTGCTAATTGGATTTTGGTGAGAACG
D-RNA1  ATAAAACATTTCAATCCTTTGAACGCGGTAGAACGTGCTAATTGGATTTTGGTGAGAACG
        ************************************************************

Y-RNA1  CGGTAGAACGTACTTATCACCTACAGTTTTATTTTGTTTTTCTTTTTGGTTTAATCTATC
D-RNA1  CGGTAGAACGTACTTATCACCTACAGTTTTATTTTGTTTTTCTTTTTGGTTTAATCTATC
        ************************************************************

Y-RNA1  CAGCTTAGTACCGAGTGGGGGAAAGTGACTGGTGTGCCTAAAACCTTTTCTTTGATACTT
D-RNA1  CAGCTTAGTACCGAGTGGGGGAAAGTGACTGGTGTGCCTAAAACCTTTTCTTTGATACTT
        ************************************************************

Y-RNA1  TGTAAAAATACATACAGATACAATGGCGAACGGTAACTTCAAGTTGTCTCAATTGCTCAA
D-RNA1  TGTAAAAATACATACAGATACAATGGCGAACGGTAACTTCAAGTTGTCTCAATTGCTCAA
        ************************************************************

Y-RNA1  TGTGGACGAGATGTCTGCTGACCAGAGGAGTCATTTCTTTGACTTGATGCTGACTAAACC
D-RNA1  TGTGGACGAGATGTCTGCTGACCAGAGGAGTCATTTCTTTGACTTGATGCTGACTAAACC
        ************************************************************

Y-RNA1  TGATTGTGAGATCGGGCAAATGATGCAAAGAGTTGTTGTTGATAAAGTCGATGACATGAT
D-RNA1  TGATTGTGAGATCGGGCAAATGATGCAAAGAGTTGTTGTTGATAAAGTCGATGACATGAT
        ************************************************************

Y-RNA1  TAGAGAAAGAAAGACTAAAGATCCAGTGATTGTTCATGAAGTTCTTTCTCAGAAGGAACA
D-RNA1  TAGAGAAAGAAAGACTAAAGATCCAGTGATTGTTCATGAAGTTCTTTCTCAGAAGGAACA
        ************************************************************

Y-RNA1  GAACAAGTTGATGGAAATTTATCCTGAATTCAATATCGTGTTTAAAGACGACAAAAACAT
D-RNA1  GAACAAGTTGATGGAAATTTATCCTGAATTCAATATCGTGTTTAAAGACGACAAAAACAT
        ************************************************************

Y-RNA1  GGTTCATGGGTTTGCGGCTGCTGAGCGAAAACTACAAGCTTTATTGCTTTTAGATAGAGT
D-RNA1  GGTTCATGGGTTTGCGGCTGCTGAGCGAAAACTACAAGCTTTATTGCTTTTAGATAGAGT
        ************************************************************

Y-RNA1  TCCTGCTCTGCAAGAGGTGGATGACATCGGTGGTCAATGGTCGTTTTGGGTAACTAGAGG
D-RNA1  TCCTGCTCTGCAAGAGGTGGATGACATCGGTGGTCAATGGTCGTTTTGGGTAACTAGAGG
        ************************************************************

Y-RNA1  TGAGAAAAGGATTCATTCCTGTTGTCCAAATCTAGATATTCGGGATGATCAGAGAGAAAT
D-RNA1  TGAGAAAAGGATTCATTCCTGTTGTCCAAATCTAGATATTCGGGATGATCAGAGAGAAAT
        ************************************************************

Y-RNA1  TTCTCGACAGATATTTCTTACTGCTATTGGTGATCAAGCTAGAAGTGGTAAGAGACAGAT
D-RNA1  TTCTCGACAGATATTTCTTACTGCTATTGGTGATCAAGCTAGAAGTGGTAAGAGACAGAT
        ************************************************************

Y-RNA1  GTCGGAGAATGAGCTGTGGATGTATGACCAATTTCGTGAAAATATTGCTGCGCCTAACGC
D-RNA1  GTCGGAGAATGAGCTGTGGATGTATGACCAATTTCGTGAAAATATTGCTGCGCCTAACGC
        ************************************************************
```

Figure 20A

```
Y-RNA1  GGTTAGGTGCAATAATACATATCAGGGTTGTACATGTAGGGGTTTTTCTGATGGTAAGAA
D-RNA1  GGTTAGGTGCAATAATACATATCAGGGTTGTACATGTAGGGGTTTTTCTGATGGTAAGAA
        ************************************************************

Y-RNA1  GAAAGGCGCGCAGTATGCGATAGCTCTTCACAGCCTGTATGACTTCAAGTTGAAAGACTT
D-RNA1  GAAAGGCGCGCAGTATGCGATAGCTCTTCACAGCCTGTATGACTTCAAGTTGAAAGACTT
        ************************************************************

Y-RNA1  GATGGCTACTATGGTTGAGAAGAAAACTAAAGTGGTTCATGCTGCTATGCTTTTTGCTCC
D-RNA1  GATGGCTACTATGGTTGAGAAGAAAACTAAAGTGGTTCATGCTGCTATGCTTTTTGCTCC
        ************************************************************

Y-RNA1  TGAAAGTATGTTAGTGGACGAAGGTCCATTACCTTCTGTTGACGGTTACTACATGAAGAA
D-RNA1  TGAAAGTATGTTAGTGGACGAAGGTCCATTACCTTCTGTTGACGGTTACTACATGAAGAA
        ************************************************************

Y-RNA1  GAACGGGAAGATCTATTTCGGTTTTGAGAAAGATCCTTCCTTTTCTTACATTCATGACTG
D-RNA1  GAACGGGAAGATCTATTTCGGTTTTGAGAAAGATCCTTCCTTTTCTTACATTCATGACTG
        ************************************************************

Y-RNA1  GGAAGAGTACAAGAAGTATCTACTGGGGAAGCCAGTGAGTTACCAAGGGAATGTGTTCTA
D-RNA1  GGAAGAGTACAAGAAGTATCTACTGGGGAAGCCAGTGAGTTACCAAGGGAATGTGTTCTA
        ************************************************************

Y-RNA1  CTTCGAACCGTGGCAGGTGAGAGGAGACACAATGCTTTTTTCGATCTACAGGATAGCTGG
D-RNA1  CTTCGAACCGTGGCAGGTGAGAGGAGACACAATGCTTTTTTCGATCTACAGGATAGCTGG
        ************************************************************

Y-RNA1  AGTTCCGAGGAGGTCTCTATCATCGCAAGAGTACTACCGAAGAATATATATCAGTAGATG
D-RNA1  AGTTCCGAGGAGGTCTCTATCATCGCAAGAGTACTACCGAAGAATATATATCAGTAGATG
        ************************************************************

Y-RNA1  GGAAAACATGGTTGTTGTCCCAATTTTCGATCTGGTCGAATCAACGCGAGAGTTGGTCAA
D-RNA1  GGAAAGCATGGTTGTTGTCCCAATTTTCGATCTGGTCGAATCAACGCGAGAGTTGGTCAA
        *****  *****************************************************

Y-RNA1  GAAAGACCTGTTTGTAGAGAAACAATTCATGGACAAGTGTTTGGATTACATAGCTAGGTT
D-RNA1  GAAAGACCTGTTTGTAGAGAAACAATTCATGGACAAGTGTTTGGATTACATAGCTAGGTT
        ************************************************************

Y-RNA1  ATCTGACCAGCAGCTGACCATAAGCAATGTTAAATCATACTTGAGTTCAAATAATTGGGT
D-RNA1  ATCTGACCAGCAGCTGACCATAAGCAATGTTAAATCATACTTGAGTTCAAATAATTGGGT
        ************************************************************

Y-RNA1  CTTATTCATAAACGGGGCGGCCGTGAAGAACAAGCAAAGTGTAGATTCTCGAGATTTACA
D-RNA1  CTTATTCATAAACGGGGCGGCCGTGAAGAACAAGCAAAGTGTAGATTCTCGAGATTTACA
        ************************************************************

Y-RNA1  GTTGTTGGCTCAAACTTTGCTAGTGAAGGAACAAGTGGCGAGACCTGTCATGAGGGAGTT
D-RNA1  GTTGTTGGCTCAAACTTTGCTAGTGAAGGAACAAGTGGCGAGACCTGTCATGAGGGAGTT
        ************************************************************
```

Figure 20B

```
Y-RNA1  GCGTGAAGCAATTCTGACTGAGACGAAACCTATCACGTCATTGACTGATGTGCTGGGTTT
D-RNA1  GCGTGAAGCAATTCTGACTGAGACGAAACCTATCACGTCATTGACTGATGTGCTGGGTTT
        ************************************************************

Y-RNA1  AATATCAAGAAAACTGTGGAAGCAGTTTGCTAACAAGATCGCAGTCGGCGGATTCGTTGG
D-RNA1  AATATCAAGAAAACTGTGGAAGCAGTTTGCTAACAAGATCGCAGTCGGCGGATTCGTTGG
        ************************************************************

Y-RNA1  CATGGTTGGTACTCTAATTGGATTCTATCCAAAGAAGGTACTAACCTGGGCGAAGGACAC
D-RNA1  CATGGTTGGTACTCTAATTGGATTCTATCCAAAGAAGGTACTAACCTGGGCGAAGGACAC
        ************************************************************

Y-RNA1  ACCAAATGGTCCAGAACTATGTTACGAGAACTCGCACAAAACCAAGGTGATAGTATTTCT
D-RNA1  ACCAAATGGTCCAGAACTATGTTACGAGAACTCGCACAAAACCAAGGTGATAGTATTTCT
        ************************************************************

Y-RNA1  GAGTGTTGTGTATGCCATTGGAGGAATCACGCTTATGCGTCGAGACATCCGAGATGGACT
D-RNA1  GAGTGTTGTGTATGCCATTGGAGGAATCACGCTTATGCGTCGAGACATCCGAGATGGACT
        ************************************************************

Y-RNA1  GGTGAAAAAACTATGTGATATGTTTGATATCAAACGGGGGCCCATGTCTTAGACGTTGA
D-RNA1  GGTGAAAAAACTATGTGATATGTTTGATATCAAACGGGGGCCCATGTCTTAGACGTTGA
        ************************************************************

Y-RNA1  GAATCCGTGCCGCTATTATGAAATCAACGATTTCTTTAGCAGTCTGTATTCGGCATCTGA
D-RNA1  GAATCCGTGCCGCTATTATGAAATCAACGATTTCTTTAGCAGTCTGTATTCGGCATCTGA
        ************************************************************

Y-RNA1  GTCCGGTGAGACCGTTTTACCAGATTTATCCGAGGTAAAAGCCAAGTCTGATAAGCTATT
D-RNA1  GTCCGGTGAGACCGTTTTACCAGATTTATCCGAGGTAAAAGCCAAGTCTGATAAGCTATT
        ************************************************************

Y-RNA1  GCAGCAGAAGAAAGAAATCGCTGACGAGTTTCTAAGTGCAAAATTCTCTAACTATTCTGG
D-RNA1  GCAGCAGAAGAAAGAAATCGCTGACGAGTTTCTAAGTGCAAAATTCTCTAACTATTCTGG
        ************************************************************

Y-RNA1  CAGTTCGGTGAGAACTTCTCCACCATCGGTGGTCGGTTCATCTCGAAGCGGACTGGGTCT
D-RNA1  CAGTTCGGTGAGAACTTCTCCACCATCGGTGGTCGGTTCATCTCGAAGCGGACTGGGTCT
        ************************************************************

Y-RNA1  GTTGTTGGAAGACAGTAACGTGCTGACCCAAGCTAGAGTTGGAGTTTCAAGAAACGTAGA
D-RNA1  GTTGTTGGAAGACAGTAACGTGCTGACCCAAGCTAGAGTTGGAGTTTCAAGAAAGGTAGA
        ************************************************************

Y-RNA1  CGATGAGGAGATCATGGAGCAGTTTCTGAGTGGTCTTATTGACACTGAAGCAGAAATTGA
D-RNA1  CGATGAGGAGATCATGGAGCAGTTTCTGAGTGGTCTTATTGACACTGAAGCAGAAATTGA
        ************************************************************

Y-RNA1  CGAGGTTGTTC CAGCCTTTTCAGCTGAATGTGAAAGAGGGGAAACAAGCGGTACAAAGGT
D-RNA1  CGAGGTTGTTT CAGCCTTTTCAGCTGAATGTGAAAGAGGGGAAACAAGCGGTACAAAGGT
        ********** *************************************************
```

Figure 20C

```
Y-RNA1 GTTGTGTAAACCTTTAACGCCACCAGGATTTGAGAACGTGTTGCCAGCTGTCAAACCTTT
D-RNA1 GTTGTGTAAACCTTTAACGCCACCAGGATTTGAGAACGTGTTGCCAGCTGTCAAACCTTT
       ************************************************************

Y-RNA1 GGTCAGCAAAGGAAAAACGGTCAAACGTGTCGATTACTTCCAAGTGATGCGAGGTGAGAG
D-RNA1 GGTCAGCAAAGGAAAAACGGTCAAACGTGTCGATTACTTCCAAGTGATGGGAGGTGAGAG
       ************************************************************

Y-RNA1 ATTACCAAAAAGGCCGGTTGTCAGTGGAGACGATTCTGTGGACGCTAGAAGAGAGTTTCT
D-RNA1 ATTACCAAAAAGGCCGGTTGTCAGTGGAGACGATTCTGTGGACGCTAGAAGAGAGTTTCT
       ************************************************************

Y-RNA1 GTACTACTTAGATGCGGAGAGAGTCGCTCAAAATGATGAAATTATGTCTCTGTATCGTGA
D-RNA1 GTACTACTTAGATGCGGAGAGAGTCGCTCAAAATGATGAAATTATGTCTCTGTATCGTGA
       ************************************************************

Y-RNA1 CTATTCGAGAGGAGTTATTCGAACTGGAGGTCAGAATTACCCGCACGGACTGGGAGTGTG
D-RNA1 CTATTCGAGAGGAGTTATTCGAACTGGAGGTCAGAATTACCCGCACGGACTGGGAGTGTG
       ************************************************************

Y-RNA1 GGATGTGGAGATGAAGAACTGGTGCATACGTCCAGTGGTCACTGAACATGCTTATGTGTT
D-RNA1 GGATGTGGAGATGAAGAACTGGTGCATACGTCCAGTGGTCACTGAACATGCTTATGTGTT
       ************************************************************

Y-RNA1 CCAACCAGACAAACGTATGGATGATTGGTCGGGATACTTAGAAGTGGCTGTTTGGGAACG
D-RNA1 CCAACCAGACAAACGTATGGATGATTGGTCGGGATACTTAGAAGTGGCTGTTTGGGAACG
       ************************************************************

Y-RNA1 AGGTATGTTGGTCAACGACTTCGCGGTCGAAAGGATGAGTGATTATGTCATAGTTTGCGA
D-RNA1 AGGTATGTTGGTCAACGACTTCGCGGTCGAAAGGATGAGTGATTATGTCATAGTTTGCGA
       ************************************************************

Y-RNA1 TCAGACGTATCTTTGCAATAACAGGTTGATCTTGGACAATTTAAGTGCCCTGGATCTAGG
D-RNA1 TCAGACGTATCTTTGCAATAACAGGTTGATCTTGGACAATTTAAGTGCCCTGGATCTAGG
       ************************************************************

Y-RNA1 ACCAGTTAACTGTTCTTTTGAATTAGTTGACGGTGTACCTGGTTGTGGTAAGTCGACAAT
D-RNA1 ACCAGTTAACTGTTCTTTTGAATTAGTTGACGGTGTACCTGGTTGTGGTAAGTCGACAAT
       ************************************************************

Y-RNA1 GATTGTCAACTCAGCTAATCCTTGTGTCGATGTGGTTCTCTCTACTGGGAGAGCAGCAAC
D-RNA1 GATTGTCAACTCAGCTAATCCTTGTGTCGATGTGGTTCTCTCTACTGGGAGAGCAGCAAC
       ************************************************************

Y-RNA1 CGACGACTTGATCGAGAGATTCGCGAGCAAAGGTTTTCCATGCAAATTGAAAAGGAGAGT
D-RNA1 CGACGACTTGATCGAGAGATTCGCGAGCAAAGGTTTTCCATGCAAATTGAAAAGGAGAGT
       ************************************************************

Y-RNA1 GAAGACGGTTGATTCTTTTTTGATGCATTGTGTT_GATGGTTCTTTAACCGGAGACGTGTT
D-RNA1 GAAGACGGTTGATTCTTTTTTGATGCATTGTGTC_GATGGTTCTTTAACCGGAGACGTGTT
       ********************************* **************************
```

Figure 20D

```
Y-RNA1  GCATTTCGAT GAAGCTCTCATGGCCCATGCTGGTATGGTGTACTTTTGCGCTCAGATAGC
D-RNA1  GCATTTCGAC GAAGCTCTCATGGCCCATGCTGGTATGGTGTACTTTTGCGCTCAGATAGC
        ********* *******************************************

Y-RNA1  TGGTGCTAAACGATGTATCTGTCAAGGAGATCAGAATCAAATTTCTTTCAAGCCTAGGGT
D-RNA1  TGGTGCTAAACGATGTATCTGTCAAGGAGATCAGAATCAAATTTCTTTCAAGCCTAGGGT
        ************************************************************

Y-RNA1  ATCTCAAGTTGATTTGAGGTTTTCTAGTCTGGTCGGAAAGTTTGACATTGTTACAGAAAA
D-RNA1  ATCTCAAGTTGATTTGAGGTTTTCTAGTCTGGTCGGAAAGTTTGACATTGTTACAGAAAA
        ************************************************************

Y-RNA1  AAGAGAAACTTACAGAAGTCCAGCAGATGTGGCTGCCGTATTGAACAAGTACTATACTGG
D-RNA1  AAGAGAAACTTACAGAAGTCCAGCAGATGTGGCTGCCGTATTGAACAAGTACTATACTGG
        ************************************************************

Y-RNA1  AGATGTCAGAACACATAACGCGACTGCTAATTCGATGACGGTGAGGAAGATTGTGTCTAA
D-RNA1  AGATGTCAGAACACATAACGCGACTGCTAATTCGATGACGGTGAGGAAGATTGTGTCTAA
        ************************************************************

Y-RNA1  AGAACAGGTTTCTTTGAAGCCTGGTGCTCAGTACATAACTTTCCTTCAGTCTGAGAAGAA
D-RNA1  AGAACAGGTTTCTTTGAAGCCTGGTGCTCAGTACATAACTTTCCTTCAGTCTGAGAAGAA
        ************************************************************

Y-RNA1  GGAGTTGGTAAATTTGTTGGCATTGAGGAAAGTGGCAGCTAAAGTGAGTACAGTACACGA
D-RNA1  GGAGTTGGTAAATTTGTTGGCATTGAGGAAAGTGGCAGCTAAAGTGAGTACAGTACACGA
        ************************************************************

Y-RNA1  GTCGCAAGGACAGACATTCAAAGATGTAGTCCTAGTCAGGACGAAACCTACGGATGACTC
D-RNA1  GTCGCAAGGAGAGACATTCAAAGATGTAGTCCTAGTCAGGACGAAACCTACGGATGACTC
        ********** *************************************************

Y-RNA1  AATCGCTAGAGGTCGGGAGTACTTAATCGTGGCG TTGTCGCGTCACACACAATCACTTGT
D-RNA1  AATCGCTAGAGGTCGGGAGTACTTAATCGTGGCA TTGTCGCGTCACACACAATCACTTGT
        ********************************* **************************

Y-RNA1  GTATGAAACTGTGAAAGAGGACGATGTAAGCAAAGAGATCAGGGAAAGTGCCGCGCTTAC
D-RNA1  GTATGAAACTGTGAAAGAGGACGATGTAAGCAAAGAGATCAGGGAAAGTGCCGCGCTTAC
        ************************************************************

Y-RNA1  GAAGGCGGCTTTGGCAAGATTTTTTGTTACTGAGACCGTCTTATGACGGTTTCGGTCTAG
D-RNA1  GAAGGCGGCTTTGGCAAGATTTTTTGTTACTGAGACCGTCTTATGACGGTTTCGGTCTAG
        ************************************************************

Y-RNA1  GTTTGATGTCTTTAGACATCATGAAGGGCCTTGCGCCGTTCCAGATTCAGGTACGATTAC
D-RNA1  GTTTGATGTCTTTAGACATCATGAAGGGCCTTGCGCCGTTCCAGATTCAGGTACGATTAC
        ************************************************************

Y-RNA1  GGACTTGGAGATGTGGTACGACGCTTTGTTTCCGGGAAATTCGTTAAGAGACTCAAGCCT
D-RNA1  GGACTTGGAGATGTGGTACGACGCTTTGTTTCCGGGAAATTCGTTAAGAGACTCAAGCCT
        ************************************************************
```

Figure 20E

```
Y-RNA1  AGACGGGTATTTGGTGGCAACGACTGATTGCAATTTGCGATTAGACAATGTTACGATCAA
D-RNA1  AGACGGGTATTTGGTGGCAACGACTGATTGCAATTTGCGATTAGACAATGTTACGATCAA
        ************************************************************

Y-RNA1  AAGTGGAAACTGGAAAGACAAGTTTGCTGAAAAGAAACGTTTCTGAAACCGGTTATTCG
D-RNA1  AAGTGGAAACTGGAAAGACAAGTTTGCTGAAAAGAAACGTTTCTGAAACCGGTTATTCG
        ***********************************************************

Y-RNA1  TACTGCTATGCCTGACAAAAGGAAGACTACTCAGTTGGAGAGTTTGTTAGCATTGCAGAA
D-RNA1  TACTGCTATGCCTGACAAAAGGAAGACTACTCAGTTGGAGAGTTTGTTAGCATTGCAGAA
        ************************************************************

Y-RNA1  AAGGAACCAAGCGGCACCCGATCTACAAGAAAATGTGCACGCA_ACAGTTCTAATCGAAGA
D-RNA1  AAGGAACCAAGCGGCACCCGATCTACAAGAAAATGTGCACGCG_ACAGTTCTAATCGAAGA
        ****************************************** ****************

Y-RNA1  GACGATGAAGAAGT_TGAAATCTGTTGTCTACGATGTGGGAAAAATTCGGGCTGATCCTAT
D-RNA1  GACGATGAAGAAGC_TGAAATCTGTTGTCTACGATGTGGGAAAAATTCGGGCTGATCCTAT
        ************* **********************************************

Y-RNA1  TGTCAATAGAGCTCAAATGGAGAGATGGTGGAGAAATCAAAGCACAGCGGTACAGGCTAA
D-RNA1  TGTCAATAGAGCTCAAATGGAGAGATGGTGGAGAAATCAAAGCACAGCGGTACAGGCTAA
        ************************************************************

Y-RNA1  GGTAGTAGCAGATGTGAGAGAGTTACATGAAATAGACTATTCGTCTTACATGTATATGAT
D-RNA1  GGTAGTAGCAGATGTGAGAGAGTTACATGAAATAGACTATTCGTCTTACATGTATATGAT
        ************************************************************

Y-RNA1  CAAATCTGACGTGAAACCTAAGACTGATTTAACACCGCAATTTGAATACTCAGCTCTACA
D-RNA1  CAAATCTGACGTGAAACCTAAGACTGATTTAACACCGCAATTTGAATACTCAGCTCTACA
        ************************************************************

Y-RNA1  GACTGTTGTGTATCACGAGAAGTTGATCAACTCGTTGTTCGGTCCAATTTTCAAAGAAAT
D-RNA1  GACTGTTGTGTATCACGAGAAGTTGATCAACTCGTTGTTCGGTCCAATTTTCAAAGAAAT
        ************************************************************

Y-RNA1  TAATGAACGCAAGTTGGATGCTATGCAACCACATTTTGTGTTCAACACGAGAATGACATC
D-RNA1  TAATGAACGCAAGTTGGATGCTATGCAACCACATTTTGTGTTCAACACGAGAATGACATC
        ************************************************************

Y-RNA1  GAGTGATTTAAACGATCGAGTGAAGTTCTTAAATACGGAAGCGGCTTACGACTTTGTTGA
D-RNA1  GAGTGATTTAAACGATCGAGTGAAGTTCTTAAATACGGAAGCGGCTTACGACTTTGTTGA
        ************************************************************

Y-RNA1  GATAGACATGTCTAAATTCGACAAGTCGGCAAATCGCTTCCATTTACAACTGCAGCTGGA
D-RNA1  GATAGACATGTCTAAATTCGACAAGTCGGCAAATCGCTTCCATTTACAACTGCAGCTGGA
        ************************************************************

Y-RNA1  GATTTACAGGTTATTTGGGCTA_GATGAGTGGGCGGCCTTCCTTTGGGAGGTGTCGCACAC
D-RNA1  GATTTACAGGTTATTTGGGCTG_GATGAGTGGGCGGCCTTCCTTTGGGAGGTGTCGCACAC
        ********************** ************************************
```

Figure 20F

```
     Y-RNA1  TCAAACTACTGTGAGAGATATTCAAAATGGTATGATGGCGCATATTTGGTACCAACAAAA
     D-RNA1  TCAAACTACTGTGAGAGATATTCAAAATGGTATGATGGCGCATATTTGGTACCAACAAAA
             ************************************************************
 5
     Y-RNA1  GAGTGGAGATGCTGATACTTATAATGCAAATTCAGATAGAACACTGTGTGCACTCTTGTC
     D-RNA1  GAGTGGAGATGCTGATACTTATAATGCAAATTCAGATAGAACACTGTGTGCACTCTTGTC
             ************************************************************

10   Y-RNA1  TGAATTACCATTGGAGAAAGCAGTCATGGTTACATATGGAGGAGATGACTCACTGATTGC
     D-RNA1  TGAATTACCATTGGAGAAAGCAGTCATGGTTACATATGGAGGAGATGACTCACTGATTGC
             ************************************************************

Y-RNA1  GTTTCCTAGAGGAACGCAGTTTGTTGATCCGTGTCCAAAGTTGGCTACTAAGTGGAATTT
15   D-RNA1  GTTTCCTAGAGGAACGCAGTTTGTTGATCCGTGTCCAAAGTTGGCTACTAAGTGGAATTT
             ************************************************************

Y-RNA1  CGAGTGCAAGATTTTTAAGTACGATGTCCCAATGTTTTGTGGGAAGTTCTTGCTTAAGAC
     D-RNA1  CGAGTGCAAGATTTTTAAGTACGATGTCCCAATGTTTTGTGGGAAGTTCTTGCTTAAGAC
20           ************************************************************

Y-RNA1  GTCATCGTGTTACGAGTTCGTGCCAGATCCGGTAAAAGTTCTGACGAAGTTGGGGAAAAA
     D-RNA1  GTCATCGTGTTACGAGTTCGTGCCAGATCCGGTAAAAGTTCTGACGAAGTTGGGGAAAAA
             ************************************************************
25
     Y-RNA1  GAGTATAAAGGATGTGCAACATTTAGCCGAGATCTACATCTCGCTGAATGATTCCAATAG
     D-RNA1  GAGTATAAAGGATGTGCAACATTTAGCCGAGATCTACATCTCGCTGAATGATTCCAATAG
             ************************************************************

30   Y-RNA1  AGCTCTTGGGAACTACATGGTGGTATCCAAACTGTCCGAGTCTGTTTCAGACCGGTATTT
     D-RNA1  AGCTCTTGGGAACTACATGGTGGTATCCAAACTGTCCGAGTCTGTTTCAGACCGGTATTT
             ************************************************************

Y-RNA1  GTACAAAGGTGATTCTGTTCATGCGCTTTGTGCGCTATGGAAGCATATTAAGAGTTTTAC
35   D-RNA1  GTACAAAGGTGATTCTGTTCATGCGCTTTGTGCGCTATGGAAGCATATTAAGAGTTTTAC
             ************************************************************

Y-RNA1  AGCTCTGTGTACATTATTCCGAGACGAAAACGATAAGGAATTGAACCCGGCTAAGGTTGA
     D-RNA1  AGCTCTGTGTACATTATTCCGAGACGAAAACGATAAGGAATTGAACCCGGCTAAGGTTGA
40           ************************************************************

Y-RNA1  TTGGAAGAAGGCACAGAGAGCTGTGTCAAACTTTTACGACTGGTAATATGGAAGACAAGT
     D-RNA1  TTGGAAGAAGGCACAGAGAGCTGTGTCAAACTTTTACGACTGGTAATATGGAAGACAAGT
             ************************************************************
45
     Y-RNA1  CATTGGTCACCTTGAAGAAGAAGACTTTCGAAGTCTCAAAATTCTCAAATCTAGGGGCCA
     D-RNA1  CATTGGTCACCTTGAAGAAGAAGACTTTCGAAGTCTCAAAATTCTCAAATCTAGGGGCCA
             ************************************************************

50   Y-RNA1  TTGAATTGTTTGTGGACGGTAGGAGGAAGAGACCGAAGTATTTTCACAGAAGAAGAGAAA
     D-RNA1  TTGAATTGTTTGTGGACGGTAGGAGGAAGAGACCGAAGTATTTTCACAGAAGAAGAGAAA
             ************************************************************
```

Figure 20G

```
Y-RNA1  CTGTCCTAAATCATGTTGGTGGGAAGAAGAGTGAACACAAGTTAGACGTTTTTGACCAAA
D-RNA1  CTGTCCTAAATCATGTTGGTGGGAAGAAGAGTGAACACAAGTTAGACGTTTTTGACCAAA
        ************************************************************

Y-RNA1  GGGATTACAAAATGATTAAATCTTACGCGTTTCTAAAGA_TAGTAGGTGTACAACTAGTTG
D-RNA1  GGGATTACAAAATGATTAAATCTTACGCGTTTCTAAAGG_TAGTAGGTGTACAACTAGTTG
        ************************************** *********************

Y-RNA1  TAACATCACATCTACCTGCAGATACGCCTGGGTTCATTCAAATCGATCTGTTGGATTCGA
D-RNA1  TAACATCACATCTACCTGCAGATACGCCTGGGTTCATTCAAATCGATCTGTTGGATTCGA
        ************************************************************

Y-RNA1  GACTTACTGAGAAAAGAAAGAGAGGAAAGACTATTCAGAGATTCAAAGCTCGAGCTTGCG
D-RNA1  GACTTACTGAGAAAAGAAAGAGAGGAAAGACTATTCAGAGATTCAAAGCTCGAGCTTGCG
        ************************************************************

Y-RNA1  ATAACTGTTCAGTTGCGCAGTACAAGGTTGAATACAGTATTTCCACACAGGAGAACGTAC
D-RNA1  ATAACTGTTCAGTTGCGCAGTACAAGGTTGAATACAGTATTTCCACACAGGAGAACGTAC
        ************************************************************

Y-RNA1  TTGATGTCTGGAAGGTGGGTTGTATTTCTGAGGGCGTTCCGGTCTGTGACGGTACATACC
D-RNA1  TTGATGTCTGGAAGGTGGGTTGTATTTCTGAGGGCGTTCCGGTCTGTGACGGTACATACC
        ************************************************************

Y-RNA1  CTTTCAGTATCGAAGTGTCGCTAATATGGGTTGCTACTGATTCGACTAGGCGCCTCAATG
D-RNA1  CTTTCAGTATCGAAGTGTCGCTAATATGGGTTGCTACTGATTCGACTAGGCGCCTCAATG
        ************************************************************

Y-RNA1  TGGAAGAACTGAACAGTTCGGATTACATTGAAGGCGATTTTACCGATCAAGAGGTTTTCG
D-RNA1  TGGAAGAACTGAACAGTTCGGATTACATTGAAGGCGATTTTACCGATCAAGAGGTTTTCG
        ************************************************************

Y-RNA1  GTGAGTTCATGTCTTTGAAACAAGTGGAGATGAAGACGATTGAGGCGAAGTACGATGGTC
D-RNA1  GTGAGTTCATGTCTTTGAAACAAGTGGAGATGAAGACGATTGAGGCGAAGTACGATGGTC
        ************************************************************

Y-RNA1  CTTACAGACCAGCTACTACTAGACCTAAGTCATTATTGTCAAGTGAAGATGTTAAGAGAG
D-RNA1  CTTACAGACCAGCTACTACTAGACCTAAGTCATTATTGTCAAGTGAAGATGTTAAGAGAG
        ************************************************************

Y-RNA1  CGTCTAATAAGAAAAACTCGTCTTAATGCATAAAGAAATTTATTGTCAATATGACGTGTG
D-RNA1  CGTCTAATAAGAAAAACTCGTCTTAATGCATAAAGAAATTTATTGTCAATATGACGTGTG
        ************************************************************

Y-RNA1  TACTCAAGGGTTGTGTGAATGAAGTCACTGTTCTTGGTCACGAGACGTGTAGTATCGGTC
D-RNA1  TACTCAAGGGTTGTGTGAATGAAGTCACTGTTCTTGGTCACGAGACGTGTAGTATCGGTC
        ************************************************************

Y-RNA1  ATGCTAACAAATTGCGAAAGCAAGTTGCTGACATGGTTGGTGTCACACGTAGGTGTGCGG
D-RNA1  ATGCTAACAAATTGCGAAAGCAAGTTGCTGACATGGTTGGTGTCACACGTAGGTGTGCGG
        ************************************************************
```

Figure 20H

```
     Y-RNA1  AAAATAATTGTGGATGGTTTGTCTGTGTTGTTATCAATGATTTTACTTTTGATGTGTATA
     D-RNA1  AAAATAATTGTGGATGGTTTGTCTGTGTTGTTATCAATGATTTTACTTTTGATGTGTATA
             ************************************************************
5
     Y-RNA1  ATTGTTGTGGCCGTAGTCACCTTGAAAAGTGTCGTAAACGTGTTGAAACAAGAAATCGAG
     D-RNA1  ATTGTTGTGGCCGTAGTCACCTTGAAAAGTGTCGTAAACGTGTTGAAACAAGAAATCGAG
             ************************************************************
10   Y-RNA1  AAATTTGGAAACAAATTCGACGAAATCAAGCTGAAAACATGTCTGCGACAGCTAAAAAGT
     D-RNA1  AAATTTGGAAACAAATTCGACGAAATCAAGCTGAAAACATGTCTGCGACAGCTAAAAAGT
             ************************************************************

Y-RNA1  CTCATAATTCGAAGACCTCTAAGAAGAAATTCAAAGAGGACAGAGAATTTGGGACACCAA
15   D-RNA1  CTCATAATTCGAAGACCTCTAAGAAGAAATTCAAAGAGGACAGAGAATTTGGGACACCAA
             ************************************************************

Y-RNA1  AAAGATTTTTAAGAGATGATGTTCCTTTCGGGATTGATCGTTTGTTTGCTTTTTGATTTT
     D-RNA1  AAAGATTTTTAAGAGATGATGTTCCTTTCGGGATTGATCGTTTGTTTGCTTTTTGATTTT
20           ************************************************************

Y-RNA1  ATTTTATATTGTTATCTGTTTCTGTGTATAGACTGTTTGAGATTGGCGCTTGGCCGACTC
     D-RNA1  ATTTTATATTGTTATCTGTTTCTGTGTATAGACTGTTTGAGATTGGCGCTTGGCCGACTC
             ************************************************************
25
     Y-RNA1  ATTGTCTTACCATAGGGGAACGGACTTTGTTTGTGTTGTTATTTTATTTGTATTTTATTA
     D-RNA1  ATTGTCTTACCATAGGGGAACGGACTTTGTTTGTGTTGTTATTTTATTTGTATTTTATTA
             ************************************************************

30   Y-RNA1  AAATTCTCAATGATCTGAAAAGGCCTCGAGGCTAAGAGATTATTGGGGGGTGAGTAAGTA
     D-RNA1  AAATTCTCAATGATCTGAAAAGGCCTCGAGGCTAAGAGATTATTGGGGGGTGAGTAAGTA
             ************************************************************

Y-RNA1  CTTTTAAAGTGATGATGGTTACAAAGGCAAAAGGGGTAAAACCCCTCGCCTACGTAAGCG
35   D-RNA1  CTTTTAAAGTGATGATGGTTACAAAGGCAAAAGGGGTAAAACCCCTCGCCTACGTAAGCG
             ************************************************************

Y-RNA1  TTATTACGCCC
     D-RNA1  TTATTACGCCC
40           ***********
```

Figure 20I

```
      Y-RNA2    ATAAAACATTGCACCTATGGTGTTGCCCTGGCTGGGGTATGTCAGTGATCGCAGTAGAAT
      D-RNA2    ATAAAACATTGCACCTATGGTGTTGCCCTGGCTGGGGTATGTCAGTGATCGCAGTAGAAT
                ************************************************************

5    Y-RNA2    GTACTAATTGACAAGTTGGAGAATACGGTAGAACGTCCTTATCCAACACAGCCTTTATCC
      D-RNA2    GTACTAATTGACAAGTTGGAGAATACGGTAGAACGTCCTTATCCAACACAGCCTTTATCC
                ************************************************************

Y-RNA2    CTCTCCCTGACGAGGTTTTTGTCAGTGTAATATTTCTTTTTGAACTATCCAGCTTAGTAC
10    D-RNA2    CTCTCCCTGACGAGGTTTTTGTCAGTGTAATATTTCTTTTTGAACTATCCAGCTTAGTAC
                ************************************************************

Y-RNA2    CGTACGGGAAAGTGACTGGTGTGCTTATCTTTGAAATGTTACTTTGGGTTTCGGTTCTTT
      D-RNA2    CGTACGGGAAAGTGACTGGTGTGCTTATCTTTGAAATGTTACTTTGGGTTTCGGTTCTTT
15              ************************************************************

Y-RNA2    AGGTTAGTAAGAAAGCACTTGTCTTCTCATACAAAGGAAAACCTGAG_ACGTATCGCTTAC
      D-RNA2    AGGTTAGTAAGAAAGCACTTGTCTTCTCATACAAAGGAAAACCTG--ACGTATCGCTTAC
                *********************************************   ************
20
      RNA2      GAAAGTAGCAATGAAAGAAAGGTGGTGGTTTTAATCGCTA_CCGCAAAAACGATGGGGTCG
      RNA2      GAAAGTAGCAATGAAAGAAAGGTGGTGGTTTTAATCGTAC_CGCAAAAACGATGGGGTCG
                *************************************  *   ****************

25    Y-RNA2    TTTTAATTAACTTCTCCTACG_CAAGCGTCTAAACGGACGTTGGGGTTTTGCTAGTTTCTT
      D-RNA2    TTTTAATTAACTTCTCCTA--CAAGCGTCTAAACGGACGTTGGGGTTTTGCTAGTTTCTT
                *******************  ***************************************

Y-RNA2    TAGAGAAAACTAGCTAAGTCTTTAATGTTATCATTAGAGATGGCATAAATATAATACTTG
30    D-RNA2    TAGAGAAAACTAGCTAAGTCTTTAATGTTATCATTAGAGATGGCATAAATATAATACTTG
                ************************************************************

Y-RNA2    TGTCTGCTGATAAGATCATTTTAATTTGGACGATTAGACTTGTTGAACTACAGGTTACTG
      D-RNA2    TGTCTGCTGATAAGATCATTTTAATTTGGACGATTAGACTTGTTGAACTACAGGTTACTG
35              ************************************************************

Y-RNA2    AATCACTTGCGCTAATCAACATGGGAGATATGTACGATGAATCATTTGACAAGTCGGGCG
      D-RNA2    AATCACTTGCGCTAATCAACATGGGAGATATGTACGATGAATCATTTGACAAGTCGGGCG
40              ************************************************************

Y-RNA2    GTCCTGCTGACTTGATGGACGATTCTTGGGTGGAATCAGTTTCGTGGAAAGATC_TGTTGA
      D-RNA2    GTCCTGCTGACTTGATGGACGATTCTTGGGTGGAATCAGTTTCGTGGAAAGATT_TGTTGA
                ***************************************************** ******

45    Y-RNA2    AGAAGTTACACAGCATAAAATTTGCACTACAGTCTGGTAGAGATGAGATCACTGGGTTAC
      D-RNA2    AGAAGTTACACAGCATAAAATTTGCACTACAGTCTGGTAGAGATGAGATCACTGGGTTAC
                ************************************************************

Y-RNA2    TAGCGGCACTGAATAGACAGTGTCCTTATTCACCATATGAGCAGTTTCCAGATAAGAAGG
50    D-RNA2    TAGCGGCACTGAATAGACAGTGTCCTTATTCACCATATGAGCAGTTTCCAGATAAGAAGG
                ************************************************************
```

Figure 21A

```
Y-RNA2  TGTATTTCCTTTTAGACTCACGGGCTAACAGTGCTCTTGGTGTGATTCAGAACGCTTCAG
D-RNA2  TGTATTTCCTTTTAGACTCACGGGCTAACAGTGCTCTTGGTGTGATTCAGAACGCTTCAG
        ************************************************************

Y-RNA2  CGTTCAAGAGACGAGCTGATGAGAAGAATGCAGTGGCGGGTGTTACAAATATTCCTGCGA
D-RNA2  CGTTCAAGAGACGAGCTGATGAGAAGAATGCAGTGGCGGGTGTTACAAATATTCCTGCGA
        ************************************************************

Y-RNA2  ATCCAAACACAACGGTTACGACGAACCAAGGGAGTACTACTACTACCAAGGCGAACACTG
D-RNA2  ATCCAAACACAACGGTTACGACGAACCAAGGGAGTACTACTACTACCAAGGCGAACACTG
        ************************************************************

Y-RNA2  GCTCGACTTTGGAAGAAGACTTGTACACTTATTACAAATTCGATGATGCCTCTACAGCTT
D-RNA2  GCTCGACTTTGGAAGAAGACTTGTACACTTATTACAAATTCGATGATGCCTCTACAGCTT
        ************************************************************

Y-RNA2  TCCACAAATCTCTAACTTCGTTAGAGAACATGGAGTTGAAGAGTTATTACCGAAGGAACT
D-RNA2  TCCACAAATCTCTAACTTCGTTAGAGAACATGGAGTTGAAGAGTTATTACCGAAGGAACT
        ************************************************************

Y-RNA2  TTGAGAAAGTATTCGGGATTAAGTTTGGTGGAGCAGCTGCTAGTTCATCTGCACCGCCTC
D-RNA2  TTGAGAAAGTATTCGGGATTAAGTTTGGTGGAGCAGCTGCTAGTTCATCTGCACCGCCTC
        ************************************************************

Y-RNA2  CAGCGAGTGGAGGTCCGATACGTCCTAATCCCTAGGGATTTAAGGACGTGAACTCTGTTG
D-RNA2  CAGCGAGTGGAGGTCCGATACGTCCTAATCCCTAGGGATTTAAGGACGTGAACTCTGTTG
        ************************************************************

Y-RNA2  AGATCTCTGTGAAATTCAGAGGGTGGGTGATACCATATTCACTGATGCCATTAGCGACAT
D-RNA2  AGATCTCTGTGAAATTCAGAGGGTGGGTGATACCATATTCACTGATGCCATTAGCGACAT
        ************************************************************

Y-RNA2  CTAAATAGGGCTAATTGTGACTAATTTGAGGGAATTTCCTTTACCATTGACGTCAGTGTC
D-RNA2  CTAAATAGGGCTAATTGTGACTAATTTGAGGGAATTTCCTTTACCATTGACGTCAGTGTC
        ************************************************************

Y-RNA2  GTTGGTAGCATTTGAGTTTCGCAATGCACGAATTACTTAGGAAGTGGCTTGACGACACTA
D-RNA2  GTTGGTAGCATTTGAGTTTCGCAATGCACGAATTACTTAGGAAGTGGCTTGACGACACTA
        ************************************************************

Y-RNA2  ATGTGTTATTGTTAGATAATGGTTTGGTGGTCAAGGTACGTAGTAGAGTCCCACATATTC
D-RNA2  ATGTGTTATTGTTAGATAATGGTTTGGTGGTCAAGGTACGTAGTAGAGTCCCACATATTC
        ************************************************************

Y-RNA2  GCACGTATGAAGTAATTGGAAAGTTGTCAGTTTTTGATAATTCACTGGGAGATGATACGC
D-RNA2  GCACGTATGAAGTAATTGGAAAGTTGTCAGTTTTTGATAATTCACTGGGAGATGATACGC
        ************************************************************

Y-RNA2  TGTTTGAGGGAAAAGTAGAGAACGTATTTGTTTTTATGTTCAGGCGGTTCTTGTGTGTCA
D-RNA2  TGTTTGAGGGAAAAGTAGAGAACGTATTTGTTTTTATGTTCAGGCGGTTCTTGTGTGTCA
        ************************************************************
```

Figure 21B

```
Y-RNA2  ACAAAGATGGACATTGTTACTCAAGGAAGCACGATGAGCTTTATTATTACGGACGAGTGG
D-RNA2  ACAAAGATGGACATTGTTACTCAAGGAAGCACGATGAGCTTTATTATTACGGACGAGTGG
        ************************************************************

Y-RNA2  ACTTAGATTCTGTGAGTAAATGTCCCGAAGACATTAAACTACGG TTCTTTAAGTAGATCC
D-RNA2  ACTTAGATTCTGTGAGTAAATGTCCCGAAGACATTAAACTACG-TTCTTTAAGTAGATCC
        ******************************************  ***************

Y-RNA2  GTGTCTGAAGTTTTAGGTTCAATTTAAACCTACGAGATTGACATTCTCGACTGATCTTGA
D-RNA2  GTGCCTGAAGTTTTAGGTTCAATTTAAACCTACGAGATTGACATTCTCGACTGATCTTGA
        *** ********************************************************

Y-RNA2  TTGATCGGTAAGTCTTTTGTAATTTAATTTTCTTTTTGATTTTATTTTAAATTGTTATCT
D-RNA2  TTGATCGGTAAGTCTTTTGTAATTTAATTTTCTTTTTGATTTTATTTTAAATTGTTATCT
        ************************************************************

Y-RNA2 GTTTCTGTGTATAGACTGTTTGAGATCGGCGTTTGCC GACTCATTGTCTTACCATAGGG
D-RNA2 GTTTCTGTGTATAGACTGTTTGAGATCGGCGTTTA---GG CTCATTGTCTTACCATAGGG
       **********************************     *  *****************

Y-RNA2  GAACGGACTTTGTTTGTGTTGTTATTTTATTTGTATTTTATTAAAATTCTCAACGATCTG
D-RNA2  GAACGGACTTTGTTTGTGTTGTTATTTTATTTGTATTTTATTAAAATTCTCAACGATCTG
        ************************************************************

Y-RNA2  AAAAGCCTCGCGG CTAAGAGATTGTTGGGGGGTGAGTAAGTACTTTTAAAGTGATGATG
D-RNA2  AAAAGCCTCGCG-CTAAGAGATTGTTGGGGGGTGAGTAAGTACTTTTAAAGTGATGATG
        ************ ***********************************************

Y-RNA2  GTTACAAAGGCAAAAGGGGTAAAACCCCTCGCCTACGTAAGCGTTATTACGCCC
D-RNA2  GTTACAAAGGCAAAAGGGGTAAAACCCCTCGCCTACGTAAGCGTTATTACGCCC
        *****************************************************
```

TOBACCO RATTLE VIRUS VECTORS AND RELATED COMPOSITIONS AND METHODS

RELATED APPLICATION

This application claims the benefit of the filing date of U.S. Provisional Application No. 60/364,901, filed Mar. 14, 2002, entitled "Novel tobacco rattle virus based viral induced gene silencing system", by S. P. Dinesh Kumar, Y. Liu and M. Schiff. The entire teachings of the referenced application are incorporated by reference herein in their entirety.

STATEMENT REGARDING FEDERAL FUNDING

Work described herein was funded, in whole or in part, by National Science Foundation Plant Genome Grant DBI-0077510. The United States government has certain rights in the invention.

BACKGROUND OF THE INVENTION

Aided by high-throughput sequencing technology, plant biologists have identified large numbers of novel open reading frames (ORFs). Large-scale functional genomic approaches are needed in order to convert this sequence information into functional information. Traditionally, *Agrobacterium* Ti plasmid transfer DNA (T-DNA) and transposon-based insertional mutant populations have provided the resources for the analysis of phenotypes. Large collections of such insertion and deletion mutant populations have been generated for plants like *Arabidopsis thaliana* due to the ease of transformation. However, these mutant collections are not generally saturated, meaning that all ORFs have not been disrupted or tagged by an insertion or deletion. Saturation may be difficult to achieve because of bias in the insertion of T-DNA or transposons and because disruptions of essential genes often result in nonviable plants that are lost from the collection. In addition, many plant genomes have a high degree of gene duplication, and therefore a disruption of a gene will not yield any measurable phenotype because a duplicate copy of the gene compensates for the defect. Alternative methods for probing gene function have been developed, including dsRNA-mediated suppression of genes by vectors that produce sense and antisense transcripts. However, all of these approaches rely on the generation of transgenic lines. The generation of transgenic plant lines is a time consuming process, and is only practical for high throughput analyses in *Arabidopsis*.

Gene silencing approaches, such as virus induced gene silencing (VIGS), offer an attractive and quick alternative for knocking out expression of a gene without the need to genetically transform the plant. Using this method, recombinant virus carrying a partial sequence of a host gene is used to infect the plant. When the virus spreads systemically, the endogenous gene transcripts, which are homologous to the insert in the viral vector (VIGS-vector), are degraded by post-transcriptional gene silencing (PTGS). Vectors for carrying out gene silencing suffer from a variety of shortcomings, including inability to silence genes in proliferating or non-proliferating cells, inability to silence genes in a large area of the target plant, and poor rate of infection in target plants.

Improved vectors for use in plants, and particularly vectors for use in gene silencing and high-throughput gene analysis, are needed in the field of plant biology.

SUMMARY OF THE INVENTION

In certain aspects, the invention relates to the discovery of novel RNA1 and RNA2 sequences of tobacco rattle virus (TRV). TRV is a bipartite RNA virus that is useful in transforming plants. Novel RNA1 and RNA2 sequences disclosed herein, and portions thereof, can be used independently to transform plants and plant cells, and have also been incorporated into novel TRV-RNA1 and TRV-RNA2 vectors to achieve particularly efficient transformation of plants. In certain embodiments, the invention provides novel TRV-RNA2 vectors that can be engineered to carry a heterologous nucleic acid for delivery into a plant. The novel TRV RNAs and vectors can be used to achieve, for example, suppression of host plant gene expression or overexpression of the heterologous nucleic acid. In certain embodiments, the invention provides methods for making transgenic plants, as well as the resulting transgenic plants and plant products thereof. In certain embodiments, the invention provides methods for evaluating the function of novel or uncharacterized plant genes, and many of the vectors disclosed herein are particularly suitable for high-throughput analysis of plant gene function.

In certain aspects, the invention provides recombinant nucleic acids comprising a novel TRV-RNA1 nucleotide sequence of SEQ ID NO:1, and complementary sequences thereof. Certain embodiments of the invention also provide TRV-RNA1 nucleic acids that have one or more of the following nucleotides: A at nucleotide 1266, C at nucleotide 2291, T at nucleotide 3094, T at nucleotide 3130, G at nucleotide 3634, A at nucleotide 4123, T at nucleotide 4254, A at nucleotide 4642, and A at nucleotide 5559. The nucleotide positions are given in reference to the sequence of SEQ ID NO:1, but in certain embodiments, the invention also provides variants of the novel TRV-RNA1 nucleotide sequence, including truncations, rearrangements, insertions, deletions, and mutations, so long as one or more of the identified nucleotides is present at a position that discernibly corresponds to the cited position in SEQ ID NO:1. For example, if the sequence of SEQ ID NO:1 is broken into a few pieces that are then reassembled in a different order, one of skill in the art will be able to discern that one or more of the above described nucleotides are still present in the same local sequence context as in SEQ ID NO:1, despite the rearrangement, and accordingly, the rearranged nucleic acid is encompassed by certain embodiments of the present invention. In certain embodiments, the TRV-RNA1 nucleotide sequence is operably linked to a plant active promoter. In certain embodiments, a transcription terminator is positioned within about 10, 100 or 1000 bases downstream of the 3' end of the TRV-RNA1 nucleotide sequence. In certain embodiments, a self-cleaving ribozyme is positioned within about 1, 10 or 100 bases of the 3' end of the TRV-RNA1 nucleotide sequence. In certain embodiments, the TRV-RNA1 nucleic acid is an RNA or a DNA, particularly a cDNA of SEQ ID NO:1. In certain embodiments, the TRV-RNA1 is connected to or contains as an insert a heterologous nucleic acid. Optionally, the heterologous nucleotide sequence includes one or more recombination sites that may be used for the insertion of a nucleic acid of interest (e.g. a nucleic acid to be expressed or a nucleic acid that mediates gene silencing). Examples of recombination sites include a restriction enzyme cleavage site, a multiple cloning site, an integrase recognition site, a transposase recognition site and a recombinase recognition site. In certain embodiments, the heterologous nucleotide sequence causes reduced expression (also referred to as "gene silencing" herein, whether partial or complete reduction of expression of the targeted gene is achieved) of one or more genes of a host plant cell.

In certain aspects, the invention provides TRV-RNA1 vectors comprising a novel TRV-RNA1 sequence of the invention. The vector may be designed, for example, for delivery to a plant by *Agrobacterium*-mediated transformation or microparticle bombardment. In certain embodiments, the TRV-RNA1 nucleic acid is flanked by (meaning positioned between, but not necessarily immediately adjacent to) a T DNA left border sequence and a T DNA right border sequence that mediate transfer into a chromosome of a host plant cell. The vector may be designed for expression of a heterologous gene, in which case it may be desirable to include an additional promoter to drive expression of the heterologous gene. The vector may also be designed for gene silencing. In certain embodiments, the TRV-RNA1 vector is designed for rapid cloning and testing of gene function by gene silencing. Such vectors may include one or more att sites characteristic of a modified phage lambda integrase cloning system, thereby allowing rapid cloning and analysis of a large number of nucleic acids of interest.

In certain aspects, the invention provides recombinant nucleic acids comprising a novel TRV-RNA2 nucleotide sequence of SEQ ID NO:5, and complementary sequences thereof. Certain embodiments of the invention also provide TRV-RNA2 nucleic acids that have one or more of the following nucleotides: base insertions at nucleotides 287, 380, 3490, 3662 and 3756; C at nucleotide 338, T at nucleotide 339, A at nucleotide 340, C at nucleotide 342, G at nucleotide)343, C at nucleotide 344, C at nucleotide 654, T at nucleotide 3509, G at nucleotide 3660. The nucleotide positions are given in reference to the sequence of SEQ ID NO:5, but in certain embodiments, the invention also provides variants of the novel TRV-RNA2 nucleotide sequence, including truncations, rearrangements, insertions, deletions, and mutations, so long as one or more of the identified nucleotides is present at a position that discernibly corresponds to the cited position in SEQ ID NO:5. In certain embodiments, a heterologous nucleic acid is also included in or attached to a TRV-RNA2 recombinant nucleic acid. Optionally, the heterologous nucleotide sequence includes one or more recombination sites that may be used for the insertion of a nucleic acid of interest (e.g. a nucleic acid to be expressed or a nucleic acid that mediates gene silencing). Examples of recombination sites include a restriction enzyme cleavage site, a multiple cloning site, an integrase recognition site, a transposase recognition site and a recombinase recognition site. In certain embodiments, the heterologous nucleotide sequence causes reduced expression (also referred to as "gene silencing" herein, whether partial or complete reduction of expression of the targeted gene is achieved) of one or more genes of a host plant cell. In certain embodiments, the TRV-RNA2 nucleotide sequence is operably linked to a plant active promoter. In certain embodiments, a transcription terminator is positioned within about 10, 100 or 1000 bases downstream of the 3' end of the TRV-RNA2 nucleotide sequence. In certain embodiments, a self-cleaving ribozyme is positioned within about 1, 10 or 100 bases of the 3' end of the TRV-RNA2 nucleotide sequence. In certain embodiments, the TRV-RNA2 nucleic acid is an RNA or a DNA, particularly a cDNA of SEQ ID NO:5.

In certain aspects, the invention provides novel TRV-RNA2 vectors comprising a TRV-RNA2 sequence of the invention. The vector may be designed, for example, for delivery to a plant by *Agrobacterium*-mediated transformation or microparticle bombardment. In certain embodiments, the TRV-RNA2 vector is flanked by a T DNA left border sequence and a T DNA right border sequence. The vector may be designed for expression of a heterologous gene, in which case it may be desirable to include an additional promoter to drive expression of the heterologous gene. The vector may also be designed for gene silencing. In certain embodiments, the TRV-RNA2 vector is designed for rapid cloning and testing of gene function by gene silencing. Such vectors may include one or more att sites characteristic of a modified phage lambda integrase cloning system, thereby allowing rapid cloning and analysis of a large number of nucleic acids of interest.

In certain aspects, the invention provides cells, plants and plant products comprising a TRV-RNA 1 nucleic acid or TRV-RNA2 nucleic acid of the invention. Plants, cells and plant products disclosed herein may also comprise both a TRV-RNA1 nucleic acid and a TRV-RNA2 nucleic acid. In certain embodiments, a cell is bacterial cell. In certain embodiments, a cell is a plant cell. Plants and plant cells may be stably or transiently transformed with one or more TRV-RNA1 or RNA2 replicons. In certain embodiments, the invention provides viruses or viral particles comprising a TRV-RNA1 or TRV-RNA2 nucleic acid of the invention.

In certain aspects, the invention provides methods for making transgenic plants. In certain embodiments, a method of the invention comprises introducing a novel TRV-RNA1 vector into one or more cells of host plant. In certain embodiments, a method of the invention comprises introducing a novel TRV-RNA2 vector into one or more cells of host plant. In certain embodiments, a method of the invention comprises introducing novel TRV-RNA1 and TRV-RNA2 vectors into one or more cells of a host plant. In certain embodiments, a method of the invention comprises introducing a novel TRV-RNA2 vector into one or more cells of a host plant, wherein the host plant is stably transformed with a TRV-RNA1 nucleic acid. Plant that are stably transformed with a TRV-RNA1 (novel or otherwise) are particularly suitable for use in high-throughput screening of TRV-RNA2 vectors containing many different gene silencing inserts. In certain embodiments, a method of the invention comprises introducing a novel TRV-RNA1 vector into one or more cells of a host plant, wherein the host plant is stably transformed with a TRV-RNA2. A TRV-RNA2 replicon is generally quiescent in the absence of a TRV-RNA1, and therefore plants stably transformed with a TRV-RNA2 may be maintained in a quiescent state until activation of the TRV-RNA2 is achieved by introducing the TRV-RNA1. A method may further comprise generating offspring of the initially transformed plant, e.g. by selfing or outcrossing. In certain embodiments, the invention provides methods for introducing a TRV vector into one or more cells of a tomato plant, the method comprising: spraying the tomato plant with a liquid mixture comprising *Agrobacterium* cells containing the TRV vector. In certain embodiments, the invention further provides the transgenic plants produced according to such methods, as well as plant products derived therefrom.

In certain aspects, the invention provides methods for decreasing the expression of a gene in one or more cells of a plant, the method comprising introducing a TRV-RNA2 (or optionally a TRV-RNA1) vector of the invention that includes a gene silencing insert into one or more cells of the plant, wherein expression of the gene silencing insert causes down-regulation of expression of the gene in the plant or portion of the plant. In certain embodiments, the invention provides methods for evaluating the function of a selected gene in a plant, the method comprising: introducing a TRV-RNA2 vector carrying a gene silencing insert into one or more cells of the plant and observing at least one phenotype of the plant. The phenotype may be compared to that of a plant in which the gene silencing insert is not expressed.

The embodiments and practices of the present application, other embodiments, and their features and characteristics, will be apparent from the description, figures and claims that follow.

BRIEF DESCRIPTION OF THE DRAWINGS

FIG. 7. Amino acid comparison of the predicted tobacco EDS1 (tEDS1) protein (SEQ ID NO: 43) with *Arabidopsis* EDS1 (AtEDS1) (SEQ ID NO: 44) (Falk et al., 1999). CLUSTALW produced alignment file was formatted using BOXSHADE program. Identical amino acids are shaded in black and conservative substitutions are shaded in gray. Asterisks (*) indicate the conserved putative lipase catalytic triad consisting of serine (S125), aspartate (D186) and histidine (H322). The eds1-1 mutation (E466K) position in *Arabidopsis* (Falk et al., 1999) is shown in bold italics and underlined.

FIG. 8. Alignment of tobacco NPR1 (tNPR1) (SEQ ID NO: 45) and *Arabidopsis* NPR1/NIM1 (AtNPR1) (SEQ ID NO: 46) (Cao et al., 1997) amino acid sequence. CLUSTALW produced alignment file was formatted using BOXSHADE program. Identical amino acids are shaded in black and conservative substitutions are shaded in gray. Ankyrin repeats are underlined. Asterisks amino acids that affect the function of NPR1 in *Arabidopsis*. Amino acids required for nuclear localization of NPR1 in *Arabidopsis* are shown in italics and double underlined.

FIG. 10. Recombinant TRV infects tomato. (a,b) TRV based VIGS vectors. TRV cDNA clones were placed in between duplicated CaMV 35S promoter (2 3 35S) and nopaline synthase terminator (NOSt) in a T-DNA vector. RdRp, RNA dependent RNA polymerase; 16K, 16 kDa cysteine rich protein; MP, movement protein; CP, coat protein; LB and RB, left and right borders of T-DNA; Rz, self-cleaving ribozyme; MCS, multiple cloning sites. (c) Accumulation of genomic TRV RNA1 (gRNA1) and RNA2 (gRNA2) and subgenomic RNA1a (sgRNA1a) and RNA1b (sgRNA1b) in the systemic leaves of recombinant TRV-infected tomato plants. Tomato plants were infiltrated with *Agrobacterium* alone (lane 1) or *Agrobacterium* containing pTRV1 and pTRV2 (lane 2). Ten days after infiltration, blots were prepared using 5 μg of total RNA and probed with 32P-labeled cDNA fragments corresponding to the 3' ends of RNA1 and RNA2. The picture of the ethidium bromide stained gel shown below the blot demonstrates the equal loading of RNA.

FIG. 11. Method of inoculation of *Agrobacterium*-containing TRV clones onto tomato plants. *Agrobacterium* cultures containing pTRV1 and pTRV2 carrying tomato PDS (pTRV2-tPDS) were mixed in a 1:1 ratio and infiltrated on to 3-week-old tomato plants using 1 ml needleless syringe (a) or sprayed using an artist's airbrush (b). The silencing effect was visible 10 days after *Agrobacterium* infiltration or spray.

FIG. 15. Map of pTRV2 GATEWAY vector and schematic representation of cloning PCR products. (a) Modified pTRV2 vector based on the GATEWAY cloning technology containing attP1 and attP2 recombination sites. (b) PCR products flanked by attB1 and attB2 sites can be directly recombined into attP1 and attP2 containing pTRV2 vector using BP CLONASE enzyme. The resulting attL1- and attL2-containing recombinant clone is shown.

FIG. 16. Schematic representation of cloning tomato ESTs into the pTRV2-attR2-attR1 vector. (a) Modified pTRV2 vector based on the GATEWAY cloning technology containing attR1 and attR2 recombination sites. (b) PCR products flanked by attB1 and attB2 sites can be directly recombined into attP1- and attP2-containing pDONR-mod using BP CLONASE enzyme. The resulting attL1- and attL2-containing pDONR-mod vector can be recombined with pTRV2 containing attR1 and attR2 using LR CLONASE enzyme. The resulting attB1- and attB2-containing recombinant clone is shown. (c) Tomato EST products generated by PCR using a common set primer with attB1 and attB2 sites shown in (b). M, marker; 1-10, different tomato EST PCR products. (d) Restriction digestion of plasmids prepared from two independent colonies recovered from *E. coli* transformed with each recombination reaction mixture containing pTRV2-attR2-attR1 and tomato EST PCR products. Plasmids were cut with XbaI-SacI to release the inserts. Some inserts do not match the PCR product size shown in (c) because of internal restriction sites.

FIGS. 18A-C. A sequence comparison of the amino acid sequence of the 194 kDa TRV-RNA1 replicase disclosed herein (denoted as "Y-POL") (SEQ ID NO: 2) with the sequence as presented in Ratcliff et al. 2001 (denoted as "D-POL") (SEQ ID NO: 47).

FIG. 19. A sequence comparison of the amino acid sequence of the movement protein of TRV-RNA1 disclosed herein (denoted "Y-MP") (SEQ ID NO: 3) with the sequence as presented in Ratcliff et al. 2001 (denoted as "D-MP") (SEQ ID NO: 48).

FIGS. 20A-I. A sequence comparison of the nucleic acid sequence of the TRV-RNA1 sequence disclosed herein (denoted "Y-RNA1") (SEQ ID NO: 3) with the sequence as presented in Ratcliff et al. 2001 (denoted as "D-RNA1") (SEQ ID NO: 49).

FIGS. 21A-C. A sequence comparison of the amino acid sequence of the movement protein of TRV-RNA2 disclosed herein (denoted "Y-RNA2") (SEQ ID NO: 5) with the sequence as presented in Ratcliff et al. 2001 (denoted as "D-RNA2") (SEQ ID NO: 50).

DETAILED DESCRIPTION OF THE INVENTION

1. Tobacco Rattle Virus Vectors

Figure 1:
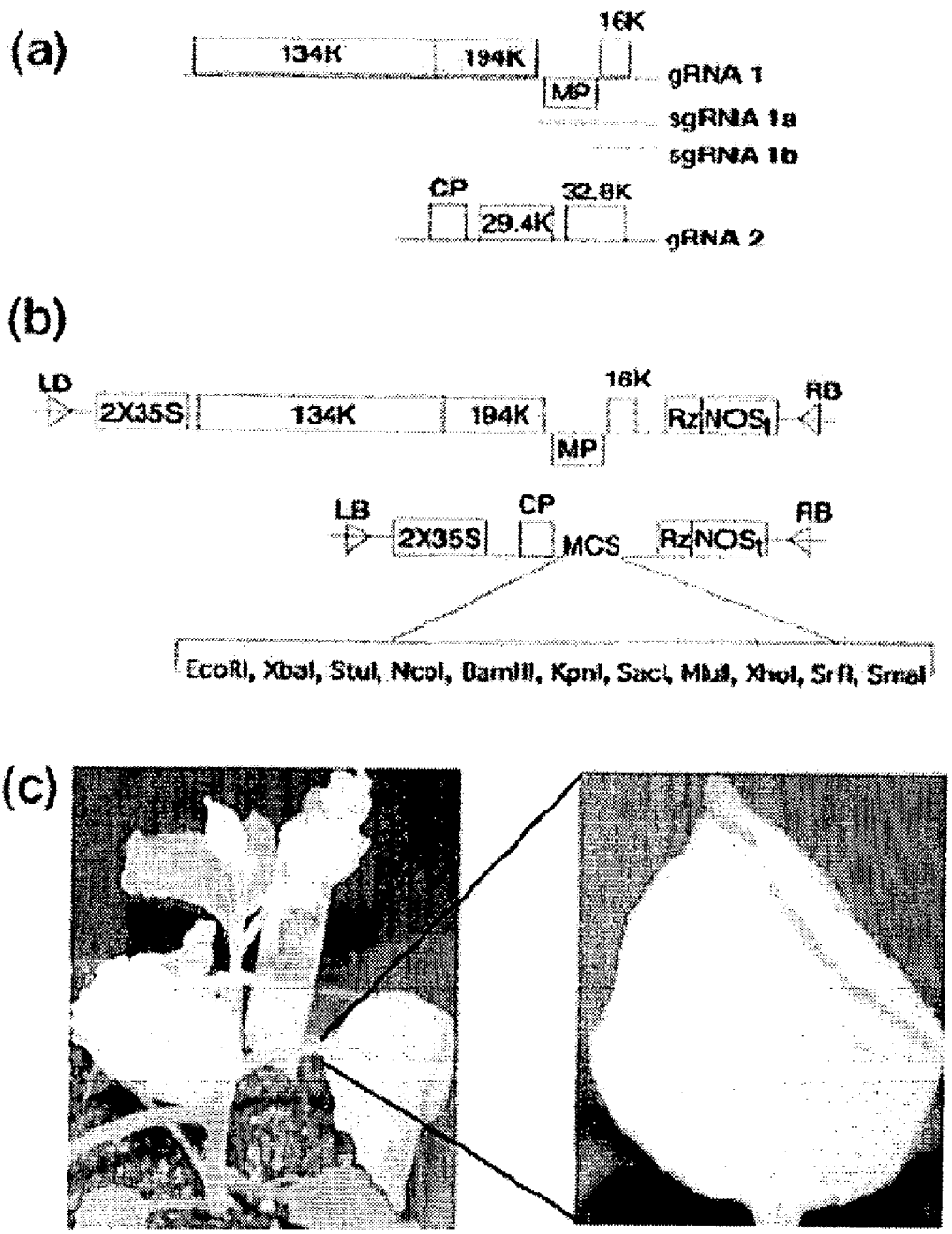
FIG. 1. TRV based VIGS system. (a) Genome organization of TRV. The TRV-RNA1 open reading frames (ORFs) correspond to 134 and 194 kDa replicase, movement protein (MP) and a 16-kDa cysteine-rich protein. The TRV-RNA2 ORFs corresponds to coat protein (CP), and the 29.4 and 32.8 kDa proteins. gRNA, genomic RNA; sgRNA, subgenomic RNA. Asterisks (*) indicate the readthrough of 134 kDa protein. (b) TRV based VIGS vectors. TRV cDNA clones were placed in between the duplicated CaMV 35S promoter (2 3 35S) and the nopaline synthase terminator (NOSt) in a T-DNA vector. LB and RB refer to left and right borders of T-DNA. Rz, self-cleaving ribozyme. MCS, multiple cloning sites. (c) Silencing of the PDS gene. Infection of recombinant TRV carrying the PDS sequence silences endogenous PDS in *N. benthamiana* plants and causes inhibition of carotenoid biosynthesis resulting in the photobleaching phenotype. On the left, whole plant and on the right, enlarged single leaf.

In certain aspects, the invention provides novel tobacco rattle virus (TRV) nucleic acids, and novel vectors based on TRV nucleic acids. TRV is a positive strand RNA virus with a bipartite genome, meaning that the genome is divided into two positive-sense, single-stranded RNAs, that may be separately encapsidated into viral particles. The two TRV genomic RNAs are referred to as TRV-RNA1 and TRV-RNA2. RNA1 encodes polypeptides that mediate replication and movement in the host plant, while RNA2 encodes coat protein. Certain aspects of the invention provide novel TRV-RNA1 or TRV-RNA2 sequences that provide efficient plant transformation capabilities, and TRV-based vectors (termed "TRV vectors") containing such sequences.

A TRV-RNA1 vector, as the term is used herein, is a DNA or RNA vector that comprises a TRV-RNA1 replicon. A TRV-RNA1 replicon is a nucleic acid sequence that may be replicated by the action of a TRV replicase (an RNA polymerase) and comprises a sense or complementary sequence derived from a TRV RNA1. Generally, when introduced into a host plant cell, a TRV-RNA1 vector provides a replicase that mediates replication of the TRV RNA1 replicon, and a movement protein that mediates movement in a host plant. In certain embodiments, a TRV-RNA1 replicon comprises a replication start site, one or more TRV replicases, such as 134 kDa and 194 kDa replicases, a movement protein, and a cysteine-rich protein, such as a TRV 16 kDa cysteine-rich protein. In certain embodiments, one or more RNA1 sequences that are not needed for infection of a desired host plant are deleted in the construction of a TRV-RNA1 replicon.

In certain embodiments, the invention provides novel TRV-RNA1 sequences that may be used for plant transformation directly or may be placed in vector to make a TRV-RNA1 vector. The term "recombinant nucleic acid" includes any nucleic acid comprising at least two sequences which are not present together in nature. A recombinant nucleic acid is also any nucleic acid containing a man-made alteration, such as a nucleotide insertion, deletion or substitution relative to a naturally occurring sequence. A recombinant nucleic acid may be generated in vitro, for example by using the methods of molecular biology, or in vivo, for example by insertion of a nucleic acid at a novel chromosomal location by homologous or non-homologous recombination. An example of a novel TRV-RNA1 sequence is shown in Example 1. This sequence differs from the RNA1 of the TRV Ppk20 isolate at 9 bases (G1266 is changed to A, T2291 is changed to C, C3094 is changed to T, C3130 is changed to T, A3634 is changed to G, G4123 is changed to A, G4254 is changed to T, G4642 is changed to A, G5559 is changed to A). These differences at the nucleotide sequence level give rise to three amino acid changes (S355N and S697P in the replicase ORF; V781 in the 29K movement protein). Any of these nine base changes may be engineered separately or in various combinations into RNA1 sequences. Furthermore, RNA1 sequences may be truncated, rearranged, modified by insertion, deletion or point mutation, or otherwise altered, and yet it will generally be discernable what nucleotide is present at the positions corresponding to the original nucleotide positions 1266, 2291, 3094, 3130, 3634, 4123, 4254, 4642 and 5559. Such variations, and especially those variations that retain replicase and mobility functionalities, are intended to be encompassed herein. A TRV-RNA1 replicon may be designed to include a heterologous sequence, such as a recombination site or a gene silencing insert, as described for RNA2 below. The TRV-RNA1 cDNA of SEQ ID NO:1 is stable at room temperature in E. coli and therefore disruption of the replicase ORF by inclusion of an intron is not required to allow manipulation and maintenance of such TRV-RNA1 vectors in E. coli host cells. However, it is possible to disrupt the TRV-RNA1 sequence with an intron, such as intron 3 of the *Arabidopsis* Col-0 nitrate reductase NIA1 gene (Wilkinson and Crawford, 1993; Ratcliffe et al., 2001), if desired. The intron sequence will generally be removed by the splicing machinery of a host plant cell. In certain embodiments, TRV-RNA1 vectors comprising novel TRV-RNA1 sequences provided herein show improved effectiveness for infection of host plants.

Replicase proteins from TRV and related viruses mediate the replication of RNA molecules. Accordingly, where the TRV vector is a DNA vector, it will generally be desirable to include a plant active promoter situated so as to stimulate transcription of (operably linked to) a TRV-RNA1 or TRV-RNA2 replicon. For example, a plant active promoter may be situated at the 5'-end of a TRV-RNA1 or TRV-RNA2 replicon. The term "plant active promoter" refers to a promoter that functions in a host plant that is infected with the TRV vector. In one embodiment, a plant active promoter is the Cauliflower Mosaic Virus 35S ("CaMV35S") promoter that is expressed at a high level in many plant tissues. Other plant active promoters include the maize glutathione-S-transferase isoform II (GST-II-27) gene promoter (WO93/01294, ICI Ltd), the DEX promoter (Plant Journal (1997) 11: 605-612) and promoters that are transcribed by the TRV replicase, such as subgenomic promoters from related tobraviruses, e.g. pea early browning virus or pepper ringspot virus. In certain embodiments, a TRV-RNA1 or TRV-RNA2 is operably linked to two or more plant active promoters. In certain embodiments, it may be desirable to include an additional plant active promoter to drive additional expression of the coat protein or the heterologous nucleic acid. In certain embodiments, coat protein is expressed from a subgenomic RNA, transcription of which is stimulated by an endogenous TRV subgenomic promoter.

A TRV-RNA2 vector, as the term is used herein, is a DNA or RNA vector that comprises a TRV-RNA2 replicon. A TRV-RNA2 replicon is a nucleic acid sequence that is replicated by the action of a TRV replicase and that comprises a sense or complementary sequence derived from a TRV-RNA2. A TRV-RNA2 replicon will typically include a heterologous sequence. A heterologous sequence is a sequence that is not normally part of an RNA2 of a naturally occurring TRV. In certain embodiments, a heterologous sequence is a recombination site that is designed to facilitate the insertion of a sequence of interest. A recombination site may be, for example, a restriction enzyme (RE) cleavage site, a series of RE cleavage sites, or a recombinase recognition site. Recombination sites are further described below. In certain embodiments, a heterologous sequence is a sequence of interest, such as a gene for expression in a host plant cell or a sequence that causes gene silencing (a gene silencing insert) of one or more genes in a host plant cell. As part of the TRV-RNA2 replicon, the heterologous sequence is positioned relative to RNA2 sequences in such a manner that it is replicated by the replicase. Generally, when introduced into a host plant cell, a TRV-RNA2 vector provides expression of the heterologous sequence and may also provide expression of other RNA2 sequences, such as a viral coat protein. In certain embodiments, a TRV-RNA2 replicon comprises a replication start site, a viral coat protein, such as a TRV viral coat protein and a heterologous sequence. In certain embodiments, one or more RNA2 sequences that are not needed for infection of a desired host plant (e.g. 29.4 kDa and 32.8 kDa non-structural proteins) are deleted in the construction of a TRV-RNA2 replicon.

In certain embodiments, the invention provides novel TRV-RNA2 sequences that may be used in a TRV vector. An example of a novel TRV-RNA2 sequence is shown in Example 2. This sequence differs from TRV-RNA2 sequences of Ppk20 at numerous positions (base insertions at nucleotides 287, 380, 3490, 3662 and 3756; base changes T338C, A339T, C340A, G342C, C343G, A344C, T654C, C3509T, A3660G). Any of these changes may be engineered separately or in various combinations into RNA2 sequences. Furthermore, RNA2 sequences may be truncated, rearranged, modified by insertion, deletion or point mutation, or otherwise altered, and yet it will generally be discernable what nucleotide is present at the positions corresponding to the original nucleotide positions 287, 380, 3490, 3662, 3756, 338, 339, 340, 342, 343, 344, 654, 3509 and 3660 positions. Such variations, and especially those variations that do not disrupt replication and coat protein production are subjects of this invention. In certain embodiments, novel TRV-RNA2 nucleic acids and vectors comprising novel TRV-RNA2 sequences provided herein show improved effectiveness for infection of host plants.

The TRV coat protein may be any naturally occurring TRV coat protein or coat protein from a related virus or variant thereof (e.g. mutant, or other variant, or a substantially homologous derivative) provided that the coat protein retains the ability to encapsulate and permit movement of the TRV genome. Examples of TRV coat protein amino acid and nucleic acid sequences are shown in Example 2. As used herein, the term "substantially homologous" means that the sequence in question shares at least about 70%, or 80% identity, most preferably at least about 90%, 95%, 96%, 97%, 98% or 99% identity with the reference sequence. Identity may be at the nucleotide sequence and/or encoded amino acid sequence level. Homology may be over the full-length of the reference sequence or may be over a functional portion. Identity may be determined by the BLAST program, of Altschul et al. (1990) J. Mol. Biol. 215: 403-10, or BestFit, which is part of the Wisconsin Package, Version 8, September 1994, (Genetics Computer Group, 575 Science Drive, Madison, Wis., USA, Wisconsin 53711). Optionally, sequence comparisons are made using FASTA and FASTP (see Pearson & Lipman, 1988. Methods in Enzymology 183: 63-98). Generally, default parameters should be employed.

Within a TRV replicon, it is preferable that non-essential ORFs or other sequences are not present, provided that the cDNA can still be used to generate replicating, infectious transcripts. Preferably, where the replicon is based on TRV RNA2 of ppk20, two open reading frames (37K and 32.8K) are deleted to leave only the 5' and 3' untranslated regions and the viral gene encoding the coat-protein. The deleted ORFs may be replaced by a heterologous nucleotide sequence between the coat protein and the untranslated region (UTR).

In certain embodiments, a transcriptional terminator may be positioned at the 3'-end of an RNA transcript to limit readthrough of the transcript. For example, a transcriptional terminator may be positioned at the 3'-end of a TRV-RNA1 or TRV-RNA2 replicon. A commonly used plant transcriptional terminator is a nopaline synthase terminator (NOSt).

In certain embodiments, it may be desirable to generate a precise 3' end of an RNA transcript. This can be achieved, for example, by including a ribozyme sequence at the 3' end that will mediate autocleavage at the 3' end of the RNA at a defined site. A ribozyme may be positioned close to what would be the natural end point of a TRV RNA1 or RNA2 sequence so that the replicon will contain few, if any, non-TRV nucleotides at the 3' end. An example of a ribozyme is described in Turpen et al, 1993.

Recombination sites for replicons and vectors are well known in the art and include, for example, restriction sites, topoisomerase sites, recombinase sites, integrase sites and transposase sites. Restriction sites may be placed in adjacent or overlapping positions to form a "multiple cloning site" or MCS. As another example, the GATEWAY Cloning Technology (Invitrogen Corp., Carlsbad, Calif.) uses a modified version of a site-specific recombination system used by phage lambda to integrate its DNA into the *E. coli* chromosome. Phage lambda has specific recombination sites called attP, and *E. coli* has a specific recombination site called attB. Phage lambda integration is catalyzed by two enzymes: the phage lambda protein Int (Integrase) and the *E. coli* protein IHF (Integration Host Factor). Upon integration, the recombination between attB (25 nt) and attP (243 nt) sites generate attL (100 nt) and attR (168 nt) sites that flank the integrated phage lambda DNA. The process is reversible and excision is catalyzed by Int and IHF in combination with the phage lambda protein Xis. The attL and attR sites surrounding the inserted phage DNA recombine site-specifically during the excision event to reform the attP site in phage 1 and the attB site in the *E. coli* chromosome. In the GATEWAY system, a vector such as a pTRV2 vector, is engineered to have attR1 and attR2 sites flanking the position at which the desired insert (e.g. heterologous nucleic acid for gene silencing) is to be inserted. The insert is prepared so as to have attB 1 and attB2 sites, and the insert is then recombined with the attR1 and attR2 sites. Often a selectable marker, such as an antibiotic resistance cassette or a positive selection marker such as the ccdB gene is present between the attR insertion sites to allow selection of successful recombinants.

Accordingly, a heterologous nucleic acid in a TRV-RNA2 or TRV-RNA1 nucleic acid may include one or more att sites and may also include one or more selectable markers between the att sites.

Other examples of recombination sites for inclusion in replicons and vectors include the Cre-lox recombinase system such as is used in the Creator™ Gene Cloning & Expression System (BD Biosciences Clontech, Palo Alto, Calif.) and the TOPO® cloning systems (Invitrogen Corp., Carlsbad, Calif.) that employ topoisomerase I-mediated cloning.

An example of a TRV-RNA1 replicon comprises a replication start site, a coding sequence for a 134 kDa replicase and 194 kDa replicase (often overlapping, where an optional stop codon determines which protein is produced), a coding sequence for a movement protein, a coding sequence for a 16 kDa cysteine-rich protein and a transcriptional terminator, such as a NOSt. The TRV-RNA1 sequences contain one or more of the following differences from the Ppk20 RNA1: G1266A, T2291C, C3094T, C3130T, A3634G G4123A, G4254T, G4642A, G5559A. Optionally, a self-cleaving ribozyme is positioned 5' to the NOSt. In this example, the TRV-RNA1 replicon is operably linked to one, or optionally two plant active promoters, such as CaMV 35S promoters. The replicon may be a DNA molecule that is transcribed to produce RNA which is a substrate for the TRV replicase, or the replicon may be an RNA. If the replicon is delivered to a plant cell as part of a DNA vector, the plant active promoter will generally drive synthesis of an RNA strand that is then replicated and spread through the plant by the action of the TRV proteins. An example of a TRV-RNA1 replicon sequence is shown in SEQ ID NO:1.

In an exemplary embodiment, a TRV-RNA2 replicon comprises a replication start site, a coding sequence for a TRV coat protein, a heterologous sequence and a transcriptional terminator, such as a NOSt. The TRV-RNA2 sequences contain one or more of the following differences from the Ppk20 RNA2: base insertions at nucleotides 287, 380, 3490, 3662 and 3756; base changes T338C, A339T, C340A, G342C, C343G, A344C, T654C, C3509T, A3660G. In an "empty" vector, the heterologous sequence includes a recombination site (optionally including multiple recombination sites and selectable marker genes, as in the case of many GATEWAY-derived vectors). For a traditional cloning vector, the recombination site is an RE cleavage site, such as an EcoRI, BamHI, SmaI or NotI sequence that allows cleavage with an RE and insertion of a nucleic acid sequence of interest. In a "filled" vector, a nucleic acid of interest has been inserted, and the heterologous sequence comprises the nucleic acid of interest. Depending on the recombination site, there may also be remnants of the recombination site flanking one or both sides of the nucleic acid of interest. The heterologous nucleic acid sequence may be positioned between the coat protein coding sequence and the 3' UTR portions of the TRV-RNA2, or at essentially any location that does not interfere with other replicon functionalities. In this example, the TRV-RNA2 replicon is operably linked to one, or optionally two, plant active promoters, such as CaMV35S promoters. If the replicon is delivered to a plant cell as part of a DNA vector, the plant active promoter will generally drive synthesis of an RNA strand that is then replicated and spread through the plant by the action of the TRV proteins. An example of a TRV-RNA2 replicon sequence is shown in SEQ ID NO:5.

In certain embodiments, a TRV-RNA1 or TRV-RNA2 replicon is a component of a vector. Generally a vector is a nucleic acid construct that is designed to facilitate propagation and introduction into a host cell. In certain embodiments, the vector is a DNA vector designed for use with *Agrobacterium*-mediated transformation and contains T DNA sequences flanking the TRV-RNA1 or TRV-RNA2 replicon. The flanking T DNA sequences mediate insertion of the replicon into the genome of a host plant cell. Vectors for use with *Agrobacterium* are referred to as binary transformation vectors, and many are known in the art, such as pGreen (Ratcliff et al.) or pCASS2 (Shi et al., 1997). In certain embodiments, a vector is designed to be maintained in *E. coli*, and such a vector will generally include an *E. coli* origin of replication and a selectable marker, such as an antibiotic resistance gene. In certain embodiments, a vector may include a plant selectable marker. A vector may also be designed, for example, for introduction by particle bombardment, e.g. by using a gun equipped to deliver tungsten microparticles coated with vector or by exposing cells to silicon whiskers. See, e.g. Taylor and Fauquet, 2002, DNA and Cell Biology 21:963-77. In the case of such delivery systems, the vector may be RNA or DNA and need not contain any specific sequences to facilitate transfer to a plant chromosome.

For TRV-RNA2 vectors designed to provide expression of a protein of interest in a host plant cells, the heterologous sequence encoding the protein of interest may include or be operably linked to a plant active promoter, such as a CaMV 35S promoter or a viral promoter that is recognized by a TRV replicase, such as a promoter from a related virus (e.g. the Pea Early Browning Virus Coat Protein subgenomic promoter).

For TRV-RNA2 vectors designed as gene silencing vectors the heterologous sequence will be a "targeting sequence" which corresponds to a sequence in a target gene, either in the sense or anti-sense orientation, or a sequence which has sufficient homology to a target sequence for down-regulation of expression of the target gene to occur. Such a targeting sequence may be included in the vector anywhere in the TRV-RNA2 replicon irrespective of the location of any promoter (provided it does not interfere with the replicative functions of the TRV-RNA2 replicon). A targeting sequence may, for example, be derived from a plant nuclear gene or transgene, or a gene on an extrachromosomal element such as a plastid.

The complete sequence corresponding to the coding sequence (in reverse orientation for anti-sense) need not be used. For example fragments of sufficient length may be used. It is a routine matter for the person skilled in the art to screen fragments of various sizes and from various parts of the coding sequence to optimize the relationship between target and targeting sequence. It may be preferable that there is complete sequence identity between the targeting sequence in the vector and the target sequence in the plant, although total complementarity or similarity of sequence is not essential. One or more nucleotides may differ in the targeting sequence from the target gene. Thus, a targeting sequence employed in a construct in accordance with the present invention may be a wild-type sequence (e.g. gene) selected from those available, or a substantially homologous mutant, derivative, variant or allele, by way of insertion, addition, deletion or substitution of one or more nucleotides, of such a sequence. Such a sequence need not include an open reading frame or specify an RNA that would be translatable.

A further possibility is to target a conserved sequence of a gene, e.g. a sequence that is characteristic of one or more genes in one or more pathogens against which resistance is desired, such as a regulatory sequence.

Generally speaking, in the light of the present disclosure, those skilled in the art will be able to construct vectors according to the present invention. For further details see, for example, Molecular Cloning: a Laboratory Manual: 2nd edition, Sambrook et al, 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Protocols in Molecular Biology, Second Edition, Ausubel et al. eds., John Wiley & Sons, 1992. Specific procedures and vectors previously used with wide success upon plants are described by Bevan, Nucl. Acids Res. (1984) 12, 8711-8721), and Guerineau and Mullineaux, (1993) Plant transformation and expression vectors. In: Plant Molecular Biology Labfax (Croy RRD ed) Oxford, BIOS Scientific Publishers, pp 121-148.

A TRV-RNA1 vector of the invention may be used to transform plants in combination with a TRV-RNA2 vector of the invention or with another TRV-RNA2 vector or construct that provides similar functionality. Likewise, a TRV-RNA2 vector of the invention may be used to transform plants in combination with a TRV-RNA2 vector of the invention or with another TRV-RNA2 vector or construct that provides similar functionality. Examples of other TRV-RNA1 and RNA2 vectors may be found, for example, in Ratcliff et al., 2001 and Hernandez et al., 1997.

In certain embodiments, the invention provides cells comprising a TRV-RNA1 or TRV-RNA2 vector of the invention. A cell may be a bacterial cell, such as an *E. coli* cell or an *Agrobacterium tumefaciens* cell. A cell comprising a TRV-RNA1 or TRV-RNA2 vector may also be a plant cell. In certain embodiments, the invention provides a plant cell comprising both a TRV-RNA1 vector and a TRV-RNA2 vector. In many instances, a vector is not itself retained in a cell, but the replicon portion is retained, and accordingly in certain embodiments, the invention provides a plant cell comprising a TRV-RNA1 replicon and a TRV-RNA2 replicon. Plant cells of the invention may be in culture, as in the case of cell suspensions or cells in the process of forming callus. Plant cells may also be situated in a living or dead plant or in a plant product.

In a further embodiment, the present invention provides a virus or viral particle including, preferably encapsulating, a TRV-RNA1 and/or TRV-RNA2 replicon of the invention.

2. Transgenic Plants and Plant Products

In certain embodiments, the invention provides methods for making a transgenic plant, and the invention provides the resulting transgenic plants, descendants thereof, and plant products derived from such transgenic plants. The term "transgenic plant" is used to refer to a plant comprising, in one or more of its cells, an exogenous nucleic acid. Accordingly, the term "transgenic plant" is intended to include both transiently and stably transformed plants, as well as plants carrying integrated or non-integrated exogenous nucleic acids.

In general, a method for making a transgenic plant comprises introducing a TRV-RNA1 nucleic acid, replicon or vector, and/or a TRV-RNA2 nucleic acid, replicon or vector into one or more cells of a host plant. Because of the bipartite nature of TRV vectors, both a TRV-RNA1 and TRV-RNA2 will generally be introduced into one or more cells of a host plant, although a host plant may already contain one or the other of a TRV-RNA1 or TRV-RNA2. Introduction of TRV RNA1 and RNA2 nucleic acids may be done simultaneously or at different times. In certain embodiments, the TRV-RNA1 nucleic acid is a nucleic acid of the invention, and particularly a novel nucleic acid providing improved transformation efficiency. In certain embodiments, the TRV-RNA2 nucleic acid is a nucleic acid of the invention, and particularly a novel nucleic acid providing improved transformation efficiency. In certain embodiments, both the TRV-RNA1 and TRV-RNA2 nucleic acids are vectors of the invention. In many embodiments, the TRV-RNA1 and TRV-RNA2 replicons mediate the production of viral particles and movement of these particles to many different cell types of the host plant.

The method for introducing the vectors into the host plant may be selected depending on the type of vector. In the case of vectors for *Agrobacterium*-mediated delivery, the plant will be contacted with an *Agrobacterium* culture comprising a TRV-RNA1 vector and an *Agrobacterium* culture comprising a TRV-RNA2 vector. *Agrobacterium* may be introduced into a plant by a variety of ways, including infiltration, by contacting with a damaged plant portion (e.g. a leaf disc) or by spraying. As disclosed herein, spraying the mixed *Agrobacterium* cultures on the plant is particularly effective for obtaining high infection levels in tomato plants (plants of the genus *Lycopersicon*).

As noted above, particle bombardment systems may also be used to introduce TRV-RNA1 or TRV-RNA2 vectors into plants. In certain embodiments, infectious TRV-RNA1 replicons can be initiated by rub-inoculating the plant with purified RNA 1 (Matthews 1991).

TRV-RNA1 and TRV-RNA2 vectors of the invention may particularly be applied in plants that are naturally infected by TRV, including both monocots and dicots. These include, for example, plants of the genus *Nicotiana* (e.g. tabacum or benthamiana), plants of the genus *Lycopersicon* (e.g. esculentum) and plants of the genus *Arabidopsis* (e.g. thaliana). Others include (but are not limited to) *Allium cepa; Amaranthus caudatus; Amaranthus retroflexus; Antirrhinum majus;* snap-dragon; *Arachis hypogaea; Avena sativa; Bellis perennis; Beta vulgaris; Brassica campestris; Brassica campestris* ssp. napus; *Brassica campestris* ssp. pekinensis; *Brassica juncea; Calendula officinalis; Capsella bursa-pastoris; Capsicum annuum; Catharanthus roseus; Cheiranthus cheiri; Chenopodium album; Chenopodium amaranticolor; Chenopodium foetidum; Chenopodium quinoa; Coriandrum sativum; Cucumis melo; Cucumis sativus; Glycine max; Gomphrena globosa; Gypsophila elegans; Helianthus annuus; Hyacinthus; Hyoscyamus niger; Lactuca sativa; Lathyrus odoratus; Linum usitatissimum; Lobelia erinus; Lupinus mutabilis; Lycopersicon pimpinellifolium; Melilotus albus; Momordica balsamina; Myosotis sylvatica; Narcissus pseudonarcissus; Nicandra physalodes; Nicotiana clevelandii; Nicotiana glutinosa; Nicotiana rustica; Nicotiana sylvestris; Nicotiana edwardsonii; Ocimum basilicum; Petunia hybrida; Phaseolus vulgaris; Phytolacca americana; Pisum sativum; Raphanus sativus; Ricinus communis; Salvia splendens; Senecio vulgaris; Solanum melongena; Solanum nigrum; Solanum tuberosum; Spinacia oleracea; Stellaria media; Trifolium pratense; Trifolium repens; Tropaeolum majus; Tulipa; Vicia faba; Vicia villosa; Viola arvensis*. Other plants that may be infected include *Zea maize, Hordeum vulgare, Triticum aestivum* and *Oryza sativa*.

In those cases in which a stably transformed plant is generated, the plant may be bred so as to produce offspring that are homozygous or heterozygous for the inserted DNA. Many plants may be selfed, but plants may also be outcrossed to generate offspring with different genetic backgrounds. Therefore, in certain embodiments, the invention provides methods for making transgenic plants that involve first making a transformant that contains one or both of a TRV-RNA1 replicon and a TRV-RNA2 replicon, and then breeding or otherwise propagating the transformed plant to obtain transgenic offspring.

In certain embodiments, the invention also provides plant products obtained from transgenic plants of the invention. The term "plant product" is intended to include anything that may be obtained from a particular plant, including, for example, fruits, seeds, pollen, ovules, plant embryos, oils, juices, waxes, proteins, lipids, fatty acids, vitamins, plant tissues in whole or in part, (e.g. roots, leaves, stems, flowers, bark), cells, cell suspensions, tubers and stolons.

3. Certain Methods Employing TRV Nucleic Acids

In certain aspects, the invention provides methods for causing decreased expression of one or more target genes by introducing into one or more cells of a plant, plant tissue or cell culture, a TRV-RNA2 replicon or vector comprising a heterologous nucleic acid for silencing a target gene or genes. Optionally, a TRV-RNA1 replicon or vector, such as a TRV-RNA1 replicon or vector disclosed herein, may also be introduced. Optionally, a TRV-RNA1 replicon or vector containing a gene silencing insert may be introduced.

In certain embodiments, the target gene or genes are pre-selected, and the heterologous nucleic acid is designed to specifically achieve partial or complete silencing of the target gene or genes. The target gene may have an unknown function or unknown loss of function phenotype, in which case a gene silencing method of the invention may be employed to analyze the phenotype by generating a partial or complete loss of function phenotype in a host plant, plant part, or in cells in culture or in a tissue sample. Generally analysis of a phenotype will include a comparison with a plant wherein the target gene is expressed normally. In certain embodiments, the target gene is obtained from a library, such as a cDNA library, or other complex pool of nucleic acids. For example, heterologous nucleic acids of suitable size for gene silencing may be obtained at random from a cDNA library and inserted into a TRV-RNA2 vector for introduction into a host plant. Each host plant that is transformed with a different TRV-RNA2 silencing construct is analyzed for one or more phenotypic characteristics, and constructs that cause a phenotype of interest may be sequenced to determine the identity of the silenced gene. As will be apparent to one of ordinary skill in the art, such methods are amenable to high throughput analysis.

In certain embodiments, the TRV-RNA2 (or TRV-RNA1) vector comprises a system of recombination sites that renders the vector particularly amenable to high throughput cloning of heterologous nucleic acids designed for suppression of gene expression. An example of such a vector is the pTRV2-attR1-attR2 vector described in Example 4, below.

In certain embodiments, the invention not only provides transient transformation assay methods to study gene function. In certain embodiments, a vector is a T7 based vector, and the vector is used in vitro to drive expression of in vitro TRV-RNA1 or RNA2 transcripts that may then be used to infect plants. Optionally one or more of the transcripts contains a gene silencing insert for use in altering expression of a host plant gene.

In certain embodiments, a plant with a stable TRV-RNA1 transformation is provided. The stably transformed plant can then be infiltrated with a TRV-RNA2 nucleic acid, containing, for example, a gene silencing insert to obtain efficient silencing. Such a system is amenable to rapid analysis of gene function. One can grow TRV-RNA2 constructs with many different inserts (e.g. inserts from a cDNA library) on plates and use a simple transient transformation method (such as a tooth pick to prick the leaves) to introduce the constructs into the TRV-RNA1 transgenic plant to induce silencing. The phenotype resulting from silencing may be observed in the local area at which the RNA2 construct was introduced.

In certain embodiments, once a candidate gene has been identified by, for example, a gene silencing approach, transgenic plants or cells may be generated using a different (non-TRV) approach, for example by introducing a dsDNA antisense construct wherein the antisense nucleic acid is expressed from a strong promoter such as a CaMV35S promoter, or, if desired, from a tissue specific or conditional promoter.

Target genes of particular interest include those that are involved in pathogen resistance or susceptibility, such as genes involved in resistance to viral infections.

In certain embodiments, a heterologous nucleic acid may be expressed in a plant or plant cells using a TRV-RNA2 vector designed for expression. Optionally, a TRV-RNA1 vector, such as a TRV-RNA1 vector disclosed herein, may also be introduced.

Figure 6:
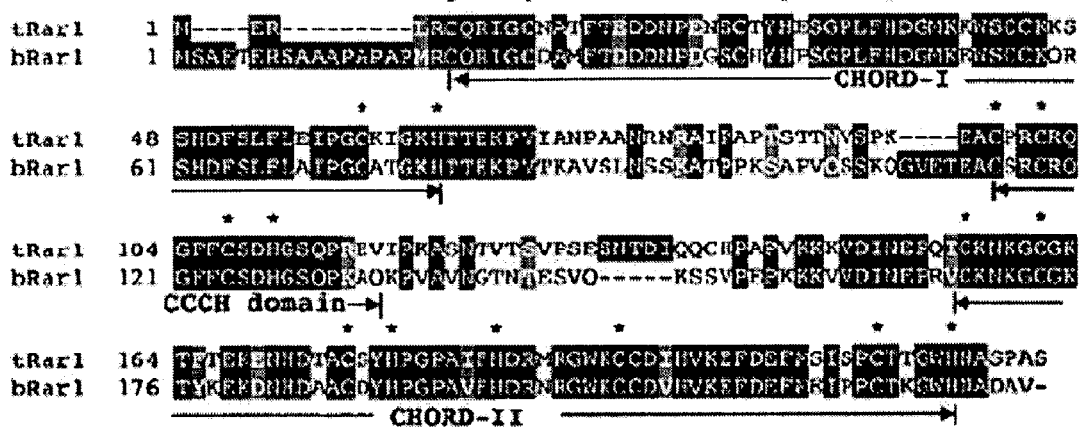
FIG. 6. Amino acid sequence comparison of the predicted tobacco Rar1 (tRar1) protein (SEQ ID NO: 41) with the barley Rar1 (bRar1) (SEQ ID NO: 42) (Shirasu et al., 1999). CLUSTALW produced alignment file was formatted using BOXSHADE program publicly accessible on the Internet. Identical amino acids are shaded in black and conservative substitutions are shaded in gray. Two conserved CHORD domains (CHORD-I and II) and one conserved CCCH domain are shown. Asterisks (*) indicate invariant conserved cystein and histidine residues within the CHORD and CCCH domains.

As described in Example 3, the invention relates in part to the discovery of certain nucleic acids involved in resistance to viral infection. Such nucleic acids include tobacco Rar1, EDS1 and NPR1/NIM1 genes. Accordingly, increased expression of a Rar1, EDS1 or NPR1/NIM1 gene may be used to confer increased resistance to a viral infection, particularly a tobamovirus infection, such as a tobacco mosaic virus. Conversely, if increased susceptibility or decreased plant responsiveness is desired, Rar1, EDS1 or NPR1/NIM1 gene expression may be decreased. Examples of Rar1 amino acid sequences from tobacco and barley are shown in FIG. 6. Examples of EDS1 amino acid sequences from tobacco and *Arabidopsis* are shown in FIG. 7 Examples of NPR1/NIM1 amino acid sequences from tobacco and *Arabidopsis* are shown in FIG. 8.

EXAMPLES

The invention will be more readily understood by reference to the following examples, which are included merely for purposes of illustration of certain aspects and embodiments of the present application, and are not intended to limit the scope of the invention.

Example 1

Certain TRV-RNA1 Sequences

The following is an example of a TRV-RNA1 sequence containing nucleotides at particular positions (bolded in the sequence below) and providing improved plant transformation. The polymerase (134 kDa and 194 kDa together) open reading frame is underlined. The movement protein open reading frame is underlined in bold. The 16 kDa protein is double underlined.

```
                                                                    (SEQ ID NO:1)
            ATAAAACATTTCAATCCTTTGAACGCGGTAGAACGTGCTAATTGGATTTTGGTGAGAACG        60

CGGTAGAACGTACTTATCACCTACAGTTTTATTTTGTTTTTCTTTTTGGTTTAATCTATC       120

CAGCTTAGTACCGAGTGGGGGAAAGTGACTGGTGTGCCTAAAACCTTTTCTTTGATACTT       180

TGTAAAAATACATACAGATACAATGGCGAACGGTAACTTCAAGTTGTCTCAATTGCTCAA       240

TGTGGACGAGATGTCTGCTGAGCAGAGGAGTCATTTCTTTGACTTGATGCTGACTAAACC       300

TGATTGTGAGATCGGGCAAATGATGCAAAGAGTTGTTGTTGATAAAGTCGATGACATGAT       360

TAGAGAAAGAAAGACTAAAGATCCAGTGATTGTTCATGAAGTTCTTTCTCAGAAGGAACA       420

GAACAAGTTGATGGAAATTTATCCTGAATTCAATATCGTGTTTAAAGACGACAAAAACAT       480
```

-continued

| | |
|---|---|
| GGTTCATGGGTTTGCGGCTGCTGAGCGAAAACTACAAGCTTTATTGCTTTTAGATAGAGT | 540 |
| TCCTGCTCTGCAAGAGGTGGATGACATCGGTGGTCAATGGTCGTTTTGGGTAACTAGAGG | 600 |
| TGAGAAAAGGATTCATTCCTGTTGTCCAAATCTAGATATTCGGGATGATCAGAGAGAAAT | 660 |
| TTCTCGACAGATATTTCTTACTGCTATTGGTGATCAAGCTAGAAGTGGTAAGAGACAGAT | 720 |
| GTCGGAGAATGAGCTGTGGATGTATGACCAATTTCGTGAAAATATTGCTGCGCCTAACGC | 780 |
| GGTTAGGTGCAATAATACATATCAGGGTTGTACATGTAGGGGTTTTTCTGATGGTAAGAA | 840 |
| GAAAGGCGCGCAGTATGCGATAGCTCTTCACAGCCTGTATGACTTCAAGTTGAAAGACTT | 900 |
| GATGGCTACTATGGTTGAGAAGAAAACTAAAGTGGTTCATGCTGCTATGCTTTTTGCTCC | 960 |
| TGAAAGTATGTTAGTGGACGAAGGTCCATTACCTTCTGTTGACGGTTACTACATGAAGAA | 1020 |
| GAACGGGAAGATCTATTTCGGTTTTGAGAAAGATCCTTCCTTTTCTTACATTCATGACTG | 1080 |
| GGAAGAGTACAAGAAGTATCTACTGGGGAAGCCAGTGAGTTACCAAGGGAATGTGTTCTA | 1140 |
| CTTCGAACCGTGGCAGGTGAGAGGAGACACAATGCTTTTTCGATCTACAGGATAGCTGG | 1200 |
| AGTTCCGAGGAGGTCTCTATCATCGCAAGAGTACTACCGAAGAATATATATCAGTAGATG | 1260 |
| GGAAAACATGGTTGTTGTCCCAATTTTCGATCTGGTCGAATCAACGCGAGAGTTGGTCAA | 1320 |
| GAAAGACCTGTTTGTAGAGAAACAATTCATGGACAAGTGTTTGGATTACATAGCTAGGTT | 1380 |
| ATCTGACCAGCAGCTGACCATAAGCAATGTTAAATCATACTTGAGTTCAAATAATTGGGT | 1440 |
| CTTATTCATAAACGGGCGGCCGTGAAGAACAAGCAAAGTGTAGATTCTCGAGATTTACA | 1500 |
| GTTGTTGGCTCAAACTTTGCTAGTGAAGGAACAAGTGGCGAGACCTGTCATGAGGGAGTT | 1560 |
| GCGTGAAGCAATTCTGACTGAGACGAAACCTATCACGTCATTGACTGATGTGCTGGGTTT | 1620 |
| AATATCAAGAAAACTGTGGAAGCAGTTTGCTAACAAGATCGCAGTCGGCGGATTCGTTGG | 1680 |
| CATGGTTGGTACTCTAATTGGATTCTATCCAAAGAAGGTACTAACCTGGGCGAAGGACAC | 1740 |
| ACCAAATGGTCCAGAACTATGTTACGAGAACTCGCACAAAACCAAGGTGATAGTATTTCT | 1800 |
| GAGTGTTGTGTATGCCATTGGAGGAATCACGCTTATGCGTCGAGACATCCGAGATGGACT | 1860 |
| GGTGAAAAAACTATGTGATATGTTTGATATCAAACGGGGGCCCATGTCTTAGACGTTGA | 1920 |
| GAATCCGTGCCGCTATTATGAAATCAACGATTTCTTTAGCAGTCTGTATTCGGCATCTGA | 1980 |
| GTCCGGTGAGACCGTTTTACCAGATTTATCCGAGGTAAAAGCCAAGTCTGATAAGCTATT | 2040 |
| GCAGCAGAAGAAAGAAATCGCTGACGAGTTTCTAAGTGCAAAATTCTCTAACTATTCTGG | 2100 |
| CAGTTCGGTGAGAACTTCTCCACCATCGGTGGTCGGTTCATCTCGAAGCGGACTGGGTCT | 2160 |
| GTTGTTGGAAGACAGTAACGTGCTGACCCAAGCTAGAGTTGGAGTTTCAAGAAAGGTAGA | 2220 |
| CGATGAGGAGATCATGGAGCAGTTTCTGAGTGGTCTTATTGACACTGAAGCAGAAATTGA | 2280 |
| CGAGGTTGTTCCAGCCTTTTCAGCTGAATGTGAAAGAGGGGAAACAAGCGGTACAAAGGT | 2340 |
| GTTGTGTAAACCTTTAACGCCACCAGGATTTGAGAACGTGTTGCCAGCTGTCAAACCTTT | 2400 |
| GGTCAGCAAAGGAAAAACGGTCAAACGTGTCGATTACTTCCAAGTGATGGGAGGTGAGAG | 2460 |
| ATTACCAAAAAGGCCGGTTGTCAGTGGAGACGATTCTGTGGACGCTAGAAGAGAGTTTCT | 2520 |
| GTACTACTTAGATGCGGAGAGAGTCGCTCAAAATGATGAAATTATGTCTCTGTATCGTGA | 2580 |
| CTATTCGAGAGGAGTTATTCGAACTGGAGGTCAGAATTACCCGCACGGACTGGGAGTGTG | 2640 |
| GGATGTGGAGATGAAGAACTGGTGCATACGTCCAGTGGTCACTGAACATGCTTATGTGTT | 2700 |
| CCAACCAGACAAACGTATGGATGATTGGTCGGGATACTTAGAAGTGGCTGTTTGGGAACG | 2760 |
| AGGTATGTTGGTCAACGACTTCGCGGTCGAAAGGATGAGTGATTATGTCATAGTTTGCGA | 2820 |
| TCAGACGTATCTTTGCAATAACAGGTTGATCTTGGACAATTTAAGTGCCCTGGATCTAGG | 2880 |

```
ACCAGTTAACTGTTCTTTTGAATTAGTTGACGGTGTACCTGGTTGTGGTAAGTCGACAAT      2940

GATTGTCAACTCAGCTAATCCTTGTGTCGATGTGGTTCTCTCTACTGGGAGAGCAGCAAC      3000

CGACGACTTGATCGAGAGATTCGCGAGCAAAGGTTTTCCATGCAAATTGAAAAGGAGAGT      3060

GAAGACGGTTGATTCTTTTTTGATGCATTGTGTTGATGGTTCTTTAACCGGAGACGTGTT      3120

GCATTTCGATGAAGCTCTCATGGCCCATGCTGGTATGGTGTACTTTTGCGCTCAGATAGC      3180

TGGTGCTAAACGATGTATCTGTCAAGGAGATCAGAATCAAATTTCTTTCAAGCCTAGGGT      3240

ATCTCAAGTTGATTTGAGGTTTTCTAGTCTGGTCGGAAAGTTTGACATTGTTACAGAAAA      3300

AAGAGAAACTTACAGAAGTCCAGCAGATGTGGCTGCCGTATTGAACAAGTACTATACTGG      3360

AGATGTCAGAACACATAACGCGACTGCTAATTCGATGACGGTGAGGAAGATTGTGTCTAA      3420

AGAACAGGTTTCTTTGAAGCCTGGTGCTCAGTACATAACTTTCCTTCAGTCTGAGAAGAA      3480

GGAGTTGGTAAATTTGTTGGCATTGAGGAAAGTGGCAGCTAAAGTGAGTACAGTACACGA      3540

GTCGCAAGGAGAGACATTCAAAGATGTAGTCCTAGTCAGGACGAAACCTACGGATGACTC      3600

AATCGCTAGAGGTCGGGAGTACTTAATCGTGGCGTTGTCGCGTCACACACAATCACTTGT      3660

GTATGAAACTGTGAAAGAGGACGATGTAAGCAAAGAGATCAGGGAAAGTGCCGCGCTTAC      3720

GAAGGCGGCTTTGGCAAGATTTTTTGTTACTGAGACCGTCTTATGACGGTTTCGGTCTAG      3780

GTTTGATGTCTTTAGACATCATGAAGGGCCTTGCGCCGTTCCAGATTCAGGTACGATTAC      3840

GGACTTGGAGATGTGGTACGACGCTTTGTTTCCGGGAAATTCGTTAAGAGACTCAAGCCT      3900

AGACGGGTATTTGGTGGCAACGACTGATTCCAATTTGCGATTAGACAATGTTACGATCAA      3960

AAGTGGAAACTGGAAAGACAAGTTTGCTGAAAAAGAAACGTTTCTGAAACCGGTTATTCG      4020

TACTGCTATGCCTGACAAAAGGAAGACTACTCAGTTGGAGAGTTTGTTAGCATTGCAGAA      4080

AAGGAACCAAGCGGCACCCGATCTACAAGAAAATGTGCACGCAACAGTTCTAATCGAAGA      4140

GACGATGAAGAAGTTGAAATCTGTTGTCTACGATGTGGGAAAAATTCGGGCTGATCCTAT      4200

TGTCAATAGAGCTCAAATGGAGAGATGGTGGAGAAATCAAAGCACAGCGGTACAGGCTAA      4260

GGTAGTAGCAGATGTGAGAGAGTTACATGAAATAGACTATTCGTCTTACATGTATATGAT      4320

CAAATCTGACGTGAAACCTAAGACTGATTTAACACCGCAATTTGAATACTCAGCTCTACA      4380

GACTGTTGTGTATCACGAGAAGTTGATCAACTCGTTGTTCGGTCCAATTTTCAAAGAAAT      4440

TAATGAACGCAAGTTGGATGCTATGCAACCACATTTTGTGTTCAACACGAGAATGACATC      4500

GAGTGATTTAAACGATCGAGTGAAGTTCTTAAATACGGAAGCGGCTTACGACTTTGTTGA      4560

GATAGACATGTCTAAATTCGACAAGTCGGCAAATCGCTTCCATTTACAACTGCAGCTGGA      4620

GATTTACAGGTTATTTGGGCTAGATGAGTGGGCGGCCTTCCTTTGGGAGGTGTCGCACAC      4680

TCAAACTACTGTGAGAGATATTCAAAATGGTATGATGGCGCATATTTGGTACCAACAAAA      4720

GAGTGGAGATGCTGATACTTATAATGCAAATTCAGATAGAACACTGTGTGCACTCTTGTC      4800

TGAATTACCATTGGAGAAAGCAGTCATGGTTACATATGGAGGAGATGACTCACTGATTGC      4860

GTTTCCTAGAGGAACGCAGTTTGTTGATCCGTGTCCAAAGTTGGCTACTAAGTGGAATTT      4920

CGAGTGCAAGATTTTTAAGTACGATGTCCCAATGTTTTGTGGGAAGTTCTTGCTTAAGAC      4980

GTCATCGTGTTACGAGTTCGTGCCAGATCCGGTAAAAGTTCTGACGAAGTTGGGGAAAAA      5040

GAGTATAAAGGATGTGCAACATTTAGCCGAGATCTACATCTCGCTGAATGATTCCAATAG      5100

AGCTCTTGGGAACTACATGGTGGTATCCAAACTGTCCGAGTCTGTTTCAGACCGGTATTT      5160

GTACAAAGGTGATTCTGTTCATGCGCTTTGTGCGCTATGGAAGCATATTAAGAGTTTTAC      5220

AGCTCTGTGTACATTATTCCGAGACGAAAACGATAAGGAATTGAACCCGGCTAAGGTTGA      5280
```

-continued

| | |
|---|---|
| TTGGAAGAAGGCACAGAGAGCTGTGTCAAACTTTTACGACTGGTAATATGGAAGACAAGT | 5340 |
| CATTGGTCACCTTGAAGAAGAAGACTTTCGAAGTCTCAAAATTCTCAAATCTAGGGGCCA | 5400 |
| TTGAATTGTTTGTGGACGGTAGGAGGAAGAGACCGAAGTATTTTCACAGAAGAAGAGAAA | 5460 |
| CTGTCCTAAATCATGTTGGTGGGAAGAAGAGTGAACACAAGTTAGACGTTTTTGACCAAA | 5520 |
| GGGATTACAAAATGATTAAATCTTACGCGTTTCTAAAGATAGTAGGTGTACAACTAGTTG | 5580 |
| TAACATCACATCTACCTGCAGATACGCCTGGGTTCATTCAAATCGATCTGTTGGATTCGA | 5640 |
| GACTTACTGAGAAAAGAAAGAGAGGAAAGACTATTCAGAGATTCAAAGCTCGAGCTTGCG | 5700 |
| ATAACTGTTCAGTTGCGCAGTACAAGGTTGAATACAGTATTTCCACACAGGAGAACGTAC | 5760 |
| TTGATGTCTGGAAGGTGGGTTGTATTTCTGAGGGCGTTCCGGTCTGTGACGGTACATACC | 5820 |
| CTTTCAGTATCGAAGTGTCGCTAATATGGGTTGCTACTGATTCGACTAGGCGCCTCAATG | 5880 |
| TGGAAGAACTGAACAGTTCGGATTACATTGAAGGCGATTTTACCGATCAAGAGGTTTTCG | 5940 |
| GTGAGTTCATGTCTTTGAAACAAGTGGAGATGAAGACCATTCACGCGAAGTACGATGGTC | 6000 |
| CTTACAGACCAGCTACTACTAGACCTAAGTCATTATTGTCAAGTGAAGATGTTAAGAGAG | 6060 |
| CGTCTAATAAGAAAAACTCGTCTTAATGCATAAAGAAATTTATTGTCAATATGACGTGTG | 6120 |
| TACTCAAGGGTTGTGTGAATGAAGTCACTGTTCTTGGTCACGAGACGTGTAGTATCGGTC | 6180 |
| ATGCTAACAAATTGCGAAAGCAAGTTGCTGACATGGTTGGTGTCACACGTAGGTGTGCGG | 6240 |
| AAAATAATTGTGGATGGTTTGTCTGTGTTGTTATCAATGATTTTACTTTTGATGTGTATA | 6300 |
| ATTGTTGTGGCCGTAGTCACCTTGAAAAGTGTCGTAAACGTGTTGAAACAAGAAATCGAG | 6360 |
| AAATTTGGAAACAAATTCGACGAAATCAAGCTGAAAACATGTCTGCGACAGCTAAAAAGT | 6420 |
| CTCATAATTCGAAGACCTCTAAGAAGAAATTCAAAGAGGACAGAGAATTTGGGACACCAA | 6480 |
| AAAGATTTTTAAGAGATGATGTTCCTTTCGGGATTGATCGTTTGTTTGCTTTTTGA_TTTT | 6540 |
| ATTTTATATTGTTATCTGTTTCTGTGTATAGACTGTTTGAGATTGGCGCTTGGCCGACTC | 6600 |
| ATTGTCTTACCATAGGGAACGGACTTTGTTTGTGTTGTTATTTTATTTGTATTTTATTA | 6660 |
| AAATTCTCAATGATCTGAAAAGGCCTCGAGGCTAAGAGATTATTGGGGGTGAGTAAGTA | 6720 |
| CTTTTAAAGTGATGATGGTTACAAAGGCAAAAGGGTAAAACCCCTCGCCTACGTAAGCG | 6780 |
| TTATTACGCCC | 6791 |

The amino acid sequence for the 194 kDa polymerase (POL) sequence encoded by the TRV-RNA1 of SEQ ID NO:1 is shown below (SEQ ID NO:2). The "Z" indicates the position of codon that forms a stop position for the 134 kDa polymerase, and is read through in the 194 kDa protein. Amino acids corresponding to the above bolded nucleotides are bolded and underlined.

(SEQ ID NO:2)

MANGNFKLSQLLNVDEMSAEQRSHFFDLMLTKPDCEIGQMMQRVVVDKVDDMIRERKTKD

PVIVHEVLSQKEQNKLMEIYPEFNIVFKDDKNMVHGFAAAERKLQALLLLDRVPALQEVD

DIGGQWSFWVTRGEKRIHSCCPNLDIRDDQREISRQIFLTAIGDQARSGKRQMSENELWM

YDQFRENIAAPNAVRCNNTYQGCTCRGFSDGKKKGAQYAIALHSLYDFKLKDLMATMVEK

KTKVVHAAMLFAPESMLVDEGPLPSVDGYYMKKNGKIYFGFEKDPSFSYIHDWEEYKKYL

LGKPVSYQGNVFYFEPWQVRGDTMLFSIYRIAGVPRRSLSSQEYYRRIYISRWEN_MVVVP

IFDLVESTRELVKKDLFVEKQFMDKCLDYIARLSDQQLTISNVKSYLSSNNWVLFINGAA

-continued

VKNKQSVDSRDLQLLAQTLLVKEQVARPVMRELREAILTETKPITSLTDVLGLISRKLWK

QFANKIAVGGFVGMVGTLIGFYPKKVLTWAKDTPNGPELCYENSHKTKVIVFLSVVYAIG

GITLMRRDIRDGLVKKLCDMFDIKRGAHVLDVENPCRYYEINDFFSSLYSASESGETVLP

DLSEVKAKSDKLLQQKKEIADEFLSAKFSNYSGSSVRTSPPSVVGSSRSGLGLLLEDSNV

LTQARVGVSRKVDDEEIMEQFLSGLIDTEAEIDEVVP_AFSAECERGETSGTKVLCKPLTP

PGFENVLPAVKPLVSKGKTVKRVDYFQVMGGERLPKRPVVSGDDSVDARREFLYYLDAER

VAQNDEIMSLYRDYSRGVIRTGGQNYPHGLGVWDVEMKNWCIRPVVTEHAYVFQPDKRMD

DWSGYLEVAVWERGMLVNDFAVERMSDYVIVCDQTYLCNNRLILDNLSALDLGPVNCSFE

LVDGVPGCGKSTMIVNSANPCVDVVLSTGRAATDDLIERFASKGFPCKLKRRVKTVDSFL

MHCVDGSLTGDVLHFDEALMAHAGMVYFCAQIAGAKRCICQGDQNQISFKPRVSQVDLRF

SSLVGKFDIVTEKRETYRSPADVAAVLNKYYTGDVRTHNATANSMTVRKIVSKEQVSLKP

GAQYITFLQSEKKELVNLLALRKVAAKVSTVHESQGETFKDVVLVRTKPTDDSIARGREY

LIVALSRHTQSLVYETVKEDDVSKEIRESAALTKAALARFFVTETVLZRFRSRFDVFRHH

EGPCAVPDSGTITDLEMWYDALFPGNSLRDSSLDGYLVATTDCNLRLDNVTIKSGNWKDK

FAEKETFLKPVIRTAMPDKRKTTQLESLLALQKRNQAAPDLQENVHATVLIEETMKKLKS

VVYDVGKIRADPIVNRAQMERWWRNQSTAVQAKVVADVRELHEIDYSSYMYMIKSDVKPK

TDLTPQFEYSALQTVVYHEKLINSLFGPIFKEINERKLDAMQPHFVFNTRMTSSDLNDRV

KFLNTEAAYDFVEIDMSKFDKSANRFHLQLQLEIYRLFGLDEWAAFLWEVSHTQTTVRDI

QNGMMAHIWYQQKSGDADTYNANSDRTLCALLSELPLEKAVMVTYGGDDSLIAFPRGTQF

VDPCPKLATKWNFECKIFKYDVPMFCGKFLLKTSSCYEFVPDPVKVLTKLGKKSIKDVQH

LAEIYISLNDSNRALGNYMVVSKLSESVSDRYLYKGDSVHALCALWKHIKSFTALCTLFR

DENDKELNPAKVDWKKAQRAVSNFYDW

The amino acid sequence for the movement protein (MP) encoded by the TRV-RNA1 of SEQ ID NO:1 is shown below (SEQ ID NO:3). Amino acids corresponding to the above bolded nucleotides are bolded and underlined.

MEDKSLVTLKKKTFEVSKFSNLGAIELFVDGRRKRPKYFHRRRETVLNHVGGKKSEHKLD  (SEQ ID NO:3)

VFDQRDYKMIKSYAFLKIVGVQLVVTSHLPADTPGFIQIDLLDSRLTEKRKRGKTIQRFK

ARACDNCSVAQYKVEYSISTQENVLDVWKVGCISEGVPVCDGTYPFSIEVSLIWVATDST

RRLNVEELNSSDYIEGDFTDQEVFGEFMSLKQVEMKTIEAKYDGPYRPATTRPKSLLSSE

DVKRASNKKNSS

The amino acid sequence for the 16 kDa protein encoded by the TRV-RNA1 of SEQ ID NO: 1 is shown below (SEQ ID NO:4).

```
                                                            (SEQ ID NO:4)
MTCVLKGCVNEVTVLGHETCSIGHANKLRKQVADMVGVTRRCAENNCGWFVCVVINDFTFDVYNCCGRSHLE

KCRKRVETRNREIWKQIRRNQAENMSATAKKSHNSKTSKKKFKEDREFGTPKRFLRDDVPFGIDRLFAF
```

Example 2

Certain TRV-RNA2 Sequences

The following is a TRV-RNA2 sequence containing nucleotides at particular positions (bolded in the sequence below) and providing improved plant transformation. The coat protein open reading frame is underlined.

```
                                                            (SEQ ID NO:5)
ATAAAACATTGCACCTATGGTGTTGCCCTGGCTGGGGTATGTCAGTGATCGCAGTAGAAT    60

GTACTAATTGACAAGTTGGAGAATACGGTAGAACGTCCTTATCCAACACAGCCTTTATCC   120

CTCTCCCTGACGAGGTTTTTGTCAGTGTAATATTTCTTTTTGAACTATCCAGCTTAGTAC   180

CGTACGGGAAAGTGACTGGTGTGCTTATCTTTGAAATGTTACTTTGGGTTTCGGTTCTTT   240

AGGTTAGTAAGAAAGCACTTGTCTTCTCATACAAAGGAAAACCTGAGACGTATCGCTTAC   300

GAAAGTAGCAATGAAAGAAAGGTGGTGGTTTTAATCGCTACCGCAAAAACGATGGGGTCG   360

TTTTAATTAACTTCTCCTACGCAAGCGTCTAAACGGACGTTGGGGTTTTGCTAGTTTCTT   420

TAGAGAAAACTAGCTAAGTCTTTAATGTTATCATTAGAGATGGCATAAATATAATACTTG   480

TGTCTGCTGATAAGATCATTTTAATTTGGACGATTAGACTTGTTGAACTACAGGTTACTG   540

AATCACTTGCGCTAATCAACATGGGAGATATGTACGATGAATCATTTGACAAGTCGGGCG   600

GTCCTGCTGACTTGATGGACGATTCTTGGGTGGAATCAGTTTCGTGGAAAGATCTGTTGA   660

AGAAGTTACACAGCATAAAATTTGCACTACAGTCTGGTAGAGATGAGATCACTGGGTTAC   720

TAGCGGCACTGAATAGACAGTGTCCTTATTCACCATATGAGCAGTTTCCAGATAAGAAGG   780

TGTATTTCCTTTTAGACTCACGGGCTAACAGTGCTCTTGGTGTGATTCAGAACGCTTCAG   840

CGTTCAAGAGACGAGCTGATGAGAAGAATGCAGTGGCGGGTGTTACAAATATTCCTGCGA   900

ATCCAAACACAACGGTTACGACGAACCAAGGGAGTACTACTACTACCAAGGCGAACACTG   960

GCTCGACTTTGGAAGAAGACTTGTACACTTATTACAAATTCGATGATGCCTCTACAGCTT  1020

TCCACAAATCTCTAACTTCGTTAGAGAACATGGAGTTGAAGAGTTATTACCGAAGGAACT  1080

TTGAGAAAGTATTCGGGATTAAGTTTGGTGGAGCAGCTGCTAGTTCATCTGCACCGCCTC  1140

CAGCGAGTGGAGGTCCGATACGTCCTAATCCCTAGGGATTTAAGGACGTGAACTCTGTTG  1200

AGATCTCTGTGAAATTCAGAGGGTGGGTGATACCATATTCACTGATGCCATTAGCGACAT  1260

CTAAATAGGGCTAATTGTGACTAATTTGAGGGAATTTCCTTTACCATTGACGTCAGTGTC  1320

GTTGGTAGCATTTGAGTTTCGCAATGCACGAATTACTTAGGAAGTGGCTTGACGACACTA  1380

ATGTGTTATTGTTAGATAATGGTTTGGTGGTCAAGGTACGTAGTAGAGTCCCACATATTC  1440

GCACGTATGAAGTAATTGGAAAGTTGTCAGTTTTTGATAATTCACTGGGAGATGATACGC  1500

TGTTTGAGGGAAAAGTAGAGAACGTATTTGTTTTTATGTTCAGGCGGTTCTTGTGTGTCA  1560

ACAAAGATGGACATTGTTACTCAAGGAAGCACGATGAGCTTTATTATTACGGACGAGTGG  1620

ACTTAGATTCTGTGAGTAAATGTCCCGAAGACATTAAACTACGGTTCTTTAAGTAGATCC  1680
```

-continued

```
GTGTCTGAAGTTTTAGGTTCAATTTAAACCTACGAGATTGACATTCTCGACTGATCTTGA      1740

TTGATCGGTAAGTCTTTTGTAATTTAATTTTCTTTTTGATTTTATTTTAAATTGTTATCT      1800

GTTTCTGTGTATAGACTGTTTGAGATCGGCGTTTGGCCGACTCATTGTCTTACCATAGGG      1860

GAACGGACTTTGTTTGTGTTGTTATTTTATTTGTATTTTATTAAAATTCTCAACGATCTG      1920

AAAAAGCCTCGCGGCTAAGAGATTGTTGGGGGGTGAGTAAGTACTTTTAAAGTGATGATG      1980

GTTACAAAGGCAAAAGGGGTAAAACCCCTCGCCTACGTAAGCGTTATTACGCCC            2034
```

The amino acid sequence for the coat protein encoded by the TRV-RNA2 of SEQ ID NO:2 is shown below (SEQ ID NO:6).

(SEQ ID NO:6)
MGDMYDESFDKSGGPADLMDDSWVESVSWKDLLKKLHSIKFALQSGRDEITGLLAALNRQCPYSPYEQFPDK

KVYFLLDSRANSALGVIQNASAFKRRADEKNAVAGVTNIPANPNTTVTTNQGSTTTTKANTGSTLEEDLYTY

YKFDDASTAFHKSLTSLENMELKSYYRRNFEKVFGIKFGGAAASSSAPPPASGGPIRPNP

Example 3

Gene Silencing Using a Novel Tobacco Rattle Virus System

This example describes the construction of a tobacco rattle virus (TRV) vector and its used for gene silencing in plants. Virus induce gene silencing (VIGS) is initiated when a recombinant virus carrying a sequence from a host gene infects the plant. The endogenous gene transcripts homologous to the insert in the VIGS vector are degraded by a post-transcriptional gene silencing mechanism (PTGS) (Baulcombe, 1999).

Development of a TRV Based VIGS System

TRV is a bipartite positive sense RNA virus (MacFarlane, 1999). RNA1 encodes 134 and 194 kDa replicase proteins from the genomic RNA, a 29-kDa movement protein and 16-kDa cysteine-rich protein from subgenomic RNAs (FIG. 1a). RNA2 encodes the coat protein from the genomic RNA and two non-structural proteins from the subgenomic RNAs (FIG. 1a). TRV RNA1 can replicate and move systemically without RNA2. To develop TRV as a VIGS vector, applicants constructed T-DNA vectors containing cDNA clones of RNA1 and RNA2 of Ppk20 strain (FIG. 1b). The cDNAs corresponding to RNA1 and RNA2 were inserted immediately following the duplicated CaMV 35S promoter transcriptional start site so that no non-TRV nucleotides are present at the 5' end after transcription. In addition, a self-cleaving ribozyme sequence (Turpen et al., 1993) was included at the 3' end so that only three non-viral nucleotides are predicted to be present after transcription. In the TRV RNA2 cDNA construct, the non-structural genes were replaced with a multiple cloning site (MCS) useful for cloning the target gene sequences for VIGS (FIG. 1b). The biological activity of the TRV clones was confirmed by mixing Agrobacterium cultures containing RNA1 and RNA2 T-DNA constructs and infiltrating the mixture into the leaves of N. benthamiana. An initial test with two independent RNA1 and RNA2 cDNA clones proved to be less infectious than the wild type virus (data not shown); possibly due to sequence changes introduced during RT-PCR. Therefore, sequences that were consistent among each of three independent RNA1 and RNA2 clones, though different from the GenBank sequence, were considered as correct sequences. Based on this information, applicants reconstructed the RNA1 and RNA2 cDNA clones. The infectivity of this new TRV clone was comparable to that of wild type Ppk20 virus (data not shown). The T-DNA constructs corresponding to RNA1 and RNA2 are referred to herein as pTRV1 and pTRV2, respectively.

The TRV based VIGS vectors described in this example include a variety of improvements and desirable properties. For example, the vectors include a double 35S promoter; the RNA1 cDNA is stable at room temperature in the pBIN19 vector in E. coli and therefore disruption of the polymerase ORF by inclusion of an intron is not required; transcription initiation is predicted in vivo at the first nucleotide of TRV cDNA; and inclusion of a ribozyme at the 3' end ensures generation of a precise 3' end of the RNA.

Applicants assessed the gene silencing efficiency of the TRV-VIGS clones by suppressing the expression of the phytoene desaturase (PDS) gene in N. benthamiana. A mixture of Agrobacterium culture containing the pTRV2-PDS and pTRV1 was infiltrated on to the 4-leaf stage N. benthamiana plants (for details see Experimental procedures). The silencing effect was monitored in the upper leaves of the plant 5-7 days post Agro-inoculation. Silencing of PDS leads to the inhibition of carotenoid synthesis, causing the plants to exhibit a photo-bleached phenotype (FIG. 1c; Kumagai et al., 1995). The PDS suppression phenotype was visible 5 days post Agro infiltration in the upper leaves of the plant and persisted indefinitely. This result indicated that the TRV-VIGS system could be successfully used to induce silencing of other desirable endogenous plant genes. Moreover, PDS suppression effect was visible uniformly throughout the entire leaf (FIG. 1c). Uniform suppression of target gene is helpful for the study of disease resistance using VIGS because often these experiments involve secondary infection with another pathogen.

Generation of N-containing Transgenic N. benthamiana to Study TMV Resistance

Figure 2:
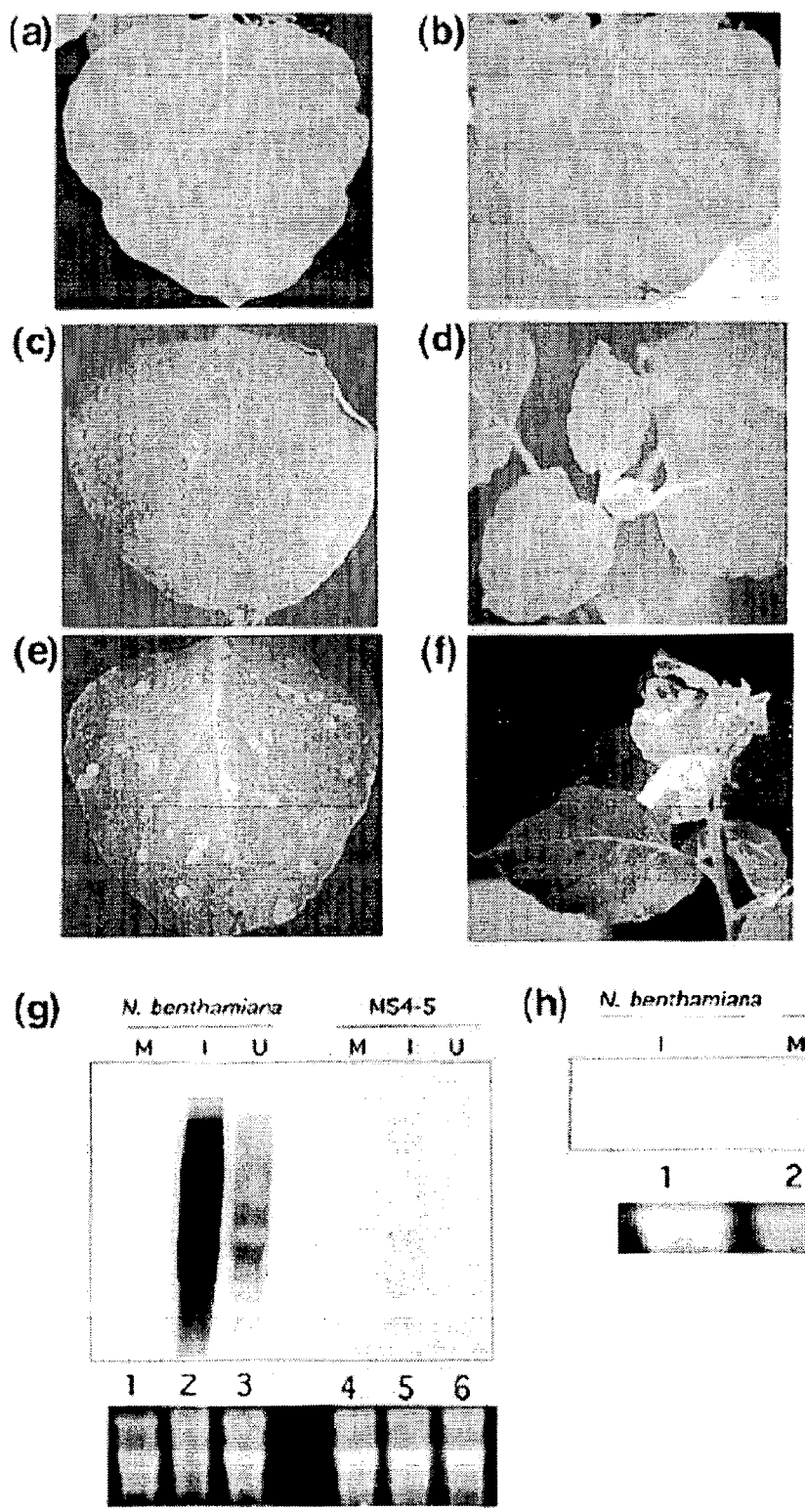
FIG. 2. Response to TMV and TMV-GFP in transgenic N containing MS4-5 and control *N. benthamiana* plants. (a,b) Hypersensitive response (HR) of transgenic MS4-5 line containing the N gene (a) and no HR in control *N. benthamiana* plants (b) 3 days after TMV infection. (c-f) Response of MS4-5 plants to TMV-GFP in the inoculated leaf (c) and upper uninoculated leaves (d). Response of control *N. benthamiana* plants to TMV-GFP in the inoculated leaf (e)and upper un-inoculated leaves (f). GFP pictures were taken under UV illumination. Inoculated leaf pictures were taken 1 day after infection and the pictures of upper leaves were taken 10 days later. (g) Northern blot analysis of TMV RNA accumulation in mock (M), infected (I) and upper un-inoculated (U) leaves of *N. benthamiana* (left) and MS4-5 (right) plants probed with the MP gene of TMV. Each lane contains 5 μg of total RNA. TMV RNA accumulation was measured 3 days after infection in the inoculated leaves and 10 days after infection in the upper uninoculated leaves. The picture of the ethidium bromide stained gel shown below the blot indicates equal loading of RNA. (h) PR1a message accumulation in infected (I) control *N. benthamiana* and mock (M) and infected (I) MS4-5 leaves 72 h after TMV infection blots were prepared using 10 μg of total RNA and probed with PR1a cDNA. The picture of the ethidium bromide stained gel shown below the blot indicates equal loading of RNA.

The N gene response to TMV infection is routinely studied using N. tabacum cv. Xanthi nc or N. tabacum cv. Samsun NN or transgenic N. tabacum cv. SR1 containing the N transgene (Holmes, 1934; Whitham et al., 1994). In tobacco, recombinant TMV-GFP virus fails to move systemically. However, TMV-GFP virus moves systemically in *N. benthamiana*. Therefore, applicants generated transgenic *N. benthamiana* lines containing the N gene construct pSPDK694. This construct contains the N promoter+cDNA-NS+Intron III containing the alternative exon+N genomic-3'end. This is the minimum N sequence required to confer resistance to TMV (Dinesh-Kumar and Baker, 2000). Applicants transformed *N. benthamiana* plants with pSPDK694 and generated 10 independent primary transgenic lines. Six independent transgenic lines showed HR upon infection with TMV-U1 strain with no symptoms elsewhere in the plant. Applicants isolated homozygous line, MS4-5, containing a single copy of T-DNA and was used for the experiments described in this paper. The transgenic MS4-5 line exhibits HR lesions on the inoculated leaf 48-72 h after infection with TMV (FIG. 2a). The HR lesion phenotype observed in MS4-5 plants is similar to that observed in the wild type N-containing tobacco plants (Whitham et al., 1994). In contrast, the non-transformed *N. benthamiana* plants fail to induce HR in response to TMV (FIG. 2b). In the VIGS assay described below, applicants use TMV-GFP virus to monitor TMV movement under UV illumination. Therefore, applicants tested the effect of TMV-GFP virus infection on MS4-5 and *N. benthamiana* plants. In MS4-5 plants, GFP fluorescence was observed 24 h after infection on inoculated leaves (FIG. 2c); but the upper uninoculated leaves of the infected plant did not show systemic spread of TMV-GFP even 10 days after infection (FIG. 2d). In *N. benthamiana* control plants, GFP fluorescence was visible in the inoculated leaf after 24 h (FIG. 2e). The infection foci as indicated by the area of GFP fluorescence spot were much bigger as compared to that of MS4-5 plants (compare FIG. 2e versus FIG. 2c). After 10 days, TMV-GFP was observed in the upper leaves of the control plants (FIG. 2f). These results suggest that transgenic N containing MS4-5 plants exhibit HR upon TMV infection and that the virus is restricted to the infection site. To confirm the phenotypic data, RNA gel blots were prepared using RNA extracted from mock and TMV infected plants and hybridized with a probe derived from the movement protein (MP) gene of TMV. In mock inoculated *N. benthamiana* (FIG. 2g; lane 1) and MS4-5 plants (FIG. 2g; lane 4), no hybridization signal was observed. As expected, in susceptible wild-type *N. benthamiana* plants, TMV-RNA accumulated to a high level in inoculated leaves (FIG. 2g; lane 2) as well as in the systemic upper leaves (FIG. 2g; lane 3). In MS4-5 transgenic plants, a low level of TMV-RNA was detected in the inoculated leaf (FIG. 2g; lane 5) and no viral RNA was detected in the upper un-inoculated leaves (FIG. 2g; lane 6). These results confirm that the MS4-5 line restricts TMV to the inoculated leaf.

In NN tobacco plants, HR and SAR to TMV are associated with the induction of PR proteins (Hooft van Huijsduijnen et al., 1986; Ward et al., 1991).Applicants investigated the induction of PR1a message in TMV inoculated leaves of wild type *N. benthamiana* and transgenic MS4-5 lines using RNA gel blots.NoPR1a message was detected in either mock-infected MS4-5 plants (FIG. 2h; lane 2) or in TMV infected *N. benthamiana* plants (FIG. 2h; lane 1). On the other hand, PR1a expression was induced in TMV infected NcontainingMS4-5 transgenic plants (FIG. 2h;lane3). These results suggest that transgenic MS4-5 lines induce PR1a message just as wild-type N-containing tobacco plants do.

Taken together, the phenotypic and molecular analyses of the MS4-5 line demonstrate that the tobacco N gene can confer resistance to TMV in heterologous *N. benthamiana* plants and can be used to study N-mediated signaling in TMV resistance.

Suppression of N Function Using TRV Based VIGS

Figure 3:
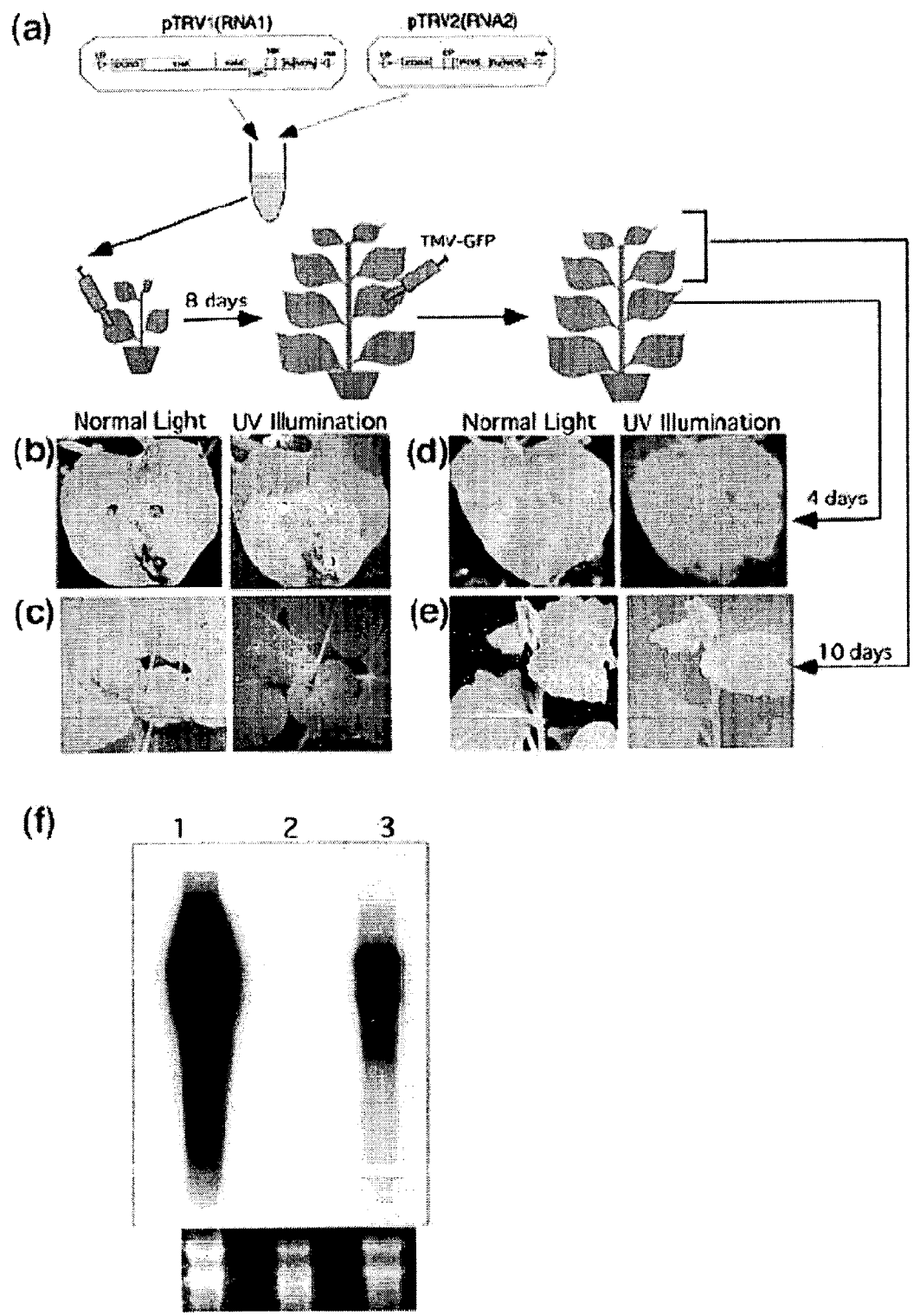
FIG. 3. Effect of TRV infection on resistant and susceptibility response to TMV-GFP. (a) *Agrobacterium* cultures containing pTRV1 and pTRV2 were mixed in 1:1 ratio and infiltrated on to 4-leaf stage plant using 1 ml needle-less syringe. Eight days after infiltration, these plants were infiltrated with *Agrobacterium* culture containing TMV-GFP construct. (b,c) TMV-GFP infection in TRV infected MS4-5 plants in the infiltrated leaf (b) and systemic upper leaves (c). (d,e) TMV-GFP infection in TRV infected *N. benthamiana* plants in the infiltrated leaf (d) and in the systemic upper leaves (e). (f) Northern blot analysis to measure TMV-GFP RNA accumulation in the upper leaves of TRV infected *N. benthamiana* (lane 1) and MS4-5 (lane 2) plants. TMV-GFP RNA accumulation in the upper leaves of TRV-N infected MS4-5 plants (lane 3). TMV-GFP RNA accumulation was measured 10 days after infection. In each lane, 5 μg of total RNA was loaded. The blot was probed with the MP gene of TMV. The picture of the ethidium bromide stained gel shown below the blot indicates equal loading of RNA.

Applicants tested the ability of the TRV-VIGS system to induce silencing of the N gene to determine whether the system could be used for TMV resistance pathway gene function studies. Applicants hypothesized that the suppression of N using TRV-VIGS should result in loss-of-resistance to TMV. First, applicants needed to observe whether TRV infection alone has an effect on N-mediated resistance to TMV. A mixture of *Agrobacterium* containing pTRV1 and pTRV2 was infiltrated into MS4-5 and wild type *N. benthamiana* plants (FIG. 3a). Eight days post infiltration, the upper leaves of these plants were infiltrated with *Agrobacterium* containing the TMV-GFP construct to monitor resistant and susceptible phenotypes. In MS4-5 plants, an HR phenotype was observed within 72 h and the GFP fluorescence signal was restricted to the infiltrated area (FIG. 3b), and after 6 days, the signal was reduced significantly (data not shown). Systemic leaves of these plants showed no sign of TMV-GFP fluorescence even after 10 days (FIG. 3c). Wild type *N. benthamiana* plants showed no HR at the site of infiltration (FIG. 3d) and TMV-GFP was able to spread throughout the plant in 10 days (FIG. 3e) with no reduction in the TMV-GFP signal in the infiltrated leaf. Applicants confirmed that the TMV-GFP is restricted to the Agro-inoculation site in MS4-5 plants by Northern blot analysis (FIG. 3f) using the MP gene of TMV as a probe. In TRV infected wild-type *N. benthamiana* plants, TMV-GFP RNA was present in the upper un-infiltrated leaves (FIG. 3f; lane 1). There was no TMV-GFP RNA in the upper un-infiltrated leaves of TRV infected MS4-5 plants (FIG. 3f, lane 2). These results, together with the above-described phenotypic data, indicate that TRV infection alone has no effect on TMV resistance or susceptibility and could be used to study genes involved in N-mediated resistance to TMV using the TRV-based VIGS system.

Figure 4:
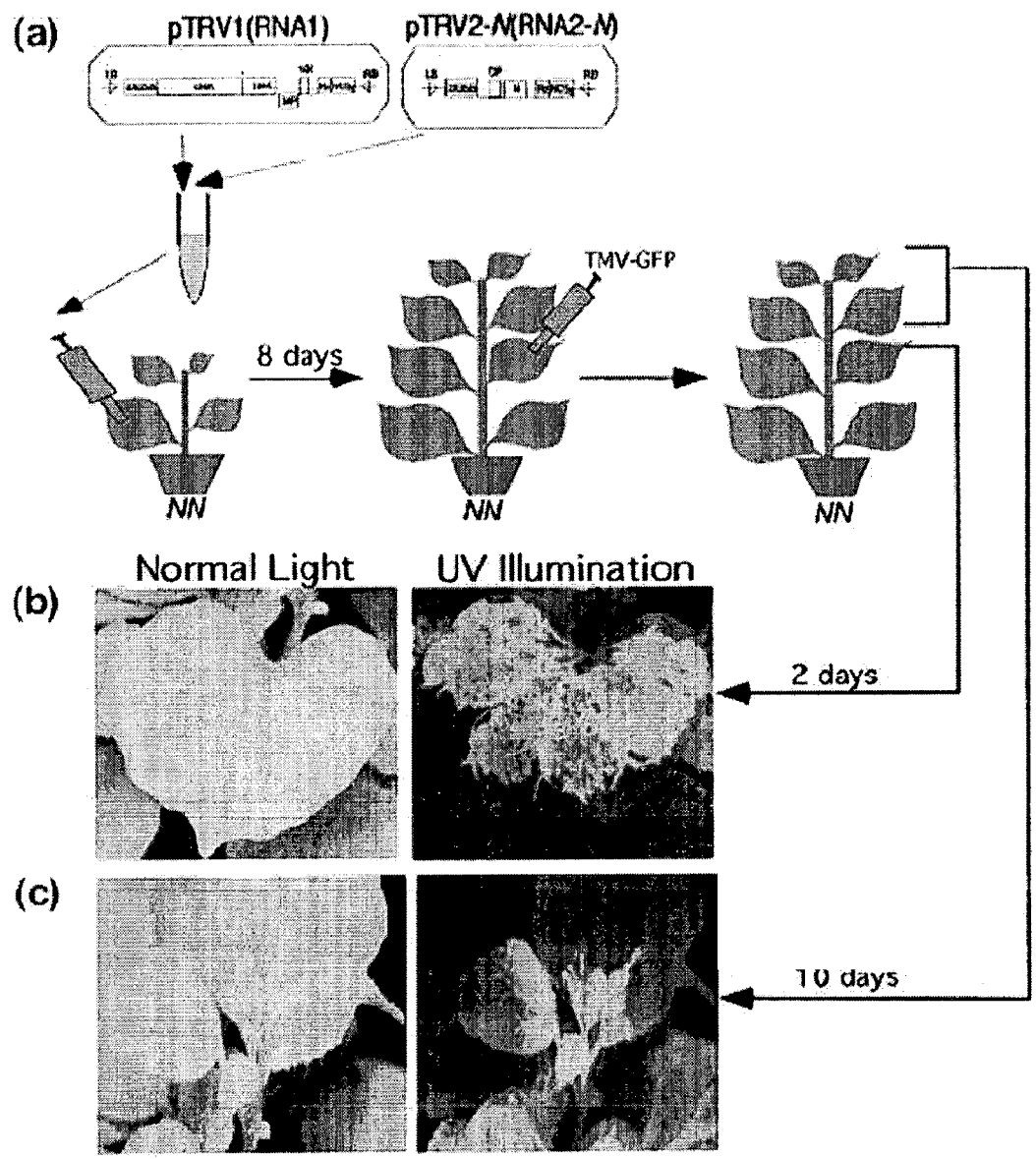
FIG. 4. TMV-GFP response to TRV-VIGS of N. (a) Plants were first infiltrated with pTRV1 and pTRV2-N. After 8 days, the upper leaf was infiltrated with TMV-GFP to monitor resistance and susceptible responses. (b) Suppression phenotype of N in MS4-5 plants in the infiltrated leaf. (c) Suppression phenotype in MS4-5 plants in the upper un-infiltrated leaves.

To suppress N function using TRV-VIGS, applicants cloned a 1129-bp fragment of the N cDNA corresponding to nt 86-1215 (Whitham et al., 1994) into pTRV2. A mixture of *Agrobacterium* cultures containing pTRV1 and pTRV2-N was infiltrated onto MS4-5 plants (FIG. 4a). Eight days post-infiltration, the upper leaves were infiltrated with *Agrobacterium* containing a TMV-GFP plasmid. These plants were then observed for at least 20 days for movement of TMV-GFP from the infiltrated site. The TRV-N infected MS4-5 plants failed to show characteristic HR phenotype in the infiltrated leaf (FIG. 4b) and the TMVGFP was able to spread to the upper leaves (FIG. 4c). Movement of TMV-GFP into the upper parts of the MS4-5 plants was detectable 6 days after TMV-GFP infiltration. Presence of TMV-GFP RNA in systemic leaves was confined by RNA blots hybridized to a probe derived from the MP gene of TMV (FIG. 3f, lane 3). These results indicate that the N transgene function is suppressed in MS4-5 plants by TRV-VIGS.

Figure 5:
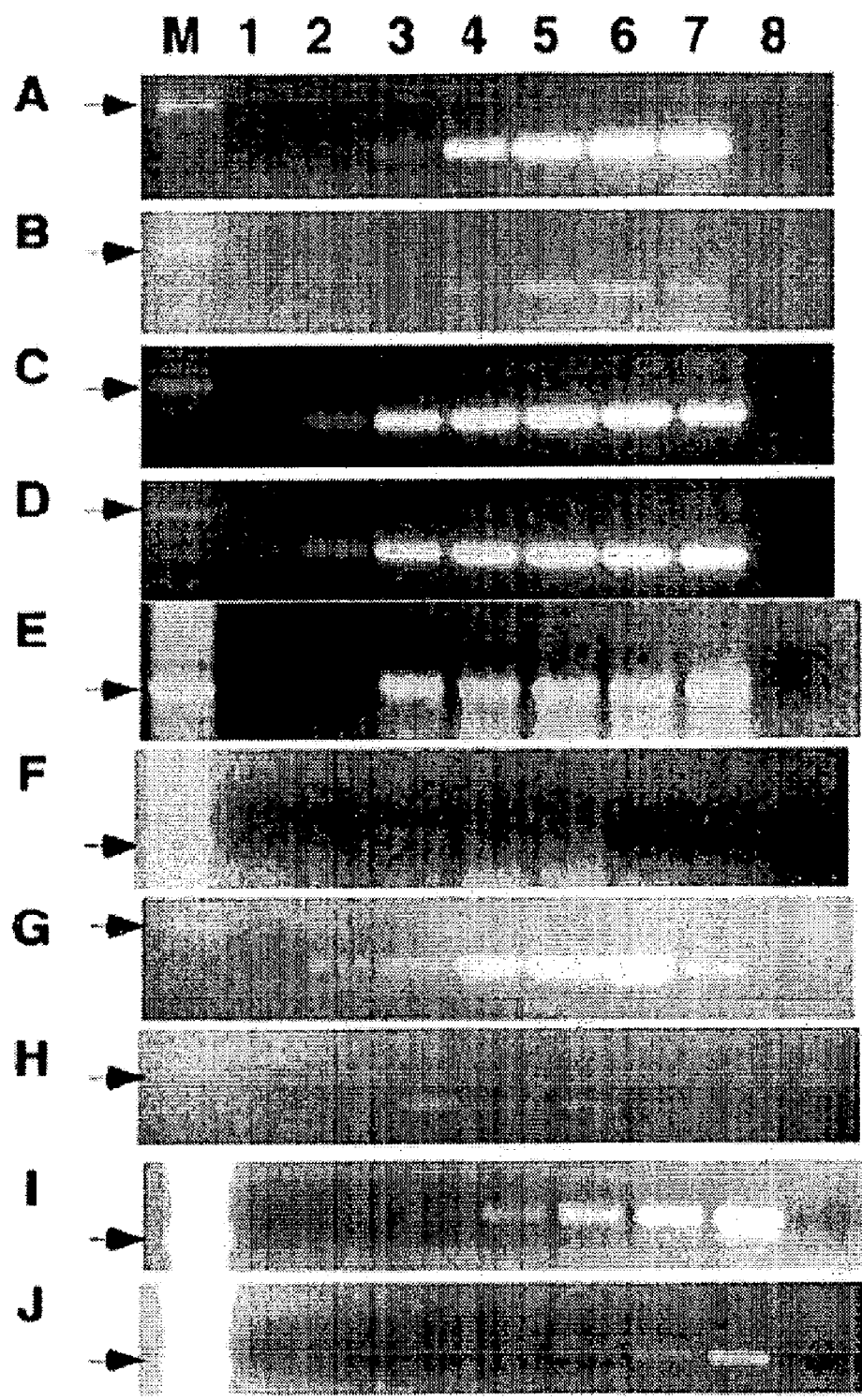
FIG. 5. VIGS effect on N, Rar1, EDS1 and NPR1 transcription in MS4-5 plants. Ethidium bromide-stained agarose gels showing RT-PCR products. The first strand cDNA was generated from total RNA isolated from silenced and non-silenced plants using oligo (dT) primer and reverse trascriptase. This first strand cDNA was used in a PCR reaction using gene specific primers. A, E, G, I: typical PCR products of N, Rar1, EDS1, and NPR1 derived from TRV infected non-silenced plants. B, F, H, and J: typical PCR products of N, Rar1, EDS1, and NPR1 derived from TRV-N, TRV-Rar1, TRV-EDS1 and TRV-NPR1 infected silenced plants. C and D (internal control): typical PCR products for EF1a derived from TRV alone infected (C) and TRV-VIGS vector infected (D) plants. Arrow indicates 600 bp size fragment in marker (M) lane. Lanes 1-7 corresponds to products from PCR cycle number 20, 25, 30, 35, 40, 45, and 50. Lane 8 represents the control in which the RT reaction mix, without reverse transcriptase, was used as a template.

Applicants performed semi-quantitative RT-PCR, using total RNA extracted from MS4-5 plants infected with TRV-N or TRV alone, to confirm the VIGS of the N gene at the molecular level. In TRV-N infected plants, the N message was reduced by more than 88% compared to the TRV infected control (FIG. 5a versus FIG. 5b). In both tissue RNA samples, EF1a RNA levels were similar (FIG. 5c versus FIG. 5d) and served as an internal control for RNA quality and RT-PCR amplification. These results show that the TRV based VIGS system efficiently suppresses targeted host genes and can be used as a rapid means for assaying the role of candidate genes in N-mediated resistance to TMV. Therefore, applicants set out to suppress tobacco Rar1, EDS1 and NPR1/NIM1 homologues in MS4-5 plants to investigate their role in N-mediated signaling.

Cloning of Tobacco Homologues of Rar1, EDS1, and NPR1/NIM1

In order to study the role of Rar1, EDS1 and NPR1/NIM1 in N-mediated resistance to TMV, applicants cloned tobacco homologues of these genes. Applicants used the amino acid sequence of barley Rar1 to search the Institute of Genomic Research (TIGR) tomato database using TBLASTN. Tomato EST clone TC96555 showed significant homology to barley Rar1. Based on this information, applicants designed primers described in the Experimental procedures section and performed RT-PCR to clone full-length Rar1 from *N. tabacum*. The nucleotide sequence of tobacco Rar1 has been deposited in GenBank (AF480487). Amino acid sequence analysis of tobacco Rar1 using a BLAST search shows 63% identity and 73% similarity to barley Rar1 (FIG. 6). Similar to barley Rar1, tobacco Rar1 contains two CHORD domains and one plant-specific CCCH domain (Shirasu et al., 1999). In addition, the tobacco Rar1 contains conserved strings of invariant cysteine and histidine residues within the CHORD domains (FIG. 6). The amino acid sequences outside the CHORD and CCCH domains are significantly different between tobacco Rar1 and barley Rar1 (FIG. 6).

To clone the tobacco EDS1 homologue, EST clones TC91460 and TC95587, which showed significant homology to *Arabidopsis* EDS1, were identified. Applicants cloned full length tobacco EDS1 using RT-PCR as described in the Experimental procedures section. The tobacco EDS1 sequence is deposited in GenBank (AF480489). Amino acid sequence analysis of tobacco EDS1 shows 43% identity and 58% similarity to *Arabidopsis* EDS1 (FIG. 7). Like *Arabidopsis* EDS1, tobacco EDS1 contains three lipase catalytic residues, S125, D186, H322 (Falk et al., 1999). In addition, the consensus sequence around the predicted catalytic S125 is highly conserved between tobacco EDS1 and *Arabidopsis* EDS1. Sequence of the eds1-1 allele in *Arabidopsis* indicated a change in the E466K (Falk et al., 1999), an amino acid that is conserved in tobacco EDS1.

A TIGR tomato database search using *Arabidopsis* NPR1/NIM1 identified EST clones TC95582, TC91366 and AW399343, which showed significant homology to the *Arabidopsis* NPR1. A full-length tobacco homologue of NPR1 was cloned using RT-PCR as described in the Experimental procedures section. The nucleotide sequence of full-length tobacco NPR1 has been deposited in GenBank (AF480488). Amino acid sequence analysis of tobacco NPR1 shows 52% identity and 72% similarity to *Arabidopsis* NPR1 (FIG. 8). Amino acid changes that lead to loss-of-function of NPR1 in *Arabidopsis* (Cao et al., 1997) are conserved in the tobacco NPR1 sequence (FIG. 8). In addition 4 out of 5 amino acids required for nuclear localization of *Arabidopsis* NPR1 (Kinkema et al., 2000) are also conserved in tobacco NPR1 (FIG. 8).

Role of Tobacco Rar1, EDS1 and NPR1/NIM1 in the NMediated Resistance to TMV

Figure 9:
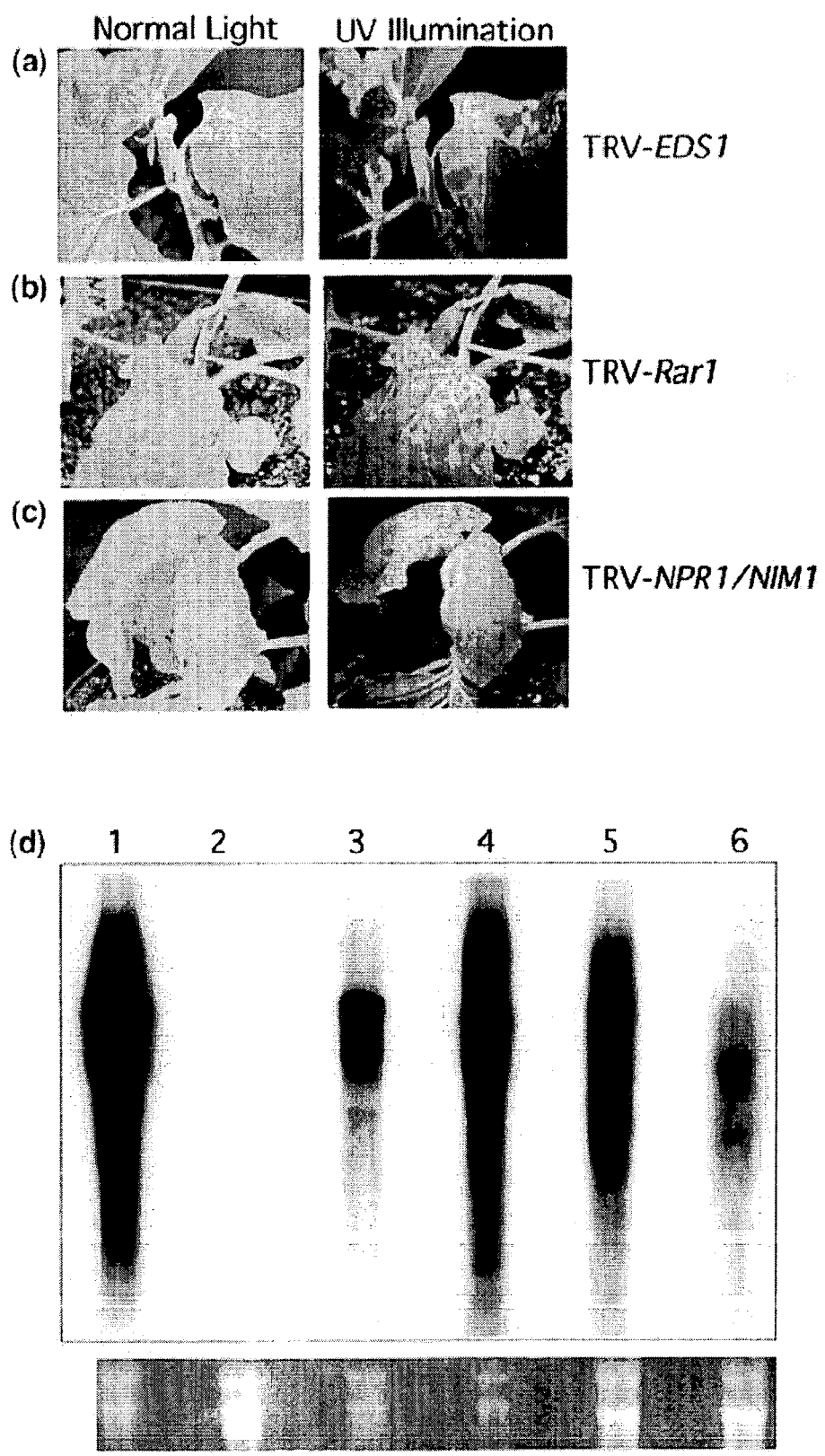
FIG. 9. TRV mediated VIGS of EDS1, Rar1 and NPR1/NIM1. TMV response in MS4-5 plants silenced for EDS1 (a), Rar1 (b), and NPR1/NIM1 (c); photographs were taken after 10 days of infection. Panel d represents the RNA gel blot analysis to measure TMV-GFP RNA accumulation in plants infected first with TRV or TRV derivatives and then followed by TMV-GFP infection. Lane 1: control *N. benthamiana* infected with TRV. Lane 2-6: MS4-5 plants infected with TRV (lane 2); TRV-N (lane 3); TRV-Rar1 (lane 4); TRV-EDS1 (lane 5); TRVNPR1/NIM1 (lane 6). Ten μg of total RNA was used in lane 6 and in all other lanes 5 μg was used. The MP gene of TMV was used as a probe. The picture of the ethidium bromide stained gel shown below the blot indicates equal loading of RNA.

In order to determine if Rar1, EDS1 and NPR1/NIM1 play important roles in N-mediated resistance, applicants cloned fragments of these genes into pTRV2 as described in the materials and methods section. A mixture of *Agrobacterium* cultures containing pTRV1 with pTRV2; pTRV2-Rar1; pTRV2-EDS1; or pTRV2-NPR1/NIM1 were each infiltrated on to 4-leaf stage MS4-5 plants. Eight days after infiltration, *Agrobacterium* containing the TMVGFP construct was infiltrated on to upper leaf of each of the plants. These plants were visualized under UV light 10 days later for movement of TMV-GFP. In the Rar1, EDS1 and NPR1/NIM1 suppressed plants, TMV-GFP spread into the upper leaves (FIGS. 9a-c) as visualized by the presence of GFP in the systemic leaves. More GFP fluorescence was consistently observed in the EDS1 and Rar1 than the NPR1/NIM1 silenced plants (compare FIGS. 9a-b versus FIG. 9c). Taken together, the phenotypic data suggest that suppression of Rar1-, EDS1- and NPR1/NIM1-like genes compromise N function and lead to loss-of-resistance to TMV.

To see whether the TMV-GFP is present in the upper uninfiltrated leaves of EDS1, Rar1 and NPR1/NIM1 silenced plants, applicants analysed them for the presence of TMV-GFP RNA. RNA gel blots were prepared from the upper uninfiltrated leaves and probed with the TMV MP gene. As expected, more TMV-GFP RNA was observed in EDS1 (FIG. 9d; lane 4) and Rar1 (FIG. 9d; lane 5) silenced plants than the NPR1 (FIG. 9d; lane 6) silenced plants. The amount of TMV-GFP RNA present in EDS1 and Rar1 silenced plants was less than the amount present in susceptible *N. benthamiana* plants (compare FIG. 9d; lane 1 versus 4 and 5) and more than TRV-N suppressed plants (compare FIG. 9d; lane 3 versus 4 and 5). These results corroborate the phenotypic data that the suppression of Rar1-, EDS1- and NPR1/NIM1-like genes lead to loss-of-resistance to TMV.

To confirm the VIGS of Rar1, EDS1 and NPR1/NIM1 genes at the molecular level, applicants performed semi-quantitative RT-PCR using total RNA extracted from MS4-5 plants infected with TRV, TRV-Rar1, TRV-EDS1 and TRV-NPR1/NIM1. In TRV-Rar1 infected plants, the Rar1 message was reduced by more than 95% compared to the TRV-infected control (FIG. 5e versus FIG. 5f). In TRV-EDS1 and TRVNPR1/NIM1 infected plants, the EDS1 (FIG. 5g versus H) and NPR1/NIM1 (FIG. 5i versus FIG. 5j) messages were reduced by more than 88% and 78%, respectively, compared to the TRV-infected control (FIG. 5a versus FIG. 5b). In all these cases, EF1 a RNA levels were similar (data not shown) and served as an internal control for RNA quality and RT-PCR amplification.

CONCLUSIONS

This example demonstrates that the TRV based systems disclosed herein can be used for VIGS and as an efficient reverse genetics tool to study gene function. Transgenic MS4-5 plants exhibit resistance to TMV by induction of HR lesions and containment of TMV to the infection site similar to wild type N-containing tobacco plants (Whitham et al., 1994) and transgenic N-containing tomato plants (Whitham et al., 1996). Tobacco and *N. benthamiana* belong to the same genus and therefore may contain conserved signal transduction components required for N-mediated resistance to TMV in both species. This is consistent with the observation reported by (Tai et al., 1999) that R genes may function in restricted heterologous species belonging to the same genus or family of plants. In fact, many R genes like pepper BS2, potato Rx1, and tomato Pto and Cf9 function in the heterologous *Nicotiana* host (Bendahmane et al., 1999; Hammond-Kosack et al., 1998; Rommens et al., 1995; Thilmony et al., 1995). Unlike tobacco, *N. benthamiana* plants show less auto-fluorescence under UV illumination and support movement of the TMV-GFP recombinant virus. Therefore, the MS4-5 N-containing *N. benthamiana* transgenic line will be useful in studies aimed towards understanding cellular and physiological events associated with N-mediated HR using TMV-GFP recombinant virus in the future.

Requirement of tobacco Rar1-, EDS1-, and NPR1/NIM1-like genes for the function of the N gene described in this report provide the first evidence for the role of these genes in a viral resistance pathway. From this work and that of others, EDS1 constitutes the converging point of signaling pathways mediated by the functional TIR-NBS-LRR class of R genes. In addition to EDS1, NDR1 is involved in converging race-specific resistance pathways in *Arabidopsis* (Aarts et al., 1998). However, this convergence involves distinct subclasses of NBS-LRR R genes. NDR1 is required for the function of the CC-NBS-LRR class of R genes. Requirement of Rar1 for virus resistance (this report) and some powdery mildew resistance genes in barley (Schulze-Lefert and Vogel, 2000) provide another example of converging points in the disease resistance signaling pathways. Moreover, Rar1 represents the first example of a signalling component shared by CC-NBS-LRR (Mla12) and TIR-NBS-LRR (N) type of race-specific R genes. Our observations suggest that the tobacco NPR1/NIM1-like gene is required for TMV resistance. However, NPR1/NIM1 is not required for function of the HRT-mediated resistance to the virus TCV in *Arabidopsis* (Kachroo et al., 2000). The *Arabidopsis* NPR1/NIM1 has been shown to interact with members of the basic leucine zipper (bZIP) family of transcription factors like TGA2, TGA3 and TGA6 (NIF1) (Despres et al., 2000; Zhang et al., 1999; Zhou et al.,2000). To date, the biological significance of these NPR1/NIM1-TGA interactions is not known. Our VIGS phenotypic data suggests that suppression of individual TGA factors has no effect on N-mediated resistance to TMV (Y.L., M.S., S.P.D-K, unpublished observations). However, suppression of multiple TGA factors simultaneously by mixed infections results in loss-of-resistance to TMV. Further molecular and biochemical analyses of this phenotypic data are necessary to understand the exact role of NPR1-TGA factors in N-mediated resistance to TMV.

Applicants have tested the role of 18 additional candidate genes like SIPK, SIPKK, WIPK, NtMEK1 and NtMEK2, COI1, WRKY factors, etc. Our phenotypic analysis suggests that 10 of these genes may play a role in N-mediated resistance to TMV (Y.L., M.S., and S.P.D-K, unpublished observations). Further functional analysis of these genes at the molecular and biochemical level should help to better understand N mediated signal transduction pathway leading to TMV resistance.

VIGS is known to suppress sequences of highly homologous genes. Therefore, one should be cautious in interpreting VIGS results. In *Arabidopsis*, EDS1, NPR1 and Rar1 are single copy genes. *N. benthamiana* genomic DNA blot analysis suggests that there are two copies of EDS1, NPR1 and Rar1 in this plant. This is consistent with the aneuploidy nature of *N. benthamiana* (1n number=19 chromosome) compared to the diploid members of Nicotiana (1n number=12 chromosome) (Smith, 1979). Therefore, data presented in this report indicates that the Rar1-, EDS1- and NPR1/NIM1-like genes of tobacco are required for function of the N gene.

In RNAi, the RNA degradation is triggered by double stranded RNA (dsRNA) and occurs in a 2-step process. In the first step, double stranded RNA (dsRNA) is processed into shorter, 21-25 nucleotide long sense and antisense units. These small RNAs, called short interfering RNA or siRNA, in the second step act as guide sequences to identify homologous transcripts and target them for destruction (Nishikura, 2001). Recent evidence suggests that there are secondary siRNAs appear to derive from the action of RNA-dependent RNA polymerase (RdRp) (Sijen et al., 2001). The RdRp plays a role in cyclic amplification of initial siRNAs into secondary siRNAs. These secondary siRNAs exhibited a distinct polarity, 5' to 3' on the antisense strand. Therefore, in the future to overcome the silencing of other highly homologous genes, one could target the 5' untranslated region of the gene for silencing.

The availability of the *Arabidopsis* genome sequence (AGI, 2001) and a large number of plant-expressed sequence tags (ESTs) (The Institute of Genomic Research) provide a wealth of information about the plant genome. Therefore, the VIGS assay described here will offer a means to test the function of homologous gene sequences in *N. benthamiana*. Data presented in Example 4 demonstrates that the TRV based VIGS system described here induces efficient gene silencing in other plants as well, including *Arabidopsis* and tomato plants. Therefore, TRV-VIGS will offer an efficient reverse genetics tool to test gene function in different plant systems of choice. Even though the VIGS approach is a rapid method to ascertain function by gene inactivation, one of the main disadvantages is that the phenotype observed is not transmittable to the next generation because of this, it is not possible to perform genetic crosses, suppressor or enhancer screens and other long-term genetic manipulations. However, transgenic expression of a replicating PVX (termed PVX amplicon) containing the plant exon sequence consistently induces the silencing of the corresponding endogenous gene in subsequent generations (Angell and Baulcombe, 1997). Therefore, the generation of a TRV-based amplicon containing transgenic lines of Rar1, EDS1 and NPR1 will provide an invaluable resource for further genetic analyses. So far, Dangl (1999) reports that classical forward genetics screens to identify components of a given resistance response have yielded only a few genes because of redundancy or lethality (Dangl, 1999). The VIGS approach described here may help to overcome this problem because the VIGS 'phenotype' is conditional, loss of mutations due to organismal lethality should not occur. In the future, large-scale screens using a normalized cDNA library in the TRV-based VIGS system, in conjunction with microarray analysis and two-hybrid experiments should facilitate identification of additional components of the defense pathways in plants.

Experimental Procedures

Plasmid Construction pTRV1 (RNA1).

The first strand cDNA of TRV-RNA1 was derived from total RNA extracted from TRV-Ppk20 infected *N. benthamiana* leaves using primer OYL64 (5'-

GGCCCGGGCCCGTTTCGTCCTTTAGGGACTCGTCAGTGTACTGATATAAG

TACAGACGGGCGTAATAACGCTTACGTAGGCGAGGGGTTTTACC-3')

(SEQ ID NO:7) and superscript reverse transcriptase (Gibco/BRL). The primer OYL64 contains an XmaI restriction site (bold), a ribozyme sequence (underlined), and a sequence complementary to TRVRNA1 bases 6755-6791 (italicized). This first strand cDNA was used as template with upstream primer OYL61 (5'-ATAAAA-CATTTCAATCCTTTGAACGCGGTAGAACG-3') (SEQ ID NO:8) corresponding to TRV- RNA1 bases 1-35 and the downstream primer OYL64 to PCR amplify the full-length cDNA of TRV-RNA1. The PCR amplified product was digested by XmaI and cloned into StuI-XmaI-cut pYL44, which is a derivative of pBIN19 binary T-DNA vector (Frisch et al., 1995) carrying the duplicated cauliflower mosaic virus (CaMV) 35S promoter from pCASS2 (Shi et al., 1997) and nopaline synthase (NOS) terminator. The entire sequence of cDNA corresponding to TRV Ppk20 strain RNA1 is deposited in GenBank (AF406990).

pTRV2 (RNA2).

Two cDNA fragments corresponding to bases 1-1646 and 3470-3855 of TRV Ppk20 RNA2 (GenBank Z36974) were amplified by RT-PCR and cloned into StuI-SacI restricted pCASS2 (Shi et al., 1997) to obtain pYL36. During RT-PCR, multiple restriction enzyme sites were included between two fragments at base 1646 for cloning foreign DNA sequences, and a self-cleaving ribozyme sequence was also engineered at the 3'-end of viral RNA2 cDNA. Plasmid pTRV2 was generated by subcloning the HindIII-EcoICR1 restricted fragment of pYL36 into HindIII-HpaI restricted pCAMBIA0390 T-DNA vector. The complete sequence of pTRV2 is deposited in GenBank (AF406991).

pTRV2-derivatives.

The cDNA fragments corresponding to PDS, NPR1/NIM1, Rar1, EDS1 and N were PCR amplified and cloned into pTRV2. A 369-bp fragment of tobacco PDS that corresponds to nt 878-1246 of tomato PDS (GenBank #M88683) was amplified using a forward primer (5'-CTG ACG AGC TTT CGA TGC AGT GCA T-3') (SEQ ID NO: 9) and a reverse primer (5'-ATA TAT GGA CAT TTA TCA CAG GAA C-3') (SEQ ID NO: 10). A 1129-bp fragment corresponding to nt 86-1215 of N cDNA (Whitham et al., 1994) was amplified using a forward primer (5'-ATG GAG CTA TGA TGT TTT CTT AAG TTT TAG-3') (SEQ ID NO:11) and a reverse primer (5'-GAA GGC CTT TAG CAT AAT TTA CTA CCT C-3') (SEQ ID NO:12). A 468-bp fragment corresponding to nt 186-654 of tobacco Rar1 was amplified using primers: 5'-AGG AAA GCA CAC AAC AGA AAA ACC-3' (SEQ ID NO:13) and 5'-GTG CCA TCC TTT GGT GCA TGG AGG-3' (SEQ ID NO:14). A 548-bp fragment corresponding to nt 1290-1837 of tobacco EDS1 was amplified using a forward primer (5'-GAG TAT CAG ACC AAG TGT GAT ATC CG-3') (SEQ ID NO:15) and a reverse primer (5'-GCT GAG GTG GGA GTG TTT TCC ACC-3') (SEQ ID NO:16). A 753-bp fragment corresponding to nt 1014-1767 of tobacco NPR1 was amplified using primers: 5'-GAA AGA GCC TAA AAT TGT AGT GTC-3' (SEQ ID NO:17) and 5'-CTA TTT CCT AAA AGG GAG CTT ATT-3' (SEQ ID NO:18). The identity of these constructs was confirmed by DNA sequencing.

pSPDK661 (TMV-GFP): The TMV cDNA fragment from 30B TMVGFP (Shivprasad et al., 1998) was cloned into pBIN19 derivative pYL44. A ribozyme sequence (Turpen et al., 1993) based on the satellite virusoid of subterranean clover mottle virus was engineered at the 3' end of the TMV cDNA.

pSPDK694 (N gene). The XhoI fragment from pSPDK450 (Dinesh-Kumar and Baker, 2000) was cloned into SalI-cut pCAMBIA2300.

Cloning Rar1-, EDS 1- and NPR1/NIM1-like genes from Tobacco

The 5' and 3' ends of tobacco Rar1, EDS1 and NPR1/NIM1 genes were cloned using SMRT RACE cDNA amplification kit (CLONTECH, Calif., USA). Rar1 5' RACE product was generated using a nested universal primer (NUP) from the kit as a forward primer and a Rar1 gene specific primer (5'-CCT TTC ATC CGG TCA TGG AAG ATA GCG-3') (SEQ ID NO:19) as a reverse primer. Rar1 3' RACE product was generated using a gene specific forward primer (5'-AGG AAA GCA CAC AAC AGA AAA ACC-3') (SEQ ID NO:20) and a universal reverse primer (UPM) from the kit. EDS1 5'-and 3' RACE products were generated using NUP and an EDS1 gene specific primer (5'-GTT TCT TAG TTC CTC CAC TTC TGC-3') (SEQ ID NO:21) and EDS1 gene specific primer (5'-GAG TAT CAG ACC AAG TGT GAT ATC CG-3') (SEQ ID NO:22) and UPM, respectively. NPR1/NIM1 5' RACE product was generated by using NUP and NPR1/NIM1 specific primer (5'-CAA CGT GGA AAG AAG CGT TTT CCA AG-3') (SEQ ID NO:23). NPR1/NIM1 3' RACE product was generated using NPR1/NIM1 specific primer (5'-TCT TGC TAT GGC AGG CGA TGA TTT G-3') (SEQ ID NO:24) and UPM. In all cases, the RACE products were cloned into TOPO cloning vector (INVITROGEN, Carlsbad, Calif., USA). At least 5 independent 5' and 3' RACE clones were sequenced. RACE 5' and 3' overlapping sequences were assembled using the DNA STAR SEQMAN program to obtain full length sequences of Rar1, EDS1 and NPR1/NIM1.

Plant Transformation

N. benthamiana plants were transformed with pSPDK694 using Agrobacterium-mediated leaf disc transformation (Horsch et al., 1985) and kanamycin (150 µg l$^{-1}$) selection. Presence of the transgene was confirmed by PCR using N specific primers.

VIGS Assay and GFP Imaging

N. benthamiana plants were grown in pots at 25° C. in a growth chamber under 16 h light/8 h dark cycle. For VIGS assay, pTRV1 or pTRV2 and its derivatives were introduced into Agrobacterium strain GV2260 by electroporation (BIO-RAD, CA., USA). Agrobacterium cultures at O.D.600=0.8 containing TRV or TRVderivative plasmids were mixed in 1:1 ratio and infiltrated onto the lower leaf of 4-leaf stage plants using a 1-ml needleless syringe. Experiments in which the suppression effect of N, EDS1, Rar1 and NPR1/NIM1 on TMV resistance is investigated, these plants received a secondary infiltration with Agrobacterium cultures at O.D.600=0.5 containing TMV-GFP construct 8 days after TRV infiltration. At this time, TRV-PDS infected plants exhibit silenced phenotype for PDS. Each silencing experiment was repeated at least 5 times and each experiment included at least four independent plants. In experiments where TMV-GFP virus was used, the inoculum was prepared from systemic infected leaves of N. benthamiana plants infiltrated with Agrobacterium containing TMV-GFP plasmid pSPDK661. GFP imaging was done using UV illumination and photographs were taken using OLYMPUS CAMEDIA E10 digital camera.

RNA Isolation, Northern Blot and RT-PCR Analysis

Total RNA was extracted from silenced and non-silenced N. benthamiana plants using RNAwiz solution (Ambion, Tex., USA) and treated with RNase-free DNase (Gene Hunter, Tex., USA). First strand cDNA was synthesized using 10 µg of total RNA, oligo d(T)primer and superscript reverse transcriptase (Gibco/BRL, MD., USA). Semi-quantitative RT-PCR was performed as described in (Burton et al., 2000). For RT-PCR, primers that anneal outside the region targeted for silencing were used to ensure that the endogenous gene is tested. The intensities of PCR generated fragments were analysed and quantified using Gel Doc 2000 and Quantity One Version 4.2.1 (BIO-RAD, CA, USA). RNA blots were prepared using 5 or 10 µg of total RNA following the method described in (Ausubel et al., 1998). To determine TMV or TMV-GFP transcript levels, RNA blots were hybridized with a probe derived from the MP gene of TMV. To determine PR1a message level, a fragment of PR1a derived from tobacco PR1a cDNA (Payne et al., 1988) was used as a probe.

DNA Gel Blot Analysis

The DNA gel blot analysis was performed as described in Dellaporta and Moreno (1994). DNA from *N. benthamiana* was purified using Qiagen plant DNeasy extraction kit. Ten micrograms of genomic DNA was digested with restriction enzymes, fractionated on 0.8% agarose gel, and blotted onto a Zetaprobe membrane (BIO-RAD). The [a-32P]dCTP-labelled probe corresponding to the fragments of EDS1, NPR1 and Rar1 genes used in silencing were made by the random priming method (Pharmacia Corporation, Peapack, N.J., USA).

Example 4

TRV Systems in Tomato

A tobacco rattle virus (TRV)-based VIGS vector for efficient silencing of genes in tomato is described in this example. A modified vector based on the GATEWAY vector system is also described. The modified vector permits efficient cloning of tomato ESTs in a high throughput manner for silencing.

Recombinant TRV Infects Tomato:

The TRV vector system described in Example 3 was tested for its ability to cause systemic infection in tomato. A mixture of *Agrobacterium* cultures containing TRV-RNA1 (pTRV1) and TRV-RNA2 (pTRV2) T-DNA constructs (FIGS. 10*a,b*) was infiltrated onto the lower leaves of 3-week-old Lycopersicon esculentum cultivar VF36 (referred to as VF36) or *L. esculentum* cultivar Micro-tom (referred to as Micro-tom) plants (Scott and Harbaugh, 1989). Ten days post-Agro-infiltration, total RNA was prepared from the upper un-infiltrated leaves. RNA blots were hybridized with probes derived from the 3' ends of RNA1 and RNA2. Genomic RNA1 and 2, and sub-genomic RNA1a and 1b were detected only in those plants infiltrated with *Agrobacterium*-containing TRV clones (FIG. 10*c*; lane 1) and were absent in the control Agro-infiltrated plants (FIG. 10*c*; lane 2). These results clearly showed that recombinant TRV can efficiently replicate and spread systemically in tomato plants.

Silencing of the Tomato PDS Gene Using TRV-VIGS Vector

Figure 12:
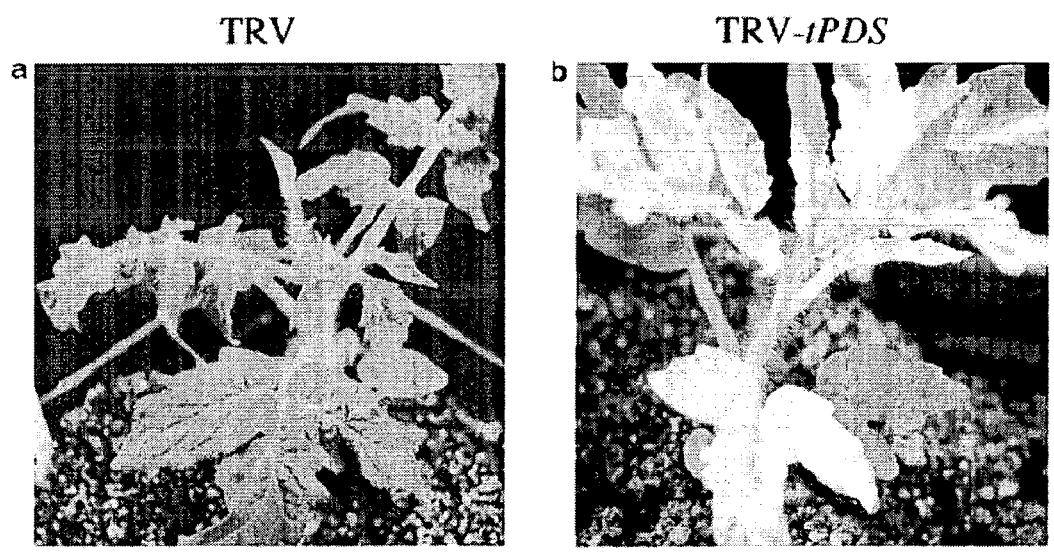
FIG. 12. Silencing of the tomato PDS gene. Infection of tomato plants with recombinant TRV alone (a) or TRV carrying the tomato PDS (TRV-tPDS) (b). Infection with TRV-tPDS silences endogenous PDS in Micro-tom tomato plants and causes inhibition of carotenoid biosynthesis resulting in photo-bleaching phenotype (b).
Figure 13:
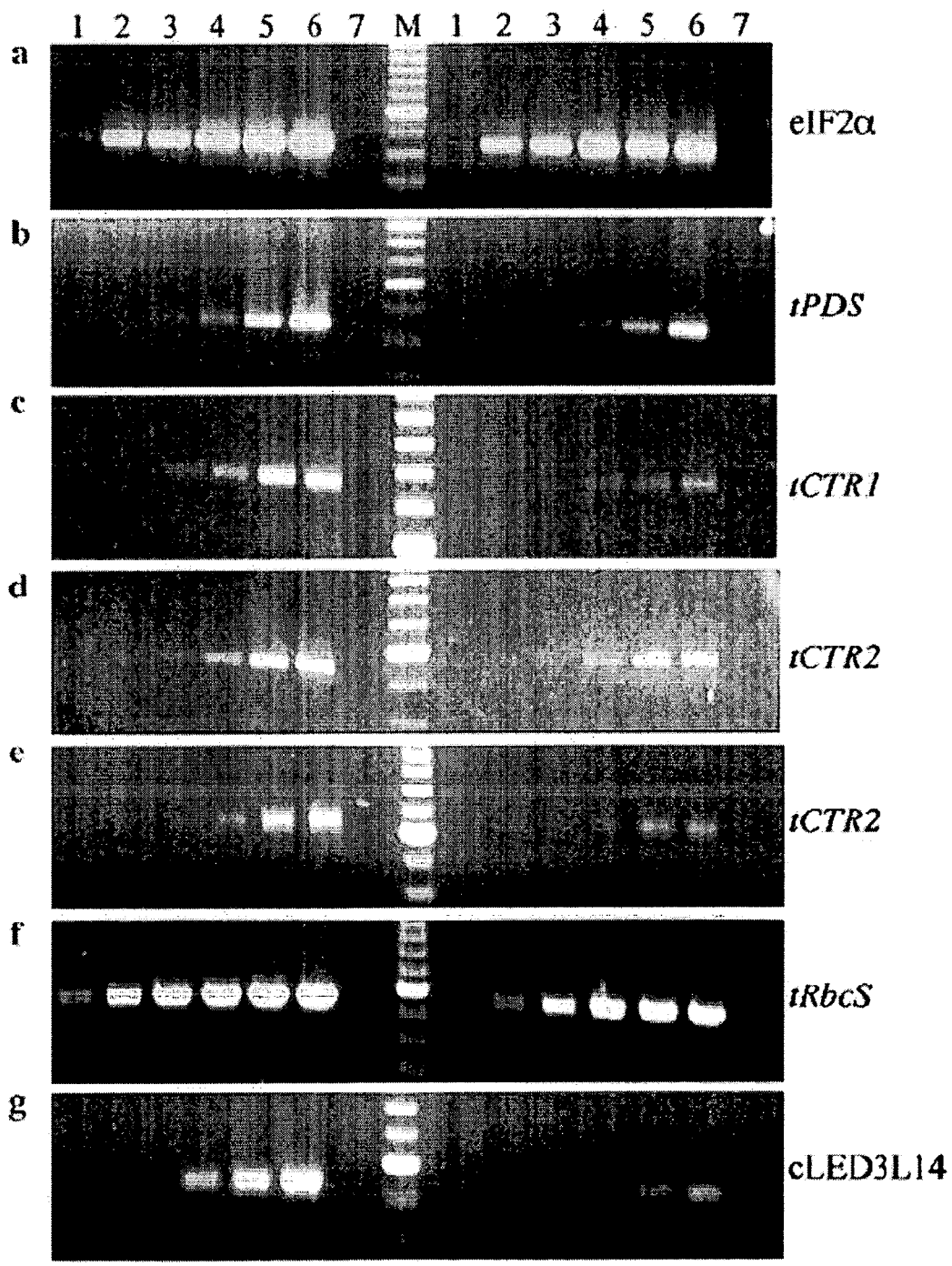
FIG. 13. RT-PCR analysis showing the effect of VIGS on tPDS, tCTR1, tCTR2, tRbcS and EST cLED3L14 transcription. Ethidium bromide-stained agarose gels showing RT-PCR products. The first strand cDNA was generated from total RNA isolated from silenced and non-silenced plants using an oligo (dT) primer and reverse transcriptase. This first strand cDNA was used in a PCR reaction using gene specific primers. (a) Typical PCR products for EF1a derived from TRV alone infected (left) and TRV-VIGS vector-infected (right) tomato plants. (b) Typical PCR products of Micro-tom tomato plants, either PDS silenced (right) or non-silenced, infected with TRV alone (left). (c,d) Typical PCR products for tCTR1 (c) and tCTR2 (d) derived from non-silenced TRV infected (left) and TRV-tCTR1 infected (right) VF36 tomato plants. (e, f, g) Typical PCR products for tCTR2, tRbcS and EST cLED3L14 silenced (right) or non-silenced TRV-alone infected (left) VF36 tomato plants, respectively. Lanes 1-6 correspond to products from PCR cycle number 15, 18, 21, 24, 27, and 30. Lane 7 represents the control, in which the RT reaction mix without reverse transcriptase was used as a template in the reaction. Lane M represents marker.

Next, applicants tested whether the TRV clones could induce gene silencing in tomato plants. In order to do so, applicants examined the ability of the TRV-VIGS vector to suppress the expression of the endogenous phytoene desaturase gene (PDS) in Micro-tom tomato. A mixture of *Agrobacterium* cultures containing pTRV2, carrying tomato PDS (pTRV2-tPDS), and pTRV1, was infiltrated onto the lower leaves of 3-week-old tomato plants (FIG. 11*a*). PDS silencing in *N. benthamiana* inhibits carotenoid biosynthesis, causing the plants to exhibit a photo-bleached phenotype (Kumagi et al., 1995). Tomato plants infected with pTRV-tPDS developed a photo-bleached phenotype in the upper leaves 10 days post-Agro-infiltration and remained white for at least 1 month (FIG. 12). The *Agrobacterium* infiltration method of infecting pTRV-tPDS resulted in the PDS silencing phenotype in only five out of 10 tomato plants (50% efficiency). In contrast, when this technique was applied in *N. benthamiana*, all plants infected with pTRV-NbPDS exhibited PDS silencing. To improve the silencing efficiency, applicants tested a spray technique for the delivery of TRV into tomato plants (FIG. 11*b*). The *Agrobacterium* mixture was sprayed onto 3-week-old tomato plants using an artist's airbrush (see the Experimental procedures section). This method resulted in substantial improvement in the silencing efficiency. Of the 10 plants sprayed with pTRV-tPDS, nine (90%) exhibited the PDS suppression phenotype. These results suggest that spraying *Agrobacterium* is more effective than infiltration in the induction of silencing in tomato plants. Perhaps the *Agrobacterium* infiltration method is not very efficient due to the compact architecture of the young tomato leaves. Additionally, wounding caused by the spray technique may mobilize T-DNA transfer more effectively into the tomato cells. Semi-quantitative RT-PCR was performed to confirm PDS silencing. The primers that anneal to the PDS gene outside the region targeted for silencing were used. In pTRV-tPDS infected plants, the PDS message was reduced by more than 78% compared with the TRV infected controls (FIG. 13*b*). The level of EF1a RNA was similar in TRV-tPDS and TRV alone infected tissue and served as an internal control for RNA quality and RT-PCR amplification (FIG. 13*a*). The level of suppression of PDS in tomato by the TRV-VIGS vector is comparable with PDS silencing in *N. benthamiana*.

The fact that TRV effectively caused the VIGS of PDS in tomato suggests that other nuclear genes could be targeted for silencing in a similar manner. Silencing of the CTR1 homolog in tomato and *N. benthamiana* leads to a constitutive ethylene response phenotype. The phytohormone ethylene participates in a variety of physiological processes in plants including germination, cell elongation, flower and leaf senescence, sex determination, fruit ripening and abscission, wounding and pathogen infection (Abeles et al., 1992; Johnson and Ecker, 1998). In *Arabidopsis*, the CTR1 (constitutive triple response 1) gene encodes a Raf-like mitogen-activated protein kinase kinase kinase (MAPKKK) that functions downstream of an ethylene receptor and negatively regulates the ethylene response (Kieber et al., 1993). The ctr1 loss-of-function mutation confers a phenotype in which plants are severely dwarfed and constitutively express ethylene inducible genes (Kieber et al., 1993). In tomato, there are two CTR1-like genes, tCTR1 (Wang and Li, 1997; Zegzouti et al., 1999) and tCTR2 (AJ005077). tCTR1 is 58% identical and 65% similar to *Arabidopsis* CTR1 at the amino acid level. tCTR2 is 60% identical and 76% similar to tCTR1 in the C-terminus kinase domain but only 38% identical and 55% similar in the N-terminus non-kinase domain. The tCTR2 kinase domain bears a high degree of homology to *Arabidopsis* EDR1 (85% identical) at the amino acid level. The *Arabidopsis* EDR1 gene encodes a putative MAPKKK and the mutant, edr1, has an elevated resistance to *Pseudomonas syringae* and *Erysiphe cichoracearum* (Frye et al., 2001). The biological functions of tCTR1 and tCTR2 in tomato have not been examined.

Figure 14:
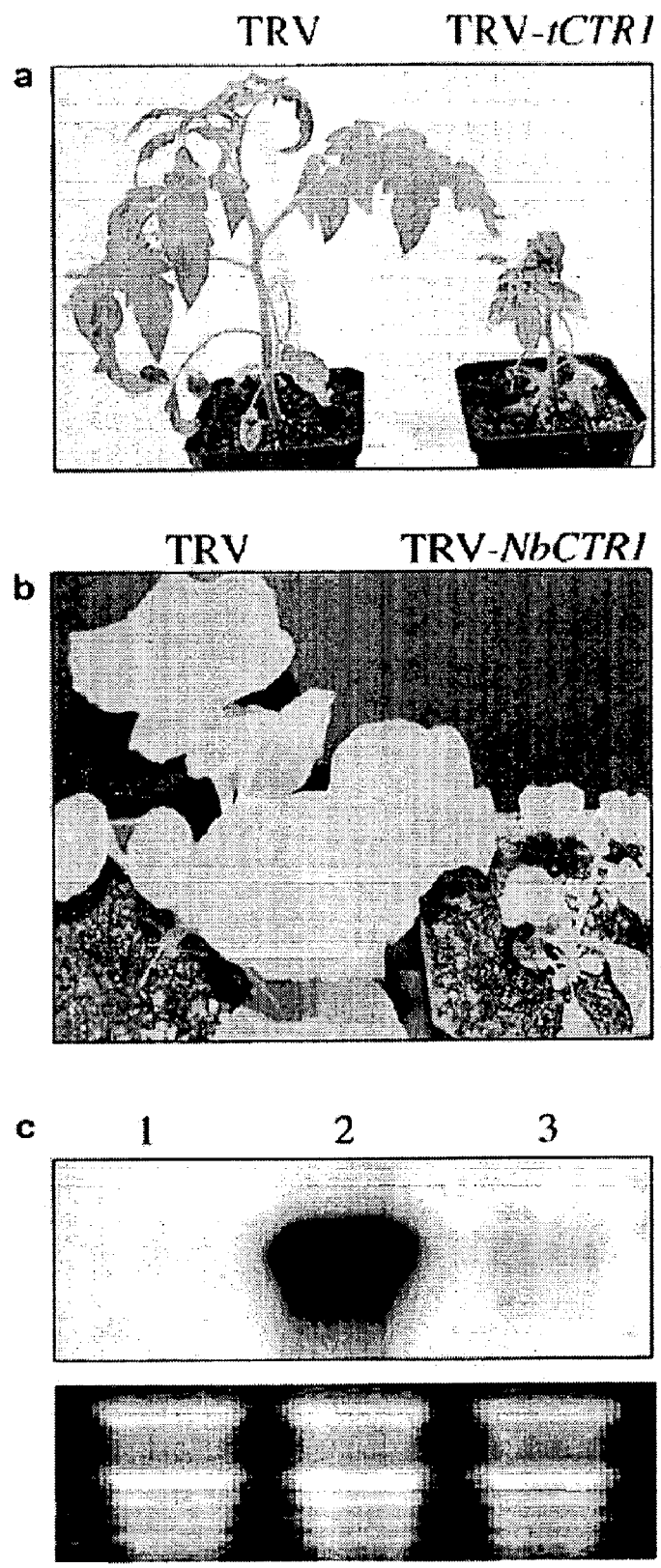
FIG. 14. Silencing of the tomato CTR1 and *N. benthamiana* CTR1 genes. (a) tCTR1 silenced (right) and non-silenced (left) phenotype in VF36 tomato plants. (b) NbCTR1 silenced (right) and non-silenced (left) phenotype in *N. benthamiana* plants. (c) Expression of CHIB gene in wild-type (lane 1), tCTR1-silenced (lane 2) and non-silenced (lane 3) VF36 tomato plants. Ten micrograms of total RNA isolated from these plants was blotted and probed with 32P-labeled CHIB cDNA fragment. The picture of the ethidium bromide-stained gel shown below the blot demonstrates equal loading of RNA.

To examine whether tCTR1 and tCTR2 are true homologs of the *Arabidopsis* CTR1 gene, applicants silenced these genes in tomato and in *N. benthamiana* using the TRVVIGS assay. Suppression of tCTR1 in VF36 tomato plants resulted in a constitutive ethylene response phenotype similar to that observed in *Arabidopsis*. They were severely dwarfed compared with the non-silenced plants (FIG. 14*a*). On the other hand, the suppression of tCTR2 had no effect on plant growth or development (data not shown). Since tomato and tobacco share very high sequence similarity, applicants investigated whether CTR1 homologs of tobacco can induce a similar phenotype in *N. benthamiana*. As expected, suppression of NbCTR1 leads to a severe dwarf phenotype similar to that observed in tomato (FIG. 14*b*) and NbCTR2 suppression had no effect. To confirm the tCTR1 suppression at the molecular level, applicants performed semiquantitative RT-PCR. In TRV-tCTR1 infected plants, the tCTR1 message was reduced by more than 81% compared to the controls infected with TRV alone (FIG. 13c). In both tissue RNA samples, EF1a expression levels were similar (data not shown) and served as an internal control.

Because the region targeted for silencing tCTR1 has 70% similarity to tCTR2 at the nucleotide level, applicants tested whether TRV-tCTR1 could also suppress tCTR2. Semiquantitative RT-PCR analysis-using primers that anneal to tCTR2, showed that the tCTR2 message level is not affected in the TRV-tCTR1 silenced plants (FIG. 13d). To rule out the possibility that the absence of a developmental phenotype in TRV-tCTR2 suppressed plants is due to lack of suppression of endogenous tCTR2, applicants performed semiquantitative RT-PCR analysis. In tCTR2 silenced plants there was an 85% reduction of tCTR2 mRNA compared with the TRV infected control plants (FIG. 13e). These results suggest that tCTR2 is effectively silenced by VIGS although there is no visible phenotype.

The mutation in CTR1 in *Arabidopsis* causes constitutive expression of CHITINASE B (CHIB), an ethylene inducible gene (Kieber et al., 1993). Applicants examined the level of CHIB RNA expression in tCTR1 suppressed tomato plants using RNA blots hybridized with the CHIB gene. CHIB was not detected in wild-type plants (FIG. 14c, lane 1) and very low expression was observed in non-silenced TRV infected plants (FIG. 14c, lane 3). However, in the tCTR1 silenced plants, the CHIB gene was highly expressed (FIG. 14c, lane 2). These results suggest that suppression of tCTR1 in tomato leads to constitutive expression of ethylene-regulated genes. Taken together, these results show that the TRV based VIGS vector can efficiently phenocopy the effects of mutations in different nuclear genes in tomato.

Modification of the TRV2 Vector for High Throughput Cloning.

In the TIGR (The Institute of Genomic Research) database there are over 100 000 tomato ESTs corresponding to 29 000 unique sequence clones (Uni ESTs). Many of these ESTs show homology to genes in *Arabidopsis*. The TRV-VIGS approach described in this example offers great promise for studying tomato Uni-EST function. However, insertion of tomato ESTs into pTRV2 using a traditional cloning method is labor-intensive and time-consuming. Therefore, applicants modified the pTRV2 clone using the GATEWAY system (Invitrogen, Calif., USA). The GATEWAY technology allows fast and easy cloning that is restriction enzyme- and ligation-free. Consequently, the Uni ESTs can be cloned en masse into this pTRV2 vector.

The construct, pTRV2-attP1-attP2, was generated to facilitate en masse cloning of tomato ESTs (FIG. 15a). The PCR products flanked by attB1 and attB2 sequences directionally recombine in vitro at attP1 and attP2 sites contained in the plasmid when incubated with the BP CLONASE enzyme (FIG. 15b). When this reaction mixture is transformed into an *E. coli* strain such as DH10B, only recombinants can grow because the ccdB gene, contained in the plasmid, is lethal. The resulting recombinant plasmid will contain flanking attL1 and attL2 sequences (FIG. 15b). Applicants cloned the *N. benthamiana* PDS gene into the pTRV2-attP1-attP2 vector to test the efficiency of cloning and silencing. Efficiency of cloning a PCR product flanked by attB1 and attB2 into this vector is about 95%. However, when applicants tested this vector for the efficiency of silencing PDS gene in *N. benthamiana*, a very low level of patchy suppression was observed. RT-PCR confirmed that the clone was infectious, but the PCR fragment obtained from amplification of RNA extracted from infected plants was smaller than expected. Since, both attL1 and attL2 sequences are direct repeats of 100 bp, applicants reasoned that PDS flanked by these repeat sequences may have been deleted upon infection of plants with the vector, and failure to suppress PDS would result.

In order to overcome this deletion problem, applicants generated the vector pTRV2-attR2-attR1 (FIG. 16a). In the first step, the PCR products flanked by attB1 and attB2 sequences directionally recombine in vitro at attP1 and attP2 sites on the pDONR-mod plasmid when incubated with the BP CLONASE enzyme (FIG. 16b). In the second step, the intermediate attL1-attL2-containing pDONR-mod vector directionally recombines with attR2 and attR1 sites in the pTRV2 vector, when incubated with the LR CLONASE enzyme. (FIG. 7b). Therefore, the resulting plasmid has only a 23-bp flanking sequence of attB1 and attB2. Moreover, these sequences are not direct repeats. The efficiency of cloning a target sequence for silencing into this vector is about 90%.

Figure 17:
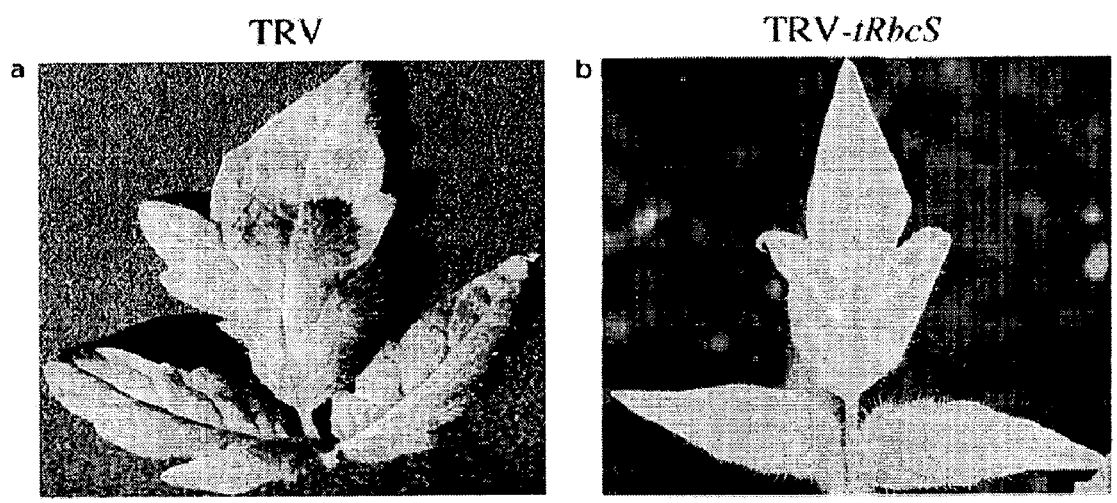
FIG. 17. Silencing of the tomato RbcS using the pTRV2 GATEWAY vector. Infection of VF36 tomato plants with recombinant TRV GATEWAY alone (a) or TRV GATEWAY carrying the tomato RbcS (TRV-tRbcS) (b). Infection with TRV-tRbcS silences endogenous RbcS and causes development of pale yellow leaves (b).

To determine whether the pTRV2-attR2-attR1 vector efficiently mediates gene silencing similar to original pTRV2 vector, applicants cloned PDS and the small sub-unit of the ribulose bisphosphate carboxylase (tRbcS). Compared with PDS, the RbcS is encoded by a multigene family and is expressed in abundance. The efficiency of silencing PDS was similar to that of the original pTRV2 vector. The tRbcS silenced plants developed pale yellow leaves 12 days post-Agro-infiltration compared to the TRV alone infected control plants (FIG. 17). This phenotype is similar to that reported by Ratcliff et al. (2001) in *N. benthamiana*. Furthermore, semiquantitative RT-PCR analysis suggests that the endogenous tRbcS mRNA is reduced by 76% compared with the TRV infected control plants (FIG. 13f).

In order to demonstrate that tomato ESTs can be easily cloned into the pTRV2-attR2-attR1 destination vector, applicants cloned 10 tomato ESTs that bear homology to a serine/threonine kinase (The Institute of Genomic Research). Primer sequences were designed that annealed to vector sequences flanking the tomato ESTs. The attB1 sequence was included in the forward primer and the attB2 sequence was included in reverse primer (FIG. 16b). These primer sets were then used to amplify ESTs by PCR (FIG. 16c). The PCR products with terminal attB1 and attB2 sequences were incubated with the pDONR-mod vector containing the attP1 and attP2 recombination site and the BP CLONASE enzyme. The pTRV2-attR2-attR1 destination vector containing the attR1 and attR2 recombination site and the LR CLONASE enzyme were added. This mixture was transformed into DH10B chemical competent cells and selected on kanamycin-containing LB plates. This single-tube protocol for cloning attB-PCR products directly into pTRV2-attR2-attR1 resulted in a 95-100% success rate. Inserts containing clones were verified by restriction enzyme digestion (FIG. 16d) and by sequencing the vector-insert junctions. These results suggest that tomato ESTs can be cloned into the pTRV2-attR2-attR1 vector for silencing en masse.

In order to demonstrate that the above described TRV-EST clones can be used for silencing corresponding endogenous genes, applicants silenced EST cLED3L14 (TIGR) (corresponding PCR product and the clone is shown in FIGS. 16c,d; lane 2). This EST shows highest homology to potato protein kinase StCPK1 (Lakatos et al., 1998). Suppression of the endogenous gene corresponding to this EST showed no visible phenotype (data not shown) even though the mRNA is reduced by 82% compared with the TRV-alone control (FIG. 4g). These results indicate that the tomato EST clones in TRV-attR2-attR1 vector can be used successfully to silence corresponding endogenous genes in tomato.

CONCLUSIONS

Gene silencing methods that do not rely on transformation offer a tremendous advantage for gene function analysis. In this report applicants show that recombinant TRV infects tomato plants and can be used to silence genes efficiently. The results suggest that a spray technique to deliver *Agrobacterium* to tomato plant cells is better for obtaining high efficiency silencing compared with the routinely used *Agrobacterium* infiltration method. Using this TRV-based VIGS system, applicants demonstrate that tCTR1 is a true homolog of the *Arabidopsis* CTR1 gene. Suppression of tCTR1 in tomato and *N. benthamiana* induces a constitutive ethylene response phenotype, while suppression of tCTR2 does not. Even though TCTR1 and tCTR2 share up to 60% sequence similarity at the nucleotide level, suppression of tCTR1 using the VIGS vector had no effect on tCTR2 gene expression. Finally, applicants have modified the TRV2 vector using the GATEWAY recombination system in order to clone tomato ESTs en masse with one set of primers. This provides a rapid way to test tomato EST function. Using this vector, applicants show that tRbcS and an endogenous gene corresponding to tomato EST cLED3L14 can be successfully silenced. Therefore, the modified TRV2 vector will facilitate production of normalized cDNA libraries or the cloning of large sets of genes for large-scale functional genomics in the future.

Experimental Procedures

Plasmid Construction:

pTRV1 and pTRV2 VIGS vectors are described in Example 3.

pTRV2-tPDS: a 409-bp fragment of PDS cDNA fragment corresponding to bases 858-1266 of tomato PDS gene was PCR amplified from tomato VF36 cDNA using Taq DNA polymerase and the primers 5'-CGG TCT AGA GGC ACT CAA CTT TAT AAA CC-3' (SEQ ID NO:25) and 5'-CGG GGA TCC CTT CAG TTT TCT GTC AAA CC-3' (SEQ ID NO:26). The resulting PCR product was cloned into XbaI-BamHI-cut pTRV2.

pTRV2-tCTR1: a 690-bp fragment of tCTR1 cDNA fragment corresponding to bases 1906-2595 of tomato CTR1 (Wang and Li, 1997) was PCR amplified from tomato VF36 cDNA using Taq DNA polymerase and the primers 5'-CGG GAA TTC GTT GCA ATT ATC AAG CGG TTG CG-3' (SEQ ID NO:27) and 5'- CGG CTC GAG TCA TGA GAG CAA CTG CAT GTC TG T-3' (SEQ ID NO:28). The resulting PCR product was cloned into EcoRI-XhoI-cut pTRV2.

pTRV2-tCTR2: a 537-bp fragment of CTR2 cDNA fragment corresponding to bases 2506-3042 of tomato CTR2 (GenBank #AJ005077) was PCR amplified from tomato VF36 cDNA using Taq DNA polymerase and the primers 5'-CGG GAA TTC GCC CTT GAT GTG GCA AAG GGC AT-3' (SEQ ID NO:29) and 5'-CGG CTC GAG GTA GAA TTT ACT GAG ATT TCC TG-3' (SEQ ID NO:30). The resulting PCR product was cloned into EcoRI-XhoI-cut pTRV2.

pTRV2-NbCTR1: a 690-bp of CTRI cDNA fragment was PCR amplified from *N. benthamiana* cDNA using Taq DNA polymerase and the primers used to amplify tCTR1. The resulting PCR product was cloned into EcoRI-XhoI-cut pTRV2.

pTRV2-NbCTR2: a 537-bp of CTR2 cDNA fragment was PCR amplified from *N. benthamiana* cDNA using Taq DNA polymerase and the primers used to amplify tCTR2. The resulting PCR product was cloned into EcoRI-XhoI-cut pTRV2.

pTRV2-attP1-attP2: The DNA fragment containing attP1-ccdBCmR.- attP2 amplified from pDONR201 (Invitrogen, Carlsbad, Calif., USA) using primers 5'-CGG GAA TTC TAG AGG CGC GCC AAA TAA TGA TTT TAT TTT GAC TGA TAG TGA C-3' (SEQ ID NO:31) and 5'-C GGC TCG AGA GCT CAA ATA ATG ATT TTA TTT TGA CTG ATA GTG AC-3' (SEQ ID NO:32). This PCR product was cloned into EcoRI-XhoI-cut pTRV2 (Liu et al., 2002).

pDONR-mod: This vector was generated by deleting the fragment containing the kanamycin gene between PvuI and NruI of pDONR201 (Invitrogen) and religating the vector.

pTRV2-attR2-attR1: HindIII-DraIII(T4 DNA polymerase treated) fragment of pYL156 (Liu et al., 2002) containing 2×CaMV promoter and TRV-RNA2 cDNA with the NOS terminator was cloned into pBin19 to obtain pYL276. pTRV2-attR1-attR2 was obtained by inserting the GATEWAY conversion cassette B (Invitrogen) into pYL276 at the StuI site.

pTRV2-attL1-NbPDS-attL2 and pYL157: *N. benthamiana* PDS cDNA containing the attB1 and attB2 sequences was obtained by PCR amplification using the TRV-PDS clone (Liu et al., 2002) as template and primers: 5'-G GGG ACA AGT TTG TAC AAA AAA GCA GGC TCT GAC GAG CTT TCG ATG CAG-3' (SEQ ID NO:33) and 5'-GGG GAC CAC TTT GTA CAA GAA AGC TGG GTA TAT ATG GAC ATT TAT CAC A-3' (SEQ ID NO:34). This PDS PCR product was recombined into pTRV2-attP1-attP2 using the BP CLONASE enzyme reaction (Invitrogen).

pTRV2-attB2-NbPDS-attB1: *N. benthamiana* PDS cDNA containing the attB1 and attB2 sequences was obtained by PCR, as described above. This PDS PCR product was recombined into pDONR-mod vector containing the attP1 and attP2 recombination sites using the BP CLONASE enzyme. To this, the pTRV2-attR1-attR2 destination vector and the LR CLONASE enzyme was added. This mixture was transformed into DH10B chemical competent cells and selected on kanamycin-containing LB plates.

pTRV2-attB2-tRbcS-attB1: A 500-bp tRbcS cDNA containing the attB1 and attB2 sequences was obtained by PCR using VF36 cDNA and primers 5'-GGG GAC AAG TTT GTA CAA AAA AGC AGG CTC TGC TTC CTC TGT CAT TTC TTC AGC-3' (SEQ ID NO:35) and 5'-GGG GAC CAC TTT GTA CAA GAA AGC TGG GTC CAC TTG ACG CAC ATT GTC GAA TCC-3'(SEQ ID NO:36). This PCR product was recombined into pTRV2-attR2-attR1 vector as described above for cloning PDS.

pTRV2-attB2-tomato ESTs-attB1: 10 tomato ESTs that bear homology to serine/threonine kinases were amplified by PCR using a forward primer containing the attB1 sequence and a reverse primer containing the attB2 sequence, which anneals to the vector pBluescript SK (−) containing tomato ESTs. The forward primer is 5'-G GGG ACA AGT TTG TAC AAA AAA GCA GGC TCC CCC GGG CTG CAG GAA TTC-3' (SEQ ID NO:37) and the reverse primer is G GGG ACC ACT TTG TAC AAG AAA GCT GGG TGG TAC CGG GCC CCC CCT CGA G-3' (SEQ ID NO:38). The resulting PCR products with terminal attB1 and attB2 sequences were precipitated and incubated with pDONR-mod vector containing the attP1 and attP2 recombination sites and the BP CLONASE enzyme. To this, the pTRV2-attR2-attR1 destination vector containing the attR1 and attR2 recombination sites and the LR CLONASE enzyme was added. This mixture was transformed into DH10B chemical competent cells and selected on kanamycin-containing LB plates. Clones were verified by restriction enzyme digestion and by sequencing the vector-insert junctions.

Agro-infiltration and Spray

N. benthamiana and tomato plants were grown in pots at 25° C. in a growth chamber under 16 h light/8 h dark cycle with 60% humidity. For the VIGS assay, pTRV1 or pTRV2 and its derivatives were introduced into Agrobacterium strain GV3101 by electroporation (BIO-RAD, Hercules, Calif., USA). A 5-ml culture was grown overnight at 28° C. in the appropriate antibiotic selection medium. The next day, the culture was inoculated into a 50-ml LB medium containing antibiotics, 10 mM MES and 20 mM acetosyringone. The culture was grown overnight in a 28° C. shaker. Agrobacterium cells were harvested and resuspended in infiltration media (10 mM MgCl2, 10 mM MES, 200 mM acetosyringone), adjusted to an O.D. of 2.0 and left at room temperature for 3 h. Agrobacterium was infiltrated using a needleless 1 ml syringe or sprayed using an artist's airbrush (Paasche, Harwood Heights, Ill., USA, model VL80) connected to a portable air compressor (Campbell Havsfeld, Harrison, Ohio, USA) set at 75 psi. Plants were left covered overnight.

RNA Isolation, Northern Blot and RT-PCR Analysis

Total RNA was extracted from silenced and non-silenced tomato plants using the RNAwiz solution (Ambion, Austin, Tex., USA) and treated with RNase-free DNase (Gene Hunter, Nashville, Tenn., USA). First strand cDNA was synthesized using 1 µg of total RNA, oligo d(T)primer and superscript reverse transcriptase (Invitrogen). Semi-quantitative RT-PCR was performed as described in (Burton et al., 2000; Liu et al., 2002). For RT-PCR, primers that anneal outside the region targeted for silencing were used to ensure that only the endogenous gene was being tested. The intensities of PCR-generated fragments were analyzed and quantified using Gel Doc 2000 and Quantity One Version 4.3 (BIORAD, CA).RNA blots were prepared using 5 or 10 µg of total RNA. To confirm TRV infection, RNA blots were hybridized with a probe derived from the 3'-end of TRV RNA1 (bases 5351-6791) and RNA2 (bases 1245-2103). To determine the CHIB message level, a fragment of CHIB was PCR amplified from tomato cDNA using primers 5'-ACT GTT TCC TTA GAG AGC AAG GTA G-3 (SEQ ID NO:39)' and 5'-CAA CTA ATA GTC CGT TTC CAA AAG ACC-3' (SEQ ID NO:40) and this fragment was used as a probe.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

Aarts, N., Metz, M., Holub, E., Staskawicz, B. J., Daniels, M. J. and Parker, J. E. (1998) Different requirements for EDS1 and NDR1 by disease resistance genes define at least two R gene mediated signaling pathways in Arabidopsis. Proc. Natl Acad.Sci. USA 95, 10306-10311.

Angell, S. and Baulcombe, D. (1997) Consistent gene silencing in transgenic plants expressing a replicating potato virus X RNA. EMBO J. 16, 3675-3684.

Ausubel, F. M., Brent, R., Kingston, R. E., Moore, D. D., Seidman, J. G., Smith, J. A. and Struhl, K. (1998) Current Protocols in Molecular Biology. New York, N.Y.: Greene and Wiley Interscience.

Baulcombe, D. C. (1999) Fast forward genetics based on virus induced gene silencing. Curr. Op. Plant Biol. 2, 109-113.

Bendahmane, A., Kanyuka, K. and Baulcombe, D. C. (1999) The Rx1 gene from potato controls separate virus resistance and cell death responses. Plant Cell, 11, 781-791.

Burton, R. A., Gibeaut, D. M., Bacic, A., Findlay, K., Roberts, K., Hamilton, A., Baulcombe, D. C. and Fincher, G. B. (2000) Virus induced silencing of a plant cellulose synthase gene. Plant Cell 12, 691-705.

Cao, H., Glazebrook, J., Clarke, J. D., Volko, S. and Dong, X. (1997) The Arabidopsis NPR1 gene that controls systemic acquired resistance encodes a novel protein containing ankyrin repeats. Cell 88, 57-63.

Dangl, J. (1999) Long view from a high plateau. Nature 401, 543-544.

Dellaporta, S. L. and Moreno, M. A. (1994) Southern blot hybridization. The Maize Handbook (Freeling M. and Walbot V., eds), pp. 569-572.

Despres, C., DeLong, C., Glaze, S., Liu, E. and Fobert, P. R. (2000) The Arabidopsis NPR1/NIM1 protein enhances the DNA binding activity of a subgroup of the TGA family of bZIP transcription factors. Plant Cell 12, 279-290.

Dinesh-Kumar, S., P. and Baker, B. (2000) Alternatively spliced N resistance gene transcripts: Their possible role in tobacco mosaic virus resistance. Proc. Natl Acad. Sci. USA 97, 1908-1913.

Dinesh-Kumar, S. P. Tham, W.-H. and Baker, B. (2000) The structure-function analysis of the tobacco mosaic resistance gene N. Proc. Natl Acad. Sci. USA 97, 14789-14794.

Falk, A. Feys, B. J. Frost, L. N. Jones, J. D. G. Daniels, M. J. and Parker, J. E. (1999) EDS1, an essential component of R. gene mediated disease resistance in Arabidopsis has homology to eukaryotic lipases. Proc. Natl Acad. Sci. USA 96, 3292-3297.

Frisch, D. A. Harris-Haller, L. W. Yokubaitis, N. T. Thomas, T. L. Hardin, S. H. and Hall, T. C. (1995) Complete sequence of the binary vector Bin19. Plant Mol. Biol. 27, 405-409.

Hammond-Kosack, K. E. Tang, S. Harrison, K. and Jones, J. D. (1998) The tomato Cf-9 disease resistance gene functions in tobacco and potato to confer responsiveness to the fungal avirulence gene product avr 9. Plant Cell 10, 1251-1266.

Holmes, F. O. (1934) Inheritance of ability to localize tobacco mosaic virus. Phytopathology 24, 984-1002.

Hooft van Huijsduijnen, R. A. M. van Loon, L. C. and Bol, J. F. (1986) cDNA cloning of six mRNAs induced by TMV infection of tobacco and a characterization of their translation products. EMBO J. 5, 2057-2061.

Horsch, R. B. Fry, J. E. Hoffmann, N. L. Eichholtz, D. Rogers, S. G. and Fraley, R. T. (1985) A simple and general method for transferring genes into plants. Science 227, 1229-1231.

Kachroo, P. Yoshioka, K. Shah, J. Dooner, H. K. and Kiessig, D. F. (2000) Resistance to turnip crinkle virus in Arabidopsis is regulated by two host genes and is salicylic acid dependent but NPR1, ethylene, and jasmonate independent. Plant Cell 12, 677-690.

Kinkema, M. Fan, W. and Dong, X. (2000) Nuclear localization of NPR1 is required for activation of PR gene expression. Plant Cell 12, 2339-2350.

Kumagai, M. H. Donson, J. Dellacioppa, G. Harvey, D. Hanley, K. and Grill, L. K. (1995) Cytoplasmic inhibition of carotenoid biosynthesis with virus-derived RNA. Proc. Natl Aacd. Sci. USA 92, 1679-1683.

MacFarlane, S. A. (1999) Molcecular biology of the tobraviruses. J. General Virol. 88, 2799-2807.

Nishikura, K. (2001) A short primer on RNAi: RNA-directed RNA polymerase acts as a key catalyst. Cell 107, 415-418.

Payne, G. Parks, T. D. Burkhart, W. Dincher, W. Ahl, P. Metraux, J. P. and Ryals, J. (1988) Isolation of the genomic clone for pathogenesis-related protein 1a from *Nicotiana tabacum* cv. Xanthi-nc. Plant Mol. Biol. 11, 89.

Ratcliff, F. Martin-Hernandez, A. M. and Baulcombe, D. C. (2001) Tobacco rattle virus as a vector for analysis of gene function by silencing. Plant J. 25, 237-245.

Ratcliffe et al. U.S. Pat. No. 6,369,296

Rommens, C. M. T. Salmeron, J. M. Baulcombe, D. C. and Staskawicz, B. J. (1995) Use of a gene expression system based on potato virus X to rapidly identify and characterize a tomato Pto homolog that controls fenthion sensitivity. Plant Cell 7, 249-257.

Schulze-Lefert, P. and Vogel, J. (2000) Closing the ranks to attack by powdery mildew. Trends Plant Sci. 5, 343-348.

Shi, B.-J. Ding, S.-W. and Symons, R. H. (1997) Plasmid vector for cloning infectious cDNAs from plant RNA viruses: high infectivity of cDNA clones of tomato aspermy cucumovirus. J. General Virol. 78, 1181-1185.

Shirasu, K. Lahaye, T. Tan, M.-W. and Schulze-Lefert, P. (1999) A novel class of eukaryotic zinc-binding proteins is required for disease resistance signaling in barley and development in *C. elegans*. Cell 99, 355-366.

Shivprasad, S. Pogue, G. P. Lewandowski, D. J. Hidalgo, J. Donson, J. Grill, L. K. and Dawson, W. O. (1998) Heterologous sequences greatly affect foreign gene expression in tobacco mosaic virus-based vectors. Virology 255, 312-323.

Sijen, T. Fleenor, J. Simmer, F. Thijssen, K. L. Parrish, S. Timmons, L. Plasterk, R. H. A. and Fire, A. (2001) On the role of RNA amplification in dsRNA-triggered gene silencing. Cell 107, 465-476.

Smith, H. H. (1979) The *Nicotiana* genus as a genetic resource. USDA Techn Bull. No. 1586, 1-16.

Tai, T. H. Dahlbeck, D. Clark, E. T. Gajiwala, P. Pasion, R. Whalen, M. C. Stall, R. E. and Staskawicz, B. J. (1999) Expression of the Bs2 pepper gene confers resistance to bacterial spot disease in tomato. Proc. Natl Acad. Sci. USA 96, 14153-14158.

Thilmony, R. L., Chen, Z., Bressan, R. A. and Martin, G. B. (1995) Expression of the tomato Pto gene in tobacco enhances resistance to *Pseudomonas syringae* pv. tabaci expressing avrpto. Plant Cell 7, 1529-1536.

Turpen, T. H., Turpen, A. M., Weinzettl, N., Kumagai, M. H. and Dawson, W. O. (1993) Transfection of whole plants from wounds inoculated with *Agrobacterium tumefaciens* containing cDNA of tobacco mosaic virus. J. Virol. Meth. 42, 227-239.

Ward, E. R., Uknes, S. J., Williams, S. C., Dincher, S. S., Wiederhold, D. L., Alexander, D. C., Ahl-Goy, P., Metraux, J.-P. and Ryals, J. A. (1991) Coordinate gene activity in response to agents that induce systemic acquired resistance. Plant Cell 3, 1085-1094.

Whitham, S., Dinesh-Kumar, S. P., Choi, D., Hehl, R., Corr, C. and Baker, B. (1994) The product of the tobacco mosaic virus resistance gene N: similarity to toll and the interieukin-1 receptor. Cell 78, 1101-1115.

Whitham, S., McCormick, S. and Baker, B. (1996) The N gene of tobacco confers resistance to tobacco mosaic virus in transgenic tomato. Proc. Natl Acad. Sci. USA 93, 8776-8781.

Zhang, Y., Fan, W., Kinkema, M., Li, X. and Dong, X. (1999) Interaction of NPR1 with basic leucine zipper protein transcription factors that bind sequences required for salicylic acid induction of the PR1 gene. Proc. Natl Acad. Sci. USA 96, 6523-6528.

Zhou, J.-M., Trifa, Y., Silva, H., Pontier, D., Lam, E., Shah, J. and Klessig, D. F. (2000) NPR1 differentially interacts with members of the TGA/OBF family of transcription factors that bind an element of the PR-1 gene required for induction by salicylic acid. Mol. Plant Microbe Interact. 13, 191-202.

Wang, Y. and Li, N. (1997) A cDNA sequence isolated from the ripening tomato fruit encodes a putative protein kinase. Plant Physiol. 114, 1135.

Waterhouse, P. M., Graham, M., W. and Wang, M.-B. (1998) Virus resistance and gene silencing in plants is induced by double stranded RNA. Proc. Natl Acad. Sci. 95, 13959-13964.

Waterhouse, P. M., Wang, M.-B. and Lough, T. (2001) Gene silencing as an adaptive defense against viruses. Nature, 411, 834-842.

Zegzouti, H., Jones, B., Frasse, P., Marty, C., Maitre, B., Latche, A., Pech, J.-C. and Bouzayen, M. (1999) Ethylene-regulated gene expression in tomato fruit: characterization of novel ethylene responsive ripening related genes isolated by differential display. Plant J. 18, 589-600.

Abeles, F. B., Morgan, P. W. and Salveit, M. E. (1992) Ethylene in Plant Biology 2nd edn. New York, USA: Academic Press.

Frye, C. A., Tang, D. and Innes, R. W. (2001) Negative regulation of defense responses in plants by a conserved MAPKK kinase. Proc. Natl Acad. Sci. 98, 373-378.

Johnson, P. R. and Ecker, J. R. (1998) The ethylene gas signal transduction pathway: a molecular perspective. Annu. Rev. Genet. 32, 227-254.

Lakatos, L., Hutvagner, G. and Banfalvi, Z. (1998) Potato protein kinase StCPK1: a putative evolutionary link between CDPKs and CRKs. Biochim. Biophys. Acta, 1442, 101-108.

Martienssen, R. A. (1998) Functional genomics: Probing plant gene function and expression with transposons. Proc. Natl Acad. Sci. 95, 2021-2026.

Meissner, R., Chague, V., Zhu, Q., Emmanuel, E., Elkind, Y. and

Levy, A. A. (2000) A high throughput system for transposon tagging and promoter trapping in tomato. Plant J. 22, 265-274.

Scott, J. W. and Harbaugh, B. K. (1989) Micro-Tom—a miniature dwarf tomato. Florida Agr. Expt. Sta. Circ. 370, 1-6.

Speulman, E., Metz, P. L. J., van Arkel, G., Hekkert, B. L., Stiekema, W. J. and Pereira, A. (1999) A two-component enhancer inhibitor transposon mutagenesis system for functional analysis of the *Arabidopsis* genome. Plant Cell, 11, 1853-1866.

While specific embodiments of the subject inventions have been discussed, the above specification is illustrative and not restrictive. Many variations of the inventions will become apparent to those skilled in the art upon review of this specification and the claims below. The full scope of the inventions should be determined by reference to the claims, along with their full scope of equivalents, and the specification, along with such variations.

We claim:

1. A plant comprising:
   a) a first recombinant nucleic acid comprising the TRV-RNA1 nucleotide sequence of SEQ ID NO:1; and
   b) a second recombinant nucleic acid comprising the TRV-RNA2 nucleotide sequence of SEQ ID NO:5 and a heterologous nucleotide sequence.

2. A method for making a transgenic plant, the method comprising introducing into one or more cells of the plant:
   a) a recombinant nucleic acid comprising the TRV-RNA1 nucleotide sequence; and
   b) a recombinant nucleic acid comprising the TRV-RNA2 nucleotide sequence of SEQ ID NO:5, and a heterologous nucleotide sequence.

3. The method of claim 2, further comprising generating offspring from the plant.

4. The method of claim 3, wherein the plant is transiently transformed.

5. A transgenic plant produced by the method of claim 3.

6. A method for making a transgenic plant, the method comprising: introducing a recombinant nucleic acid comprising (a) the TRV-RNA2 nucleotide sequence of SEQ ID NO:5, and (b) a heterologous nucleotide sequence, into one or more cells of a plant that is stably transformed with a recombinant nucleic acid comprising a TRV-RNA1 nucleotide sequence.

7. The method of claim 6, wherein the plant is transiently transformed with the recombinant nucleic acid comprising (a) the TRV-RNA2 nucleotide sequence of SEQ ID NO:5, and (b) a heterologous nucleotide sequence.

8. The method of claim 6, wherein the plant is transformed with a vector comprising (a) the TRV-RNA2 nucleotide sequence of SEQ ID NO:5, and (b) the heterologous nucleotide sequence.

9. The method of claim 6, wherein the heterologous nucleotide sequence includes a gene silencing insert.

* * * * *

SEQUENCE LISTING

<160> NUMBER OF SEQ ID NOS: 40

<210> SEQ ID NO 1
<211> LENGTH: 6791
<212> TYPE: DNA
<213> ORGANISM: Tobacco rattle virus

<400> SEQUENCE: 1

```
ataaaacatt tcaatccttt gaacgcggta gaacgtgcta attggatttt ggtgagaacg     60
cggtagaacg tacttatcac ctacagtttt attttgtttt tctttttggt ttaatctatc    120
cagcttagta ccgagtgggg gaaagtgact ggtgtgccta aaacctttc tttgatactt    180
tgtaaaaata catacagata caatggcgaa cggtaacttc aagttgtctc aattgctcaa    240
tgtggacgag atgtctgctg agcagaggag tcatttcttt gacttgatgc tgactaaacc    300
tgattgtgag atcgggcaaa tgatgcaaag agttgttgtt gataaagtcg atgacatgat    360
tagagaaaga aagactaaag atccagtgat tgttcatgaa gttctttctc agaaggaaca    420
gaacaagttg atggaaattt atcctgaatt caatatcgtg tttaaagacg acaaaaacat    480
ggttcatggg tttgcggctg ctgagcgaaa actacaagct ttattgcttt tagatagagt    540
tcctgctctg caagaggtgg atgacatcgg tggtcaatgg tcgttttggg taactagagg    600
tgagaaaagg attcattcct gttgtccaaa tctagatatt cgggatgatc agagagaaat    660
ttctcgacag atatttctta ctgctattgg tgatcaagct agaagtggta agagacagat    720
gtcggagaat gagctgtgga tgtatgacca atttcgtgaa aatattgctg cgcctaacgc    780
ggttaggtgc aataatacat atcagggttg tacatgtagg ggtttttctg atggtaagaa    840
gaaaggcgcg cagtatgcga tagctcttca cagcctgtat gacttcaagt tgaaagactt    900
gatggctact atggttgaga agaaaactaa agtggttcat gctgctatgc tttttgctcc    960
tgaaagtatg ttagtggacg aaggtccatt accttctgtt gacggttact acatgaagaa   1020
gaacgggaag atctatttcg gttttgagaa agatccttcc ttttcttaca ttcatgactg   1080
ggaagagtac aagaagtatc tactggggaa gccagtgagt taccaaggga atgtgttcta   1140
cttcgaaccg tggcaggtga gaggagacac aatgcttttt tcgatctaca ggatagctgg   1200
agttccgagg aggtctctat catcgcaaga gtactaccga agaatatata tcagtagatg   1260
ggaaaacatg gttgttgtcc caattttcga tctggtcgaa tcaacgcgag agttggtcaa   1320
gaaagacctg tttgtagaga aacaattcat ggacaagtgt ttggattaca tagctaggtt   1380
atctgaccag cagctgacca taagcaatgt taaatcatac ttgagttcaa ataattgggt   1440
cttattcata aacggggcgg ccgtgaagaa caagcaaagt gtagattctc gagatttaca   1500
gttgttggct caaactttgc tagtgaagga acaagtggcg agacctgtca tgagggagtt   1560
gcgtgaagca attctgactg agacgaaacc tatcacgtca ttgactgatg tgctgggttt   1620
aatatcaaga aaactgtgga agcagtttgc taacaagatc gcagtcggcg gattcgttgg   1680
catggttggt actctaattg gattctatcc aaagaaggta ctaacctggg cgaaggacac   1740
accaaatggt ccagaactat gttacgagaa ctcgcacaaa accaaggtga tagtatttct   1800
gagtgttgtg tatgccattg gaggaatcac gcttatgcgt cgagacatcc gagatggact   1860
ggtgaaaaaa ctatgtgata tgtttgatat caaacggggg gcccatgtct tagacgttga   1920
```

-continued

```
gaatccgtgc cgctattatg aaatcaacga tttctttagc agtctgtatt cggcatctga    1980
gtccggtgag accgttttac cagatttatc cgaggtaaaa gccaagtctg ataagctatt    2040
gcagcagaag aaagaaatcg ctgacgagtt tctaagtgca aaattctcta actattctgg    2100
cagttcggtg agaacttctc caccatcggt ggtcggttca tctcgaagcg gactgggtct    2160
gttgttggaa gacagtaacg tgctgaccca agctagagtt ggagtttcaa gaaaggtaga    2220
cgatgaggag atcatggagc agtttctgag tggtcttatt gacactgaag cagaaattga    2280
cgaggttgtt ccagcctttt cagctgaatg tgaaagaggg gaaacaagcg gtacaaaggt    2340
gttgtgtaaa cctttaacgc caccaggatt tgagaacgtg ttgccagctg tcaaaccttt    2400
ggtcagcaaa ggaaaaacgg tcaaacgtgt cgattacttc caagtgatgg gaggtgagag    2460
attaccaaaa aggccggttg tcagtggaga cgattctgtg gacgctagaa gagagtttct    2520
gtactactta gatgcggaga gagtcgctca aaatgatgaa attatgtctc tgtatcgtga    2580
ctattcgaga ggagttattc gaactggagg tcagaattac ccgcacggac tgggagtgtg    2640
ggatgtggag atgaagaact ggtgcatacg tccagtggtc actgaacatg cttatgtgtt    2700
ccaaccagac aaacgtatgg atgattggtc gggatactta gaagtggctg tttgggaacg    2760
aggtatgttg gtcaacgact cgcggtcga aggatgagt gattatgtca tagtttgcga    2820
tcagacgtat ctttgcaata acaggttgat cttggacaat ttaagtgccc tggatctagg    2880
accagttaac tgttcttttg aattagttga cggtgtacct ggttgtggta agtcgacaat    2940
gattgtcaac tcagctaatc cttgtgtcga tgtggttctc tctactggga gagcagcaac    3000
cgacgacttg atcgagagat cgcgagcaa aggttttcca tgcaaattga aaaggagagt    3060
gaagacggtt gattctttt tgatgcattg tgttgatggt tctttaaccg gagacgtgtt    3120
gcatttcgat gaagctctca tggcccatgc tggtatggtg tacttttgcg ctcagatagc    3180
tggtgctaaa cgatgtatct gtcaaggaga tcagaatcaa atttctttca agcctagggt    3240
atctcaagtt gatttgaggt tttctagtct ggtcggaaag tttgacattg ttacagaaaa    3300
aagagaaact tacagaagtc cagcagatgt ggctgccgta ttgaacaagt actatactgg    3360
agatgtcaga acacataacg cgactgctaa ttcgatgacg gtgaggaaga ttgtgtctaa    3420
agaacaggtt tctttgaagc ctggtgctca gtacataact ttccttcagt ctgagaagaa    3480
ggagttggta aatttgttgg cattgaggaa agtggcagct aaagtgagta cagtacacga    3540
gtcgcaagga gagacattca agatgtagt cctagtcagg acgaaaccta cggatgactc    3600
aatcgctaga ggtcgggagt acttaatcgt ggcgttgtcg cgtcacacac aatcacttgt    3660
gtatgaaact gtgaaagagg acgatgtaag caaagagatc agggaaagtg ccgcgcttac    3720
gaaggcggct ttggcaagat tttttgttac tgagaccgtc ttatgacggt ttcggtctag    3780
gtttgatgtc tttagacatc atgaagggcc ttgcgccgtt ccagattcag gtacgattac    3840
ggacttggag atgtggtacg acgctttgtt tccgggaaat tcgttaagag actcaagcct    3900
agacgggtat ttggtggcaa cgactgattg caatttgcga ttagacaatg ttacgatcaa    3960
aagtggaaac tggaaagaca gtttgctga aaaagaaacg tttctgaaac cggttattcg    4020
tactgctatg cctgacaaaa ggaagactac tcagttggag agtttgttag cattgcagaa    4080
aaggaaccaa gcggcacccg atctacaaga aaatgtgcac gcaacagttc taatcgaaga    4140
gacgatgaag aagttgaaat ctgttgtcta cgatgtggga aaaattcggg ctgatccctat   4200 tgtcaataga gctcaaatgg agagatggtg gagaaatcaa agcacagcgg tacaggctaa    4260
```

```
ggtagtagca gatgtgagag agttacatga aatagactat tcgtcttaca tgtatatgat    4320
caaatctgac gtgaaaccta agactgattt aacaccgcaa tttgaatact cagctctaca    4380
gactgttgtg tatcacgaga agttgatcaa ctcgttgttc ggtccaattt tcaaagaaat    4440
taatgaacgc aagttggatg ctatgcaacc acattttgtg ttcaacacga gaatgacatc    4500
gagtgattta aacgatcgag tgaagttctt aaatacggaa gcggcttacg actttgttga    4560
gatagacatg tctaaattcg acaagtcggc aaatcgcttc catttacaac tgcagctgga    4620
gatttacagg ttatttgggc tagatgagtg ggcggccttc ctttgggagg tgtcgcacac    4680
tcaaactact gtgagagata ttcaaaatgg tatgatggcg catatttggt accaacaaaa    4740
gagtggagat gctgatactt ataatgcaaa ttcagataga acactgtgtg cactcttgtc    4800
tgaattacca ttggagaaag cagtcatggt tacatatgga ggagatgact cactgattgc    4860
gtttcctaga ggaacgcagt tgttgatcc gtgtccaaag ttggctacta agtggaattt    4920
cgagtgcaag attttaagt acgatgtccc aatgttttgt gggaagttct tgcttaagac    4980
gtcatcgtgt tacgagttcg tgccagatcc ggtaaaagtt ctgacgaagt tggggaaaaa    5040
gagtataaag gatgtgcaac atttagccga gatctacatc tcgctgaatg attccaatag    5100
agctcttggg aactacatgg tggtatccaa actgtccgag tctgttttcag accggtatt    5160 gtacaaaggt gattctgttc atgcgctttg tgcgctatgg aagcatatta agagttttac    5220
agctctgtgt acattattcc gagacgaaaa cgataaggaa ttgaacccgg ctaaggttga    5280
ttggaagaag gcacagagag ctgtgtcaaa cttttacgac tggtaatatg gaagacaagt    5340
cattggtcac cttgaagaag aagactttcg aagtctcaaa attctcaaat ctaggggcca    5400
ttgaattgtt tgtggacggt aggaggaaga gaccgaagta ttttcacaga agaagagaaa    5460
ctgtcctaaa tcatgttggt gggaagaaga gtgaacacaa gttagacgtt tttgaccaaa    5520
gggattacaa aatgattaaa tcttacgcgt ttctaaagat agtaggtgta caactagttg    5580
taacatcaca tctacctgca gatacgcctg ggttcattca aatcgatctg ttggattcga    5640
gacttactga gaaaagaaag agaggaaaga ctattcagag attcaaagct cgagcttgcg    5700
ataactgttc agttgcgcag tacaaggttg aatacagtat ttccacacag gagaacgtac    5760
ttgatgtctg gaaggtgggt tgtatttctg agggcgttcc ggtctgtgac ggtacatacc    5820
ctttcagtat cgaagtgtcg ctaatatggg ttgctactga ttcgactagg cgcctcaatg    5880
tggaagaact gaacagttcg gattacattg aaggcgattt taccgatcaa gaggttttcg    5940
gtgagttcat gtctttgaaa caagtggaga tgaagacgat tgaggcgaag tacgatggtc    6000
cttacagacc agctactact agacctaagt cattattgtc aagtgaagat gttaagagag    6060
cgtctaataa gaaaaactcg tcttaatgca taaagaaatt tattgtcaat atgacgtgtg    6120
tactcaaggg ttgtgtgaat gaagtcactg ttcttggtca cgagacgtgt agtatcggtc    6180
atgctaacaa attgcgaaag caagttgctg acatggttgg tgtcacacgt aggtgtgcgg    6240
aaaataattg tggatggttt gtctgtgttg ttatcaatga ttttactttt gatgtgtata    6300
attgttgtgg ccgtagtcac cttgaaaagt gtcgtaaacg tgttgaaaca agaaatcgag    6360
aaatttggaa acaaattcga cgaaatcaag ctgaaaacat gtctgcgaca gctaaaaagt    6420
ctcataattc gaagacctct aagaagaaat tcaagaggga cagagaattt gggacaccaa    6480
aaagattttt aagagatgat gttcctttcg ggattgatcg tttgtttgct ttttgatttt    6540 atttatatt gttatctgtt tctgtgtata gactgtttga gattggcgct tggccgactc    6600
attgtcttac cataggggaa cggacttttgt ttgtgttgtt attttatttg tatttattta    6660
```

-continued

```
aaattctcaa tgatctgaaa aggcctcgag gctaagagat tattgggggg tgagtaagta   6720
cttttaaagt gatgatggtt acaaaggcaa aaggggtaaa acccctcgcc tacgtaagcg   6780
ttattacgcc c                                                        6791

<210> SEQ ID NO 2
<211> LENGTH: 1707
<212> TYPE: PRT
<213> ORGANISM: Tobacco rattle virus

<400> SEQUENCE: 2

Met Ala Asn Gly Asn Phe Lys Leu Ser Gln Leu Leu Asn Val Asp Glu
1               5                   10                  15

Met Ser Ala Glu Gln Arg Ser His Phe Phe Asp Leu Met Leu Thr Lys
            20                  25                  30

Pro Asp Cys Glu Ile Gly Gln Met Met Gln Arg Val Val Val Asp Lys
        35                  40                  45

Val Asp Asp Met Ile Arg Glu Arg Lys Thr Lys Asp Pro Val Ile Val
    50                  55                  60

His Glu Val Leu Ser Gln Lys Glu Gln Asn Lys Leu Met Glu Ile Tyr
65                  70                  75                  80

Pro Glu Phe Asn Ile Val Phe Lys Asp Asp Lys Asn Met Val His Gly
                85                  90                  95

Phe Ala Ala Ala Glu Arg Lys Leu Gln Ala Leu Leu Leu Leu Asp Arg
            100                 105                 110

Val Pro Ala Leu Gln Glu Val Asp Asp Ile Gly Gly Gln Trp Ser Phe
        115                 120                 125

Trp Val Thr Arg Gly Glu Lys Arg Ile His Ser Cys Cys Pro Asn Leu
    130                 135                 140

Asp Ile Arg Asp Asp Gln Arg Glu Ile Ser Arg Gln Ile Phe Leu Thr
145                 150                 155                 160

Ala Ile Gly Asp Gln Ala Arg Ser Gly Lys Arg Gln Met Ser Glu Asn
                165                 170                 175

Glu Leu Trp Met Tyr Asp Gln Phe Arg Glu Asn Ile Ala Ala Pro Asn
            180                 185                 190

Ala Val Arg Cys Asn Asn Thr Tyr Gln Gly Cys Thr Cys Arg Gly Phe
        195                 200                 205

Ser Asp Gly Lys Lys Lys Gly Ala Gln Tyr Ala Ile Ala Leu His Ser
    210                 215                 220

Leu Tyr Asp Phe Lys Leu Lys Asp Leu Met Ala Thr Met Val Glu Lys
225                 230                 235                 240

Lys Thr Lys Val Val His Ala Ala Met Leu Phe Ala Pro Glu Ser Met
                245                 250                 255

Leu Val Asp Glu Gly Pro Leu Pro Ser Val Asp Gly Tyr Tyr Met Lys
            260                 265                 270

Lys Asn Gly Lys Ile Tyr Phe Gly Phe Glu Lys Asp Pro Ser Phe Ser
        275                 280                 285

Tyr Ile His Asp Trp Glu Glu Tyr Lys Lys Tyr Leu Leu Gly Lys Pro
    290                 295                 300

Val Ser Tyr Gln Gly Asn Val Phe Tyr Phe Glu Pro Trp Gln Val Arg
305                 310                 315                 320

Gly Asp Thr Met Leu Phe Ser Ile Tyr Arg Ile Ala Gly Val Pro Arg
                325                 330                 335

Arg Ser Leu Ser Ser Gln Glu Tyr Tyr Arg Arg Ile Tyr Ile Ser Arg
```

-continued

```
                340                 345                 350
Trp Glu Asn Met Val Val Pro Ile Phe Asp Leu Val Glu Ser Thr
            355                 360                 365
Arg Glu Leu Val Lys Lys Asp Leu Phe Val Glu Lys Gln Phe Met Asp
        370                 375                 380
Lys Cys Leu Asp Tyr Ile Ala Arg Leu Ser Asp Gln Gln Leu Thr Ile
385                 390                 395                 400
Ser Asn Val Lys Ser Tyr Leu Ser Ser Asn Asn Trp Val Leu Phe Ile
                405                 410                 415
Asn Gly Ala Ala Val Lys Asn Lys Gln Ser Val Asp Ser Arg Asp Leu
            420                 425                 430
Gln Leu Leu Ala Gln Thr Leu Leu Val Lys Glu Gln Val Ala Arg Pro
        435                 440                 445
Val Met Arg Glu Leu Arg Glu Ala Ile Leu Thr Glu Thr Lys Pro Ile
    450                 455                 460
Thr Ser Leu Thr Asp Val Gly Leu Ile Ser Arg Lys Leu Trp Lys
465                 470                 475                 480
Gln Phe Ala Asn Lys Ile Ala Val Gly Gly Phe Val Gly Met Val Gly
                485                 490                 495
Thr Leu Ile Gly Phe Tyr Pro Lys Lys Val Leu Thr Trp Ala Lys Asp
            500                 505                 510
Thr Pro Asn Gly Pro Glu Leu Cys Tyr Glu Asn Ser His Lys Thr Lys
        515                 520                 525
Val Ile Val Phe Leu Ser Val Val Tyr Ala Ile Gly Gly Ile Thr Leu
    530                 535                 540
Met Arg Arg Asp Ile Arg Asp Gly Leu Val Lys Lys Leu Cys Asp Met
545                 550                 555                 560
Phe Asp Ile Lys Arg Gly Ala His Val Leu Asp Val Glu Asn Pro Cys
                565                 570                 575
Arg Tyr Tyr Glu Ile Asn Asp Phe Phe Ser Ser Leu Tyr Ser Ala Ser
            580                 585                 590
Glu Ser Gly Glu Thr Val Leu Pro Asp Leu Ser Glu Val Lys Ala Lys
        595                 600                 605
Ser Asp Lys Leu Leu Gln Gln Lys Lys Glu Ile Ala Asp Glu Phe Leu
    610                 615                 620
Ser Ala Lys Phe Ser Asn Tyr Ser Gly Ser Ser Val Arg Thr Ser Pro
625                 630                 635                 640
Pro Ser Val Val Gly Ser Ser Arg Ser Gly Leu Gly Leu Leu Glu
                645                 650                 655
Asp Ser Asn Val Leu Thr Gln Ala Arg Val Gly Val Ser Arg Lys Val
            660                 665                 670
Asp Asp Glu Glu Ile Met Glu Gln Phe Leu Ser Gly Leu Ile Asp Thr
        675                 680                 685
Glu Ala Glu Ile Asp Glu Val Val Pro Ala Phe Ser Ala Glu Cys Glu
    690                 695                 700
Arg Gly Glu Thr Ser Gly Thr Lys Val Leu Cys Lys Pro Leu Thr Pro
705                 710                 715                 720
Pro Gly Phe Glu Asn Val Leu Pro Ala Val Lys Pro Leu Val Ser Lys
                725                 730                 735
Gly Lys Thr Val Lys Arg Val Asp Tyr Phe Gln Val Met Gly Gly Glu
            740                 745                 750
Arg Leu Pro Lys Arg Pro Val Val Ser Gly Asp Asp Ser Val Asp Ala
        755                 760                 765
```

-continued

```
Arg Arg Glu Phe Leu Tyr Tyr Leu Asp Ala Glu Arg Val Ala Gln Asn
770             775                 780

Asp Glu Ile Met Ser Leu Tyr Arg Asp Tyr Ser Arg Gly Val Ile Arg
785                 790                 795                 800

Thr Gly Gly Gln Asn Tyr Pro His Gly Leu Gly Val Trp Asp Val Glu
                805                 810                 815

Met Lys Asn Trp Cys Ile Arg Pro Val Val Thr Glu His Ala Tyr Val
                820                 825                 830

Phe Gln Pro Asp Lys Arg Met Asp Asp Trp Ser Gly Tyr Leu Glu Val
                835                 840                 845

Ala Val Trp Glu Arg Gly Met Leu Val Asn Asp Phe Ala Val Glu Arg
850                 855                 860

Met Ser Asp Tyr Val Ile Val Cys Asp Gln Thr Tyr Leu Cys Asn Asn
865                 870                 875                 880

Arg Leu Ile Leu Asp Asn Leu Ser Ala Leu Asp Leu Gly Pro Val Asn
                885                 890                 895

Cys Ser Phe Glu Leu Val Asp Gly Val Pro Gly Cys Gly Lys Ser Thr
                900                 905                 910

Met Ile Val Asn Ser Ala Asn Pro Cys Val Asp Val Leu Ser Thr
                915                 920                 925

Gly Arg Ala Ala Thr Asp Asp Leu Ile Glu Arg Phe Ala Ser Lys Gly
930                 935                 940

Phe Pro Cys Lys Leu Lys Arg Arg Val Lys Thr Val Asp Ser Phe Leu
945                 950                 955                 960

Met His Cys Val Asp Gly Ser Leu Thr Gly Asp Val Leu His Phe Asp
                965                 970                 975

Glu Ala Leu Met Ala His Ala Gly Met Val Tyr Phe Cys Ala Gln Ile
                980                 985                 990

Ala Gly Ala Lys Arg Cys Ile Cys Gln Gly Asp Gln Asn Gln Ile Ser
                995                1000                1005

Phe Lys Pro Arg Val Ser Gln Val Asp Leu Arg Phe Ser Ser Leu
1010                1015                1020

Val Gly Lys Phe Asp Ile Val Thr Glu Lys Arg Glu Thr Tyr Arg
1025                1030                1035

Ser Pro Ala Asp Val Ala Ala Val Leu Asn Lys Tyr Tyr Thr Gly
1040                1045                1050

Asp Val Arg Thr His Asn Ala Thr Ala Asn Ser Met Thr Val Arg
1055                1060                1065

Lys Ile Val Ser Lys Glu Gln Val Ser Leu Lys Pro Gly Ala Gln
1070                1075                1080

Tyr Ile Thr Phe Leu Gln Ser Glu Lys Lys Glu Leu Val Asn Leu
1085                1090                1095

Leu Ala Leu Arg Lys Val Ala Ala Lys Val Ser Thr Val His Glu
1100                1105                1110

Ser Gln Gly Glu Thr Phe Lys Asp Val Val Leu Val Arg Thr Lys
1115                1120                1125

Pro Thr Asp Asp Ser Ile Ala Arg Gly Arg Glu Tyr Leu Ile Val
1130                1135                1140

Ala Leu Ser Arg His Thr Gln Ser Leu Val Tyr Glu Thr Val Lys
1145                1150                1155

Glu Asp Asp Val Ser Lys Glu Ile Arg Glu Ser Ala Ala Leu Thr
1160                1165                1170
```

```
Lys Ala Ala Leu Ala Arg Phe Phe Val Thr Glu Thr Val Leu Glx
1175              1180              1185

Arg Phe Arg Ser Arg Phe Asp Val Phe Arg His His Glu Gly Pro
1190              1195              1200

Cys Ala Val Pro Asp Ser Gly Thr Ile Thr Asp Leu Glu Met Trp
1205              1210              1215

Tyr Asp Ala Leu Phe Pro Gly Asn Ser Leu Arg Asp Ser Ser Leu
1220              1225              1230

Asp Gly Tyr Leu Val Ala Thr Thr Asp Cys Asn Leu Arg Leu Asp
1235              1240              1245

Asn Val Thr Ile Lys Ser Gly Asn Trp Lys Asp Lys Phe Ala Glu
1250              1255              1260

Lys Glu Thr Phe Leu Lys Pro Val Ile Arg Thr Ala Met Pro Asp
1265              1270              1275

Lys Arg Lys Thr Thr Gln Leu Glu Ser Leu Leu Ala Leu Gln Lys
1280              1285              1290

Arg Asn Gln Ala Ala Pro Asp Leu Gln Glu Asn Val His Ala Thr
1295              1300              1305

Val Leu Ile Glu Glu Thr Met Lys Lys Leu Lys Ser Val Val Tyr
1310              1315              1320

Asp Val Gly Lys Ile Arg Ala Asp Pro Ile Val Asn Arg Ala Gln
1325              1330              1335

Met Glu Arg Trp Trp Arg Asn Gln Ser Thr Ala Val Gln Ala Lys
1340              1345              1350

Val Val Ala Asp Val Arg Glu Leu His Glu Ile Asp Tyr Ser Ser
1355              1360              1365

Tyr Met Tyr Met Ile Lys Ser Asp Val Lys Pro Lys Thr Asp Leu
1370              1375              1380

Thr Pro Gln Phe Glu Tyr Ser Ala Leu Gln Thr Val Val Tyr His
1385              1390              1395

Glu Lys Leu Ile Asn Ser Leu Phe Gly Pro Ile Phe Lys Glu Ile
1400              1405              1410

Asn Glu Arg Lys Leu Asp Ala Met Gln Pro His Phe Val Phe Asn
1415              1420              1425

Thr Arg Met Thr Ser Ser Asp Leu Asn Asp Arg Val Lys Phe Leu
1430              1435              1440

Asn Thr Glu Ala Ala Tyr Asp Phe Val Glu Ile Asp Met Ser Lys
1445              1450              1455

Phe Asp Lys Ser Ala Asn Arg Phe His Leu Gln Leu Gln Leu Glu
1460              1465              1470

Ile Tyr Arg Leu Phe Gly Leu Asp Glu Trp Ala Ala Phe Leu Trp
1475              1480              1485

Glu Val Ser His Thr Gln Thr Thr Val Arg Asp Ile Gln Asn Gly
1490              1495              1500

Met Met Ala His Ile Trp Tyr Gln Gln Lys Ser Gly Asp Ala Asp
1505              1510              1515

Thr Tyr Asn Ala Asn Ser Asp Arg Thr Leu Cys Ala Leu Leu Ser
1520              1525              1530

Glu Leu Pro Leu Glu Lys Ala Val Met Val Thr Tyr Gly Gly Asp
1535              1540              1545

Asp Ser Leu Ile Ala Phe Pro Arg Gly Thr Gln Phe Val Asp Pro
1550              1555              1560

Cys Pro Lys Leu Ala Thr Lys Trp Asn Phe Glu Cys Lys Ile Phe
```

-continued

```
               1565                1570                1575

Lys Tyr Asp Val Pro Met Phe Cys Gly Lys Phe Leu Leu Lys Thr
        1580                1585                1590

Ser Ser Cys Tyr Glu Phe Val Pro Asp Pro Val Lys Val Leu Thr
    1595                1600                1605

Lys Leu Gly Lys Lys Ser Ile Lys Asp Val Gln His Leu Ala Glu
        1610                1615                1620

Ile Tyr Ile Ser Leu Asn Asp Ser Asn Arg Ala Leu Gly Asn Tyr
    1625                1630                1635

Met Val Val Ser Lys Leu Ser Glu Ser Val Ser Asp Arg Tyr Leu
    1640                1645                1650

Tyr Lys Gly Asp Ser Val His Ala Leu Cys Ala Leu Trp Lys His
    1655                1660                1665

Ile Lys Ser Phe Thr Ala Leu Cys Thr Leu Phe Arg Asp Glu Asn
    1670                1675                1680

Asp Lys Glu Leu Asn Pro Ala Lys Val Asp Trp Lys Lys Ala Gln
    1685                1690                1695

Arg Ala Val Ser Asn Phe Tyr Asp Trp
    1700                1705

<210> SEQ ID NO 3
<211> LENGTH: 252
<212> TYPE: PRT
<213> ORGANISM: Tobacco rattle virus

<400> SEQUENCE: 3

Met Glu Asp Lys Ser Leu Val Thr Leu Lys Lys Thr Phe Glu Val
1               5                  10                 15

Ser Lys Phe Ser Asn Leu Gly Ala Ile Glu Leu Phe Val Asp Gly Arg
            20                  25                  30

Arg Lys Arg Pro Lys Tyr Phe His Arg Arg Glu Thr Val Leu Asn
        35                  40                  45

His Val Gly Gly Lys Lys Ser Glu His Lys Leu Asp Val Phe Asp Gln
    50                  55                  60

Arg Asp Tyr Lys Met Ile Lys Ser Tyr Ala Phe Leu Lys Ile Val Gly
65                  70                  75                  80

Val Gln Leu Val Val Thr Ser His Leu Pro Ala Asp Thr Pro Gly Phe
                85                  90                  95

Ile Gln Ile Asp Leu Leu Asp Ser Arg Leu Thr Glu Lys Arg Lys Arg
            100                 105                 110

Gly Lys Thr Ile Gln Arg Phe Lys Ala Arg Ala Cys Asp Asn Cys Ser
        115                 120                 125

Val Ala Gln Tyr Lys Val Glu Tyr Ser Ile Ser Thr Gln Glu Asn Val
    130                 135                 140

Leu Asp Val Trp Lys Val Gly Cys Ile Ser Glu Gly Val Pro Val Cys
145                 150                 155                 160

Asp Gly Thr Tyr Pro Phe Ser Ile Glu Val Ser Leu Ile Trp Val Ala
                165                 170                 175

Thr Asp Ser Thr Arg Arg Leu Asn Val Glu Glu Leu Asn Ser Ser Asp
            180                 185                 190

Tyr Ile Glu Gly Asp Phe Thr Asp Gln Glu Val Phe Gly Glu Phe Met
        195                 200                 205

Ser Leu Lys Gln Val Glu Met Lys Thr Ile Glu Ala Lys Tyr Asp Gly
    210                 215                 220
```

-continued

```
Pro Tyr Arg Pro Ala Thr Thr Arg Pro Lys Ser Leu Leu Ser Ser Glu
225                 230                 235                 240

Asp Val Lys Arg Ala Ser Asn Lys Lys Asn Ser Ser
                245                 250

<210> SEQ ID NO 4
<211> LENGTH: 141
<212> TYPE: PRT
<213> ORGANISM: Tobacco rattle virus

<400> SEQUENCE: 4

Met Thr Cys Val Leu Lys Gly Cys Val Asn Glu Val Thr Val Leu Gly
1               5                   10                  15

His Glu Thr Cys Ser Ile Gly His Ala Asn Lys Leu Arg Lys Gln Val
            20                  25                  30

Ala Asp Met Val Gly Val Thr Arg Arg Cys Ala Glu Asn Asn Cys Gly
        35                  40                  45

Trp Phe Val Cys Val Val Ile Asn Asp Phe Thr Phe Asp Val Tyr Asn
    50                  55                  60

Cys Cys Gly Arg Ser His Leu Glu Lys Cys Arg Lys Arg Val Glu Thr
65                  70                  75                  80

Arg Asn Arg Glu Ile Trp Lys Gln Ile Arg Arg Asn Gln Ala Glu Asn
                85                  90                  95

Met Ser Ala Thr Ala Lys Lys Ser His Asn Ser Lys Thr Ser Lys Lys
            100                 105                 110

Lys Phe Lys Glu Asp Arg Glu Phe Gly Thr Pro Lys Arg Phe Leu Arg
        115                 120                 125

Asp Asp Val Pro Phe Gly Ile Asp Arg Leu Phe Ala Phe
    130                 135                 140

<210> SEQ ID NO 5
<211> LENGTH: 2034
<212> TYPE: DNA
<213> ORGANISM: Tobacco rattle virus

<400> SEQUENCE: 5
ataaaacatt gcacctatgg tgttgccctg gctggggtat gtcagtgatc gcagtagaat      60
gtactaattg acaagttgga gaatacggta gaacgtcctt atccaacaca gcctttatcc     120
ctctccctga cgaggttttt gtcagtgtaa tatttctttt tgaactatcc agcttagtac     180
cgtacgggaa agtgactggt gtgcttatct ttgaaatgtt actttgggtt tcggttcttt     240
aggttagtaa gaaagcactt gtcttctcat acaaaggaaa acctgagacg tatcgcttac     300
gaaagtagca atgaaagaaa ggtggtggtt ttaatcgcta ccgcaaaaac gatggggtcg     360
ttttaattaa cttctcctac gcaagcgtct aaacggacgt tggggttttg ctagtttctt     420
tagagaaaac tagctaagtc tttaatgtta tcattagaga tggcataaat ataatacttg     480
tgtctgctga taagatcatt ttaatttgga cgattagact tgttgaacta caggttactg     540
aatcacttgc gctaatcaac atgggagata tgtacgatga atcatttgac aagtcgggcg     600
gtcctgctga cttgatggac gattcttggg tggaatcagt ttcgtggaaa gatctgttga     660
agaagttaca cagcataaaa tttgcactac agtctggtag agatgagatc actgggttac     720
tagcggcact gaatagacag tgtccttatt caccatatga gcagtttcca gataagaagg     780
tgtatttcct tttagactca cgggctaaca gtgctcttgg tgtgattcag aacgcttcag     840
cgttcaagag acgagctgat gagaagaatg cagtggcggg tgttacaaat attcctgcga     900
```

-continued

```
atccaaacac aacggttacg acgaaccaag ggagtactac tactaccaag gcgaacactg    960
gctcgactttt ggaagaagac ttgtacactt attacaaatt cgatgatgcc tctacagctt   1020
tccacaaatc tctaacttcg ttagagaaca tggagttgaa gagttattac cgaaggaact   1080
ttgagaaagt attcgggatt aagtttggtg gagcagctgc tagttcatct gcaccgcctc   1140
cagcgagtgg aggtccgata cgtcctaatc cctagggatt taaggacgtg aactctgttg   1200
agatctctgt gaaattcaga gggtgggtga taccatattc actgatgcca ttagcgacat   1260
ctaaataggg ctaattgtga ctaatttgag ggaatttcct ttaccattga cgtcagtgtc   1320
gttggtagca tttgagtttc gcaatgcacg aattacttag gaagtggctt gacgacacta   1380
atgtgttatt gttagataat ggtttggtgg tcaaggtacg tagtagagtc ccacatattc   1440
gcacgtatga agtaattgga aagttgtcag tttttgataa ttcactggga gatgatacgc   1500
tgtttgaggg aaaagtagag aacgtatttg tttttatgtt caggcggttc ttgtgtgtca   1560
acaaagatgg acattgttac tcaaggaagc acgatgagct ttattattac ggacgagtgg   1620
acttagattc tgtgagtaaa tgtcccgaag acattaaact acggttcttt aagtagatcc   1680
gtgtctgaag ttttaggttc aatttaaacc tacgagattg acattctcga ctgatcttga   1740
ttgatcggta agtcttttgt aatttaattt tcttttttgat tttatttttaa attgttatct  1800
gtttctgtgt atagactgtt tgagatcggc gtttggccga ctcattgtct taccataggg   1860
gaacggactt tgtttgtgtt gttatttttat ttgtattttta ttaaaattct caacgatctg  1920
aaaaagcctc gcggctaaga gattgttggg gggtgagtaa gtacttttaa agtgatgatg   1980
gttacaaagg caaaaggggt aaaaccctc gcctacgtaa gcgttattac gccc          2034
```

<210> SEQ ID NO 6
<211> LENGTH: 204
<212> TYPE: PRT
<213> ORGANISM: Tobacco rattle virus

<400> SEQUENCE: 6

```
Met Gly Asp Met Tyr Asp Glu Ser Phe Asp Lys Ser Gly Gly Pro Ala
1               5                   10                  15

Asp Leu Met Asp Asp Ser Trp Val Glu Ser Val Ser Trp Lys Asp Leu
            20                  25                  30

Leu Lys Lys Leu His Ser Ile Lys Phe Ala Leu Gln Ser Gly Arg Asp
        35                  40                  45

Glu Ile Thr Gly Leu Leu Ala Ala Leu Asn Arg Gln Cys Pro Tyr Ser
    50                  55                  60

Pro Tyr Glu Gln Phe Pro Asp Lys Lys Val Tyr Phe Leu Leu Asp Ser
65                  70                  75                  80

Arg Ala Asn Ser Ala Leu Gly Val Ile Gln Asn Ala Ser Ala Phe Lys
                85                  90                  95

Arg Arg Ala Asp Glu Lys Asn Ala Val Ala Gly Val Thr Asn Ile Pro
            100                 105                 110

Ala Asn Pro Asn Thr Thr Val Thr Thr Asn Gln Gly Ser Thr Thr Thr
        115                 120                 125

Thr Lys Ala Asn Thr Gly Ser Thr Leu Glu Glu Asp Leu Tyr Thr Tyr
    130                 135                 140

Tyr Lys Phe Asp Asp Ala Ser Thr Ala Phe His Lys Ser Leu Thr Ser
145                 150                 155                 160

Leu Glu Asn Met Glu Leu Lys Ser Tyr Tyr Arg Arg Asn Phe Glu Lys
                165                 170                 175
```

```
Val Phe Gly Ile Lys Phe Gly Gly Ala Ala Ala Ser Ser Ser Ala Pro
            180                 185                 190
Pro Pro Ala Ser Gly Gly Pro Ile Arg Pro Asn Pro
        195                 200
```

<210> SEQ ID NO 7
<211> LENGTH: 94
<212> TYPE: DNA
<213> ORGANISM: Artificial Sequence
<220> FEATURE:
<223> OTHER INFORMATION: primer OYL64

<400> SEQUENCE: 7
ggcccgggcc cgtttcgtcc tttagggact cgtcagtgta ctgatataag tacagacggg    60
cgtaataacg cttacgtagg cgaggggttt tacc    94

<210> SEQ ID NO 8
<211> LENGTH: 35
<212> TYPE: DNA
<213> ORGANISM: Artificial Sequence
<220> FEATURE:
<223> OTHER INFORMATION: upstream primer OYL61

<400> SEQUENCE: 8
ataaaacatt tcaatccttt gaacgcggta gaacg    35

<210> SEQ ID NO 9
<211> LENGTH: 25
<212> TYPE: DNA
<213> ORGANISM: Artificial Sequence
<220> FEATURE:
<223> OTHER INFORMATION: forward primer

<400> SEQUENCE: 9
ctgacgagct ttcgatgcag tgcat    25

<210> SEQ ID NO 10
<211> LENGTH: 25
<212> TYPE: DNA
<213> ORGANISM: Artificial Sequence
<220> FEATURE:
<223> OTHER INFORMATION: reverse primer

<400> SEQUENCE: 10
atatatggac atttatcaca ggaac    25

<210> SEQ ID NO 11
<211> LENGTH: 30
<212> TYPE: DNA
<213> ORGANISM: Artificial Sequence
<220> FEATURE:
<223> OTHER INFORMATION: forward primer

<400> SEQUENCE: 11
atggagctat gatgttttct taagttttag    30

<210> SEQ ID NO 12
<211> LENGTH: 28
<212> TYPE: DNA
<213> ORGANISM: Artificial Sequence
<220> FEATURE:
<223> OTHER INFORMATION: reverse primer

<400> SEQUENCE: 12
gaaggccttt agcataattt actacctc    28

```
<210> SEQ ID NO 13
<211> LENGTH: 24
<212> TYPE: DNA
<213> ORGANISM: Artificial Sequence
<220> FEATURE:
<223> OTHER INFORMATION: primer

<400> SEQUENCE: 13
aggaaagcac acaacagaaa aacc                                          24

<210> SEQ ID NO 14
<211> LENGTH: 24
<212> TYPE: DNA
<213> ORGANISM: Artificial Sequence
<220> FEATURE:
<223> OTHER INFORMATION: primer

<400> SEQUENCE: 14
gtgccatcct ttggtgcatg gagg                                          24

<210> SEQ ID NO 15
<211> LENGTH: 26
<212> TYPE: DNA
<213> ORGANISM: Artificial Sequence
<220> FEATURE:
<223> OTHER INFORMATION: forward primer

<400> SEQUENCE: 15
gagtatcaga ccaagtgtga tatccg                                        26

<210> SEQ ID NO 16
<211> LENGTH: 24
<212> TYPE: DNA
<213> ORGANISM: Artificial Sequence
<220> FEATURE:
<223> OTHER INFORMATION: reverse primer

<400> SEQUENCE: 16
gctgaggtgg gagtgttttc cacc                                          24

<210> SEQ ID NO 17
<211> LENGTH: 24
<212> TYPE: DNA
<213> ORGANISM: Artificial Sequence
<220> FEATURE:
<223> OTHER INFORMATION: primer

<400> SEQUENCE: 17
gaaagagcct aaaattgtag tgtc                                          24

<210> SEQ ID NO 18
<211> LENGTH: 24
<212> TYPE: DNA
<213> ORGANISM: Artificial Sequence
<220> FEATURE:
<223> OTHER INFORMATION: primer

<400> SEQUENCE: 18
ctatttccta aaagggagct tatt                                          24

<210> SEQ ID NO 19
<211> LENGTH: 27
<212> TYPE: DNA
<213> ORGANISM: Artificial Sequence
<220> FEATURE:
```

```
-continued

<223> OTHER INFORMATION: Rar1 primer

<400> SEQUENCE: 19
cctttcatcc ggtcatggaa gatagcg                                              27

<210> SEQ ID NO 20
<211> LENGTH: 24
<212> TYPE: DNA
<213> ORGANISM: Artificial Sequence
<220> FEATURE:
<223> OTHER INFORMATION: forward primer

<400> SEQUENCE: 20
aggaaagcac acaacagaaa aacc                                                 24

<210> SEQ ID NO 21
<211> LENGTH: 24
<212> TYPE: DNA
<213> ORGANISM: Artificial Sequence
<220> FEATURE:
<223> OTHER INFORMATION: EDS1 primer

<400> SEQUENCE: 21
gtttcttagt tcctccactt ctgc                                                 24

<210> SEQ ID NO 22
<211> LENGTH: 26
<212> TYPE: DNA
<213> ORGANISM: Artificial Sequence
<220> FEATURE:
<223> OTHER INFORMATION: EDS1 primer

<400> SEQUENCE: 22
gagtatcaga ccaagtgtga tatccg                                               26

<210> SEQ ID NO 23
<211> LENGTH: 26
<212> TYPE: DNA
<213> ORGANISM: Artificial Sequence
<220> FEATURE:
<223> OTHER INFORMATION: NUP and NPR1/NIM1 primer

<400> SEQUENCE: 23
caacgtggaa agaagcgttt tccaag                                               26

<210> SEQ ID NO 24
<211> LENGTH: 25
<212> TYPE: DNA
<213> ORGANISM: Artificial Sequence
<220> FEATURE:
<223> OTHER INFORMATION: NPR1/NIM1 primer

<400> SEQUENCE: 24
tcttgctatg gcaggcgatg atttg                                                25

<210> SEQ ID NO 25
<211> LENGTH: 29
<212> TYPE: DNA
<213> ORGANISM: Artificial Sequence
<220> FEATURE:
<223> OTHER INFORMATION: primer

<400> SEQUENCE: 25
cggtctagag gcactcaact ttataaacc                                            29
```

```
<210> SEQ ID NO 26
<211> LENGTH: 29
<212> TYPE: DNA
<213> ORGANISM: Artificial Sequence
<220> FEATURE:
<223> OTHER INFORMATION: primer

<400> SEQUENCE: 26
cggggatccc ttcagttttc tgtcaaacc                              29

<210> SEQ ID NO 27
<211> LENGTH: 32
<212> TYPE: DNA
<213> ORGANISM: Artificial Sequence
<220> FEATURE:
<223> OTHER INFORMATION: primer

<400> SEQUENCE: 27
cgggaattcg ttgcaattat gaagcggttg cg                          32

<210> SEQ ID NO 28
<211> LENGTH: 33
<212> TYPE: DNA
<213> ORGANISM: Artificial Sequence
<220> FEATURE:
<223> OTHER INFORMATION: primer

<400> SEQUENCE: 28
cggctcgagt catgagagca actgcatgtc tgt                         33

<210> SEQ ID NO 29
<211> LENGTH: 32
<212> TYPE: DNA
<213> ORGANISM: Artificial Sequence
<220> FEATURE:
<223> OTHER INFORMATION: primer

<400> SEQUENCE: 29
cgggaattcg cccttgatgt ggcaaagggc at                          32

<210> SEQ ID NO 30
<211> LENGTH: 32
<212> TYPE: DNA
<213> ORGANISM: Artificial Sequence
<220> FEATURE:
<223> OTHER INFORMATION: primer

<400> SEQUENCE: 30
cggctcgagg tagaatttac tgagatttcc tg                          32

<210> SEQ ID NO 31
<211> LENGTH: 52
<212> TYPE: DNA
<213> ORGANISM: Artificial Sequence
<220> FEATURE:
<223> OTHER INFORMATION: primer

<400> SEQUENCE: 31
cgggaattct agaggcgcgc caaataatga ttttattttg actgatagtg ac    52

<210> SEQ ID NO 32
<211> LENGTH: 45
<212> TYPE: DNA
<213> ORGANISM: Artificial Sequence
<220> FEATURE:
<223> OTHER INFORMATION: primer
```

```
-continued

<400> SEQUENCE: 32
cggctcgaga gctcaaataa tgattttatt ttgactgata gtgac            45

<210> SEQ ID NO 33
<211> LENGTH: 49
<212> TYPE: DNA
<213> ORGANISM: Artificial Sequence
<220> FEATURE:
<223> OTHER INFORMATION: primer

<400> SEQUENCE: 33
ggggacaagt tgtacaaaa aagcaggctc tgacgagctt tcgatgcag         49

<210> SEQ ID NO 34
<211> LENGTH: 49
<212> TYPE: DNA
<213> ORGANISM: Artificial Sequence
<220> FEATURE:
<223> OTHER INFORMATION: primer

<400> SEQUENCE: 34
ggggaccact tgtacaaga aagctgggta tatatggaca tttatcaca         49

<210> SEQ ID NO 35
<211> LENGTH: 54
<212> TYPE: DNA
<213> ORGANISM: Artificial Sequence
<220> FEATURE:
<223> OTHER INFORMATION: primer

<400> SEQUENCE: 35
ggggacaagt tgtacaaaa aagcaggctc tgcttcctct gtcatttctt cagc    54

<210> SEQ ID NO 36
<211> LENGTH: 54
<212> TYPE: DNA
<213> ORGANISM: Artificial Sequence
<220> FEATURE:
<223> OTHER INFORMATION: primer

<400> SEQUENCE: 36
ggggaccact tgtacaaga aagctgggtc cacttgacgc acattgtcga atcc    54

<210> SEQ ID NO 37
<211> LENGTH: 49
<212> TYPE: DNA
<213> ORGANISM: Artificial Sequence
<220> FEATURE:
<223> OTHER INFORMATION: forward primer

<400> SEQUENCE: 37
ggggacaagt tgtacaaaa aagcaggctc ccccgggctg caggaattc         49

<210> SEQ ID NO 38
<211> LENGTH: 50
<212> TYPE: DNA
<213> ORGANISM: Artificial Sequence
<220> FEATURE:
<223> OTHER INFORMATION: reverse primer

<400> SEQUENCE: 38
ggggaccact tgtacaaga aagctgggtg gtaccgggcc cccctcgag         50

<210> SEQ ID NO 39
<211> LENGTH: 25
```

```
<212> TYPE: DNA
<213> ORGANISM: Artificial Sequence
<220> FEATURE:
<223> OTHER INFORMATION: primer

<400> SEQUENCE: 39
actgtttcct tagagagcaa ggtag                                              25

<210> SEQ ID NO 40
<211> LENGTH: 27
<212> TYPE: DNA
<213> ORGANISM: Artificial Sequence
<220> FEATURE:
<223> OTHER INFORMATION: primer

<400> SEQUENCE: 40
caactaatag tccgtttcca aaagacc                                            27
```